(12) United States Patent
Finn et al.

(10) Patent No.: US 11,802,110 B2
(45) Date of Patent: Oct. 31, 2023

(54) 2-AMINO-N-(ARYLSULFINYL)-ACETAMIDE COMPOUNDS AS INHIBITORS OF BACTERIAL AMINOACYL-TRNA SYNTHETASE

(71) Applicant: Oxford Drug Design Limited, London (GB)

(72) Inventors: Paul William Finn, London (GB); Michael Charlton, London (GB); Grace Edmund, London (GB); Aigars Jirgensons, Riga (LV); Einars Loza, Riga (LV)

(73) Assignee: Oxford Drug Design Limited, London (GB)

( * ) Notice: Subject to any disclaimer, the term of this patent is extended or adjusted under 35 U.S.C. 154(b) by 1109 days.

(21) Appl. No.: 16/339,542

(22) PCT Filed: Oct. 6, 2017

(86) PCT No.: PCT/EP2017/075567
§ 371 (c)(1),
(2) Date: Apr. 4, 2019

(87) PCT Pub. No.: WO2018/065611
PCT Pub. Date: Apr. 12, 2018

(65) Prior Publication Data
US 2020/0039929 A1 Feb. 6, 2020

(30) Foreign Application Priority Data
Oct. 7, 2016 (GB) ...................................... 1617064

(51) Int. Cl.
| | | |
|---|---|---|
| *C07C 323/63* | (2006.01) | |
| *A61P 31/04* | (2006.01) | |
| *C07C 317/14* | (2006.01) | |
| *C07D 213/71* | (2006.01) | |
| *C07D 221/04* | (2006.01) | |
| *C07D 231/12* | (2006.01) | |
| *C07D 307/64* | (2006.01) | |
| *C07D 333/34* | (2006.01) | |
| *C07F 7/08* | (2006.01) | |

(52) U.S. Cl.
CPC ............ *C07C 323/63* (2013.01); *A61P 31/04* (2018.01); *C07C 317/14* (2013.01); *C07D 213/71* (2013.01); *C07D 221/04* (2013.01); *C07D 231/12* (2013.01); *C07D 307/64* (2013.01); *C07D 333/34* (2013.01); *C07F 7/081* (2013.01)

(58) Field of Classification Search
CPC .................................................... C07C 323/63
USPC ........................................................ 514/311
See application file for complete search history.

(56) References Cited

U.S. PATENT DOCUMENTS

| | | |
|---|---|---|
| 2011/0230350 A1 | 9/2011 | Frackenpohl et al. |
| 2018/0022696 A1 | 1/2018 | Jirgensons et al. |
| 2020/0288710 A1 | 9/2020 | F lein et al. NAME |

FOREIGN PATENT DOCUMENTS

| | | |
|---|---|---|
| CN | 1906208 A | 1/2007 |
| CN | 105198789 A | 12/2015 |
| EP | 3429355 B1 | 2/2020 |
| JP | H05-208914 A | 8/1993 |
| JP | 2004-502670 A | 1/2004 |
| WO | WO-98/41215 A1 | 9/1998 |
| WO | WO-02/02513 A1 | 1/2002 |
| WO | WO-02/098848 A1 | 12/2002 |
| WO | WO-2005/037860 A2 | 4/2005 |
| WO | WO-2014/018569 A1 | 1/2014 |
| WO | WO-2016/129983 A1 | 8/2016 |
| WO | WO-2018/065611 A1 | 4/2018 |

OTHER PUBLICATIONS

King, Med. Chem., Principle and Practice (1994), pp. 206-208.*
Chemical Abstracts, Chemical Compounds with Registry Nos. 1279200-48-4; 1279037-24-9; 775277-16-2; 765873-02-7 (2019) (1 page).
Chemical Abstracts, Chemical Compounds with Registry Nos. 1786245-31-5; 1786215-48-2; 1786212-05-2; 1786204-28-1; 1786200-20-1; 1786109-38-3; 1786096-26-1; 1786086-91-6; 1279200-48-4; 1279037-24-9 (2019) (5 pages).

(Continued)

*Primary Examiner* — Taofiq A Solola
(74) *Attorney, Agent, or Firm* — Clark & Elbing LLP

(57) ABSTRACT

The present invention pertains generally to the field of therapeutic compounds. More specifically the present invention pertains to certain 2-amino-N-(arylsulfinyl)-acetamide compounds that, inter alia, inhibit (e.g., selectively inhibit) bacterial aminoacyl-tRNA synthetase (aaRS) (e.g., bacterial leucyl-t RNA synthetase, LeuRS). The present invention also pertains to pharmaceutical compositions comprising such compounds, and the use of such compounds and compositions, both in vitro and in vivo, to inhibit (e.g., selectively inhibit) bacterial aminoacyl-tRNA synthetase; to treat disorders that are ameliorated by the inhibition (e.g., selective inhibition) of bacterial aminoacyl-tRNA synthetase; to treat bacterial infections; etc.

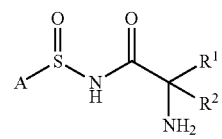

28 Claims, No Drawings

(56) References Cited

OTHER PUBLICATIONS

Johansson et al., "Acyl sulfonamides as potent protease inhibitors of the hepatitis C virus full-length NS3 (protease-helicase/NTPase): A comparative study of different C-terminals," Bioorg Med Chem. 11(12):2551-68 (2003).
Orelle et al., "Identifying the targets of aminoacyl-tRNA synthetase inhibitors by primer extension inhibition," Nucleic Acids Res. 41(14):e144 (2013).
STN record CAS RN: 625122-57-8 (Dec. 9, 2003) (1 page).
Zheng et al., "One-pot asymmetric synthesis of 2-aryl-2,3-dihydro-4-quinolones catalyzed by amino acid-derived sulfonamides," Tetrahedron: Asymmetry. 24:875-882 (2013).
Anderson, "The process of structure-based drug design," Chem Biol. 10(9):787-97 (2003).
Chemical Abstracts, Chemical Compounds with Registry Nos. 1786215-48-2; 1786212-05-2; 1786200-20-1; and 1786086-91-6 (2005) (2 pages).
Chen et al., "Chiral Molecular Clips Control Orthogonal Crystalline Organization," Org Lett. 9(10):1899-1902 (2007).
Gadakh et al., "Aminoacyl-tRNA synthetase inhibitors as antimicrobial agents: a patent review from 2006 till present," Expert Opin Ther Pat. 22(12): 1453-65 (2012).
Hurdle et al., "Prospects for aminoacyl-tRNA synthetase inhibitors as new antimicrobial agents," Antimicrobial Agents and Chemotherapy. 49(12): 4821-33 (2005).
International Search Report and Written Opinion for International Patent Application No. PCT/EP2017/075567, dated May 12, 2017 (8 pages).
Kerrigan et al., "Synthesis of arylpiperazines via palladium-catalysed aromatic amination reactions of bromoarenes with N-tert-butoxycarbonylpiperazine," Tetrahedron Letters. 39(15): 2219-22 (1998).
Laupland et al., "Treatment of staphylococcus aureus colonization and prophylaxis for infection with topical intranasal mupirocin: An evidence-based review," Clin Infect Dis. 37(7): 933-8 (2003).
Ochsner et al., "Aminoacyl-tRNA synthetases: essential and still promising targets for new anti-infective agents," Expert Opin Investig Drugs. 16(5): 573-93 (2007).
Pham et al., "Aminoacyl-tRNA synthetases as drug targets in eukaryotic parasites," Int J Parasitol Drugs Drug Resist. 4(1):1-13 (2014).
Savile et al., "Subtilisin-catalyzed resolution of N-acyl arylsulfinamides," J Am Chem Soc. 127(7): 2104-13 (2005).
Shi et al., "Discovery of a series of novel compounds with moderate anti-hepatitis C virus NS3 protease activity in vitro," Bioorg Med Chem. 23(17): 5539-45 (2015).
Thea et al., "Sulfoquinones in the hydrolysis of aryl esters of o- and p-hydroxyarenesulfonic acids in alkaline aqueous solutions of dioxane," J Org Chem. 50(12): 2158-65 (1985).
Theil, "Structure-aided drug design's next generation," Nat Biotechnol. 22(5):513-9 (2004).
Vondenhoff et al., "Aminoacyl-tRNA synthetase inhibitors as potential antibiotics," Eur J Med Chem. 46(11): 5227-36 (2011).
Zhang et al., "Discovery of N-(4-sulfamoylphenyl)thioureas as Trypanosoma brucei leucyl-tRNA synthetase inhibitors," Org Biomol Chem. 11(32): 5310-24 (2013).

\* cited by examiner

2-AMINO-N-(ARYLSULFINYL)-ACETAMIDE COMPOUNDS AS INHIBITORS OF BACTERIAL AMINOACYL-TRNA SYNTHETASE

RELATED APPLICATION

This application is related to United Kingdom patent application number 1617064.9 filed 7 Oct. 2016, the contents of which are incorporated herein by reference in their entirety.

TECHNICAL FIELD

The present invention pertains generally to the field of therapeutic compounds. More specifically the present invention pertains to certain 2-amino-N-(arylsulfinyl)-acetamide compounds that, inter alia, inhibit (e.g., selectively inhibit) bacterial aminoacyl-tRNA synthetase (aaRS) (e.g., bacterial leucyl-tRNA synthetase, LeuRS). The present invention also pertains to pharmaceutical compositions comprising such compounds, and the use of such compounds and compositions, both in vitro and in vivo, to inhibit (e.g., selectively inhibit) bacterial aminoacyl-tRNA synthetase; to treat disorders that are ameliorated by the inhibition (e.g., selective inhibition) of bacterial aminoacyl-tRNA synthetase; to treat bacterial infections; etc.

BACKGROUND

A number of publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

Bacterial Aminoacyl-tRNA Synthetase

Widespread resistance to currently used antibacterial drugs has encouraged the search for novel chemotherapeutics with slow or completely blocked resistance development. This could be achieved by targeting the functional bacterial proteins, the mutation of which leads to reduction of bacterial fitness.

Bacterial enzymes called aminoacyl-tRNA synthetases (aaRS) have been recognized as such molecular targets for drug development. See, e.g., Gadakh et al., 2012; Vondenhoff et al., 2011; and Pham et al., 2014.

The aminoacyl-tRNA synthetase (aaRS) family of enzymes catalyse the addition of proteinaceous amino acids to their cognate tRNA. The product aminoacyl-tRNA participates in the translation of messenger RNA into protein at the ribosome. The aaRS mechanism proceeds as follows: it binds ATP and the corresponding amino acid and forms an aminoacyl-adenylate intermediate, releasing inorganic pyrophosphate (PPi). The adenylate-aaRS complex binds the appropriate tRNA molecule, and the amino acid is transferred from the aminoacyl-AMP to either the 2'- or the 3'-OH of the last tRNA nucleotide at the 3'-end.

The mechanism can be summarized in the following reaction series:

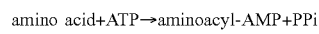

amino acid+ATP→aminoacyl-AMP+PPi

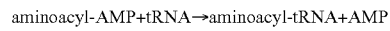

aminoacyl-AMP+tRNA→aminoacyl-tRNA+AMP

Two classes of aminoacyl-tRNA synthetases (aaRS) are known: "Class I" (with two highly conserved sequence motifs, and which aminoacylates at the 2'-OH of a terminal adenosine nucleotide on tRNA) and "Class II" (with three highly conserved sequence motifs, and which aminoacylates at the 3'-OH of a terminal adenosine on tRNA). Included among the known aminoacyl-tRNA synthetases are: Alanyl-tRNA synthetase; Arginyl-tRNA synthetase; Aspartyl-tRNA synthetase; Glutamyl-tRNA synthetase; Glycyl-tRNA synthetase; Histidyl-RNA synthetase; Isoleucyl-tRNA synthetase; Leucyl-tRNA synthetase; Lysyl-tRNA synthetase; Methionyl-tRNA synthetase; Phenylalanyl-tRNA synthetase; Seryl-tRNA synthetase; Threonyl-tRNA synthetase; Tryptophanyl-tRNA synthetase; Tyrosyl-tRNA synthetase; and Valyl-tRNA synthetase.

Bacterial aminoacyl-tRNA synthetases (aaRS) possess several features that render them promising broad-spectrum antibacterial drug targets; they are essential for viability, found in all bacterial pathogens, and are in many cases sufficiently structurally distinct from their eukaryotic counterparts to allow selective targeting (see, e.g., Hurdle et al., 2005; Ochsner et al., 2007). Furthermore, there exists both chemical and clinical validation for these enzymes as useful targets for antibacterial chemotherapy.

However, despite the potential promise of this family of targets, only one aaRS inhibitor with a relatively limited indication has to date been approved for the management of bacterial infection. Specifically, mupirocin (also known as Bactroban and Centany; shown below) is an inhibitor of isoleucyl-tRNA synthetase that has been approved for use as a topical agent for nasal decolonization of *Staphylococcus aureus* and for the treatment of superficial skin infection (see, e.g., Laupland et al., 2003).

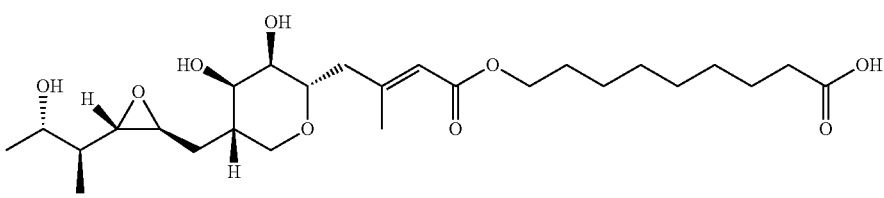 [SMILES: C/C(=C\C(=O)OCCCCCCCCC(=O)O)C[C@@H]1OC[C@H](C[C@@H]2O[C@H]2[C@@H](C)[C@H](C)O)[C@@H](O)[C@H]1O]

Several inhibitors for other bacterial tRNA synthetases have been developed; however, so far none have been approved for use in medicine.

The inventors have identified a novel class of small molecule inhibitors of bacterial aminoacyl-tRNA synthetase (specifically, bacterial leucyl-tRNA synthetase) which are useful in the treatment of a range of conditions, including bacterial infections.

Known Compounds

It appears that the following compounds are known (see, e.g., Savile et al., 2005).

| Code | Structure | Registry No. |
|---|---|---|
| P01 | 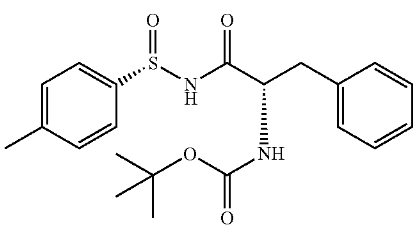 [SMILES: Cc1ccc([S@](=O)NC(=O)[C@H](Cc2ccccc2)NC(=O)OC(C)(C)C)cc1] | 847980-66-9 |
| P02 | 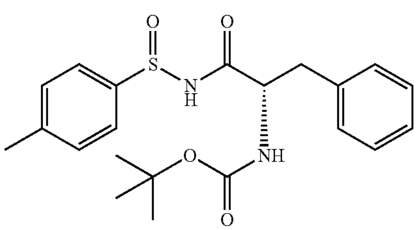 [SMILES: Cc1ccc(S(=O)NC(=O)[C@H](Cc2ccccc2)NC(=O)OC(C)(C)C)cc1] | 847980-39-6 |
| P03 | 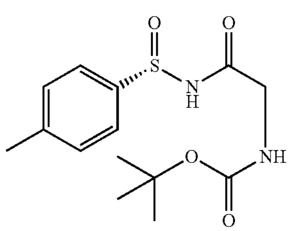 [SMILES: Cc1ccc([S@](=O)NC(=O)CNC(=O)OC(C)(C)C)cc1] | 847980-65-8 |
| P04 | 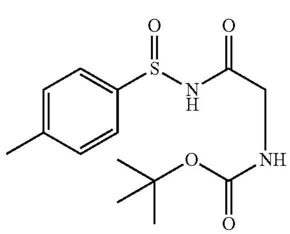 [SMILES: Cc1ccc(S(=O)NC(=O)CNC(=O)OC(C)(C)C)cc1] | 847980-38-5 |

Cottrell et al., 2005 describes the following compound (see, e.g., Scheme 19 on page 87 therein) as a chemical intermediate used in the synthesis of certain serine protease inhibitors.

| Code | Structure | Registry No. |
|---|---|---|
| P05 | 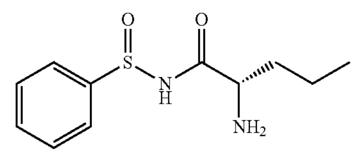 [SMILES: CCC[C@H](N)C(=O)NS(=O)c1ccccc1] | |

Duron et al., 2014 describes the following compound (see, e.g., Compound 31 in Example 8 on page 75 therein) (a sulfone compound, not a sulfine compound) as a chemical intermediate used in the synthesis of certain cystathionine-γ-gamma-lyase (CSE) inhibitors.

| Code | Structure | Registry No. |
|---|---|---|
| P06 | 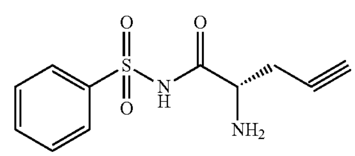 [SMILES: C#CC[C@H](N)C(=O)NS(=O)(=O)c1ccccc1] | |

SUMMARY OF THE INVENTION

One aspect of the invention pertains to certain 2-amino-N-(arylsulfinyl)-acetamide compounds (referred to herein as ANASA compounds), as described herein.

Another aspect of the invention pertains to a composition (e.g., a pharmaceutical composition) comprising an ANASA compound, as described herein, and a pharmaceutically acceptable carrier or diluent.

Another aspect of the invention pertains to a method of preparing a composition (e.g., a pharmaceutical composition) comprising the step of mixing an ANASA compound, as described herein, and a pharmaceutically acceptable carrier or diluent.

Another aspect of the present invention pertains to a method of inhibiting (e.g., selectively inhibiting) bacterial aminoacyl-tRNA synthetase (aaRS) (e.g., bacterial leucyl-tRNA synthetase, LeuRS, etc.), in vitro or in vivo, comprising contacting the synthetase with an effective amount of an ANASA compound, as described herein.

Another aspect of the present invention pertains to a method of inhibiting (e.g., selectively inhibiting) bacterial aminoacyl-tRNA synthetase (aaRS) (e.g., bacterial leucyl-tRNA synthetase, LeuRS, etc.) function in a cell (e.g., a bacterial cell), in vitro or in vivo, comprising contacting the cell with an effective amount of an ANASA compound, as described herein.

Another aspect of the present invention pertains to an ANASA compound as described herein for use in a method of treatment of the human or animal body by therapy, for example, for use in a method of treatment of a disorder (e.g., a disease) as described herein.

Another aspect of the present invention pertains to use of an ANASA compound, as described herein, in the manufacture of a medicament, for example, for use in a method of treatment, for example, for use in a method of treatment of a disorder (e.g., a disease) as described herein.

Another aspect of the present invention pertains to a method of treatment, for example, a method of treatment of a disorder (e.g., a disease) as described herein, comprising administering to a subject in need of treatment a therapeutically-effective amount of an ANASA compound, as described herein, preferably in the form of a pharmaceutical composition.

In one embodiment, the treatment is treatment of a disorder of the human or animal body that is ameliorated by the inhibition (e.g., selective inhibition) of bacterial aminoacyl-tRNA synthetase (aaRS) (e.g., bacterial leucyl-tRNA synthetase, LeuRS).

In one embodiment, the treatment is treatment of a bacterial infection.

Another aspect of the present invention pertains to a kit comprising (a) an ANASA compound, as described herein, preferably provided as a pharmaceutical composition and in a suitable container and/or with suitable packaging; and (b) instructions for use, for example, written instructions on how to administer the compound.

Another aspect of the present invention pertains to an ANASA compound obtainable by a method of synthesis as described herein, or a method comprising a method of synthesis as described herein.

Another aspect of the present invention pertains to an ANASA compound obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspects of the invention.

DETAILED DESCRIPTION OF THE INVENTION

Compounds

One aspect of the present invention relates to certain compounds that may conveniently be described as 2-amino-N-(arylsulfinyl)-acetamide compounds. One simple example of such compounds is 2-amino-N-(benzenesulfinyl)acetamide, shown below.

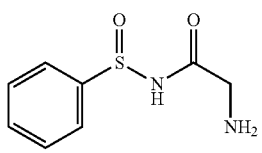 [SMILES: NCC(=O)NS(=O)c1ccccc1]

The compounds are characterized by a —S(=O)—NH—C(=O)—C(NH$_2$)<linkage, with an aryl group (referred to herein as -A) attached to the sulfur atom (at the far left), and two groups (referred to herein as —R$^1$ and —R$^2$) attached to the alpha carbon atom (at the far right).

Thus, one aspect of the present invention pertains to compounds of the following formula, and pharmaceutically acceptable salts, hydrates, and solvates thereof, wherein -A, —R$^1$, and —R$^2$ are as defined herein (for convenience, collectively referred to herein as "2-amino-N-(arylsulfinyl)-acetamide compounds" or "ANASA compounds"):

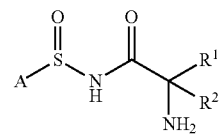

The left-hand group, A-S(=O)—NH—, may be conveniently considered to be an aryl-sulfinamide moiety. The right-hand group, —C(=O)—CR$^1$R$^2$—NH$_2$, may be conveniently considered to be an alpha-amino acid residue.

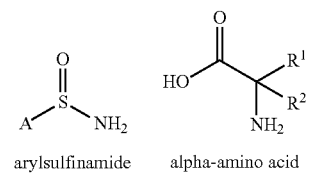

arylsulfinamide    alpha-amino acid

Some embodiments of the invention include the following:

(1) A compound selected from compounds of the following formula, and pharmaceutically acceptable salts, hydrates, and solvates thereof:

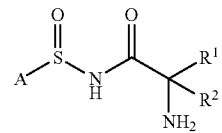

wherein:
-A is independently -A$^C$ or -A$^H$;
-A$^C$ is independently phenyl or naphthyl, and is optionally substituted with one or more substituents —R$^X$;
-A$^H$ is independently C$_{5-12}$heteroaryl, and is optionally substituted with one or more substituents —R$^X$;
each —R$^X$ is independently selected from:
—R$^{XX}$, —R$^{XXU}$, —R$^{XXV}$, —R$^{XXH}$,
—F, —Cl, —Br, —I,
—OH, —OR$^{XX}$,
-L$^{XX}$-OH, -L$^{XX}$-OR$^{XX}$,
—CF$_3$, —OCF$_3$,
—NH$_2$, —NHR$^{XX}$, —NR$^{XX}$$_2$, —R$^{XM}$,
-L$^{XX}$-NH$_2$, -L$^{XX}$-NHR$^{XX}$, -L$^{XX}$-NR$^{XX}$$_2$, -L$^{XX}$-R$^{XM}$,
—C(=O)OH, —C(=O)OR$^{XX}$, —OC(=O)R$^{XX}$,
—C(=O)NH$_2$, —C(=O)NHR$^{XX}$, —C(=O)NR$^{XX}$$_2$,
—C(=O)R$^{XM}$,
—NHC(=O)R$^{XX}$, —NR$^{XN}$C(=O)R$^{XX}$,
—NHC(=O)NH$_2$, —NHC(=O)NHR$^{XX}$, —NHC(=O)NR$^{XX}$$_2$, —NHC(=O)R$^{XM}$, —NR$^{XN}$C(=O)NH$_2$, —NR$^{XN}$C(=O)NHR$^{XX}$,
—NR$^{XN}$C(=O)NR$^{XX}$$_2$, —NR$^{XN}$C(=O)R$^{XM}$,
—NHC(=O)OR$^{XX}$, —NR$^{XN}$C(=O)OR$^{XX}$,
—OC(=O)NH$_2$, —OC(=O)NHR$^{XX}$, —OC(=O)NR$^{XX}$$_2$, —OC(=O)R$^{XM}$,
—NHC(=NH)NH$_2$,
—C(=O)R$^{XX}$,
—S(=O)NH$_2$, —S(=O)NHR$^{XX}$, —S(=O)NR$^{XX}$$_2$, —S(=O)R$^{XM}$,
—S(=O)$_2$NH$_2$, —S(=O)$_2$NHR$^{XX}$, —S(=O)$_2$NR$^{XX}$$_2$, —S(=O)$_2$R$^{XM}$,
—NHS(=O)R$^{XX}$, —NR$^{XN}$S(=O)R$^{XX}$,
—NHS(=O)$_2$R$^{XX}$, —NR$^{XN}$S(=O)$_2$R$^{XX}$,
—S(=O)R$^{XX}$, —S(=O)$_2$R$^{XX}$,
—SH, —SR$^{XX}$, —CN, and —NO$_2$;
and additionally, two adjacent groups —R$^X$, if present, may together form:
—O—CH$_2$—O— or —O—CH$_2$CH$_2$—O—;
wherein:
each -L$^{XX}$- is linear or branched saturated C$_{1-4}$alkylene;
each —R$^{XX}$ is independently linear or branched saturated C$_{1-4}$alkyl, phenyl, or benzyl;
each —R$^{XXU}$ is independently linear or branched C$_{2-4}$alkenyl;
each —R$^{XXV}$ is independently linear or branched C$_{2-4}$alkynyl;
each —R$^{XXH}$ is C$_{5-10}$ heteroaryl, and is optionally substituted with one or more groups —R$^{XMM}$;
each —R$^{XN}$ is linear or branched saturated C$_{1-4}$alkyl;
each —R$^{XM}$ is independently azetidino, pyrrolidino, piperidino, piperazino, morpholino, azepano, or diazepano, and is:
optionally substituted with one or more groups selected from:
—R$^{XMM}$, —C(=O)R$^{XMM}$, —C(=O)OR$^{XMM}$, and —S(=O)$_2$R$^{XMM}$;
wherein each —R$^{XMM}$ is independently linear or branched saturated C$_{1-4}$alkyl, phenyl, or benzyl;
—R$^1$ is independently —H or —R$^{11}$;
—R$^{11}$ is independently —R$^{11A}$ or —R$^{11B}$;
—R$^{11A}$ is independently:
—R$^{A1}$, —R$^{A2}$, —R$^{A3}$, —R$^{A4}$, —R$^{A5}$, -L$^A$-R$^{A2}$, -L$^A$-R$^{A3}$, -L$^A$-R$^{A4}$, or -L$^A$-R$^{A5}$;
each —R$^{A1}$ is linear or branched saturated C$_{1-6}$alkyl, and is optionally substituted with one or more groups —R$^{AA2}$;
each —R$^{A2}$ is saturated C$_{3-6}$cycloalkyl, and is optionally substituted with one or more groups —R$^{AA1}$ and one or more groups —R$^{AA2}$;
each —R$^{A3}$ is non-aromatic C$_{3-7}$heterocyclyl, and is optionally substituted with one or more groups —R$^{AA1}$ and one or more groups —R$^{AA2}$;
each —R$^{A4}$ is independently phenyl or naphthyl, and is optionally substituted with one or more groups —R$^{AA1}$ and one or more groups —R$^{AA2}$;
each —R$^{A5}$ is C$_{5-10}$heteroaryl, and is optionally substituted with one or more groups —R$^{AA1}$ and one or more groups —R$^{AA2}$;
each -L$^A$- is linear or branched saturated C$_{1-4}$alkylene;
each —R$^{AA}$ is independently selected from:
—R$^{AA}$,
-L$^{AA}$-OH, -L$^{AA}$-OR$^{AA}$,
-L$^{AA}$-NH$_2$, -L$^{AA}$-NHR$^{AA}$, -L$^{AA}$-NR$^{AA2}$, and -L$^{AA}$-R$^{AM}$;
each —R$^{AA2}$ is independently selected from:
—F, —Cl, —Br, —I,
—OH, —OR$^{AA}$,
—OCF$_3$, —NH$_2$, —NHR$^{AA}$, —NR$^{AA}$$_2$, —R$^{AM}$,
—C(=O)OH, —C(=O)OR$^{AA}$, —OC(=O)R$^{AA}$,
—C(=O)NH$_2$, —C(=O)NHR$^{AA}$, —C(=O)NR$^{AA2}$, —C(=O)R$^{AM}$,
—NHC(=O)R$^{AA}$, —NR$^{AN}$C(=O)R$^{AA}$,
—NHC(=O)NH$_2$, —NHC(=O)NH R$^{AA}$, —NHC(=O)NR$^{AA2}$, —NHC(=O)R$^{AM}$,
—NR$^{AN}$C(=O)NH$_2$, —NR$^{AN}$C(=O)NHR$^{AA}$,
—NR$^{AN}$C(=O)NR$^{AA2}$, —NR$^{AN}$C(=O)R$^{AM}$,
—NHC(=O)OR$^{AA}$, —NR$^{AN}$C(=O)OR$^{AA}$,
—OC(=O)NH$_2$, —OC(=O)NHR$^{AA}$, —OC(=O)NR$^{AA2}$, —OC(=O)R$^{AM}$,
—NHC(=NH)NH$_2$,
—C(=O)R$^{AA}$,
—S(=O)NH$_2$, —S(=O)NHR$^{AA}$, —S(=O)NR$^{AA2}$, —S(=O)R$^{AM}$,
—S(=O)$_2$NH$_2$, —S(=O)$_2$NHR$^{AA}$, —S(=O)$_2$NR$^{AA2}$, —S(=O)$_2$R$^{AM}$,
—NHS(=O)R$^{AA}$, —NR$^{AN}$S(=O)R$^{AA}$,
—NHS(=O)$_2$R$^{AA}$, —NR$^{AN}$S(=O)$_2$R$^{AA}$,
—S(=O)R$^{AA}$, —S(=O)$_2$R$^{AA}$,
—SH, —SR$^{AA}$, —CN, and —NO$_2$;
wherein:
each -L$^{AA}$- is linear or branched saturated C$_{1-4}$alkylene;
each —R$^{AA}$ is independently linear or branched saturated C$_{1-4}$alkyl, phenyl, or benzyl;
each —R$^{AN}$ is linear or branched saturated C$_{1-4}$alkyl;
each —R$^{AM}$ is independently azetidino, pyrrolidino, piperidino, piperazino, morpholino, azepano, or diazepano, and is:
optionally substituted with one or more groups selected from:
—R$^{AMM}$, —C(=O)R$^{AMM}$, —C(=O)OR$^{AMM}$, and —S(=O)$_2$R$^{AMM}$;
wherein each —R$^{AMM}$ is independently linear or branched saturated C$_{1-4}$alkyl, phenyl, or benzyl;
—R$^{11B}$ is independently selected from:
—F, —Cl, —Br, —I,
—OH, —OR$^{BB}$,
—OCF$_3$,
—NH$_2$, —NHR$^{BB}$, —NR$^{BB}$$_2$, —R$^{BM}$,
—C(=O)OH, —C(=O)OR$^{BB}$, —OC(=O)R$^{BB}$,
—C(=O)NH$_2$, —C(=O)NHR$^{BB}$, —C(=O)NR$^{BB}$$_2$, —C(=O)R$^{BM}$,
—NHC(=O)R$^{BB}$, —NR$^{BN}$C(=O)R$^{BB}$,
—NHC(=O)NH$_2$, —NHC(=O)NHR$^{BB}$, —NHC(=O)NR$^{BB}$$_2$, —NHC(=O)R$^{BM}$,
—NR$^{BN}$C(=O)NH$_2$, —NR$^{BN}$C(=O)NHR$^{BB}$,
—NR$^{BN}$C(=O)NR$^{BB}$$_2$, —NR$^{BN}$C(=O)R$^{BM}$,
—NHC(=O)OR$^{BB}$, —NR$^{BN}$C(=O)OR$^{BB}$,
—OC(=O)NH$_2$, —OC(=O)NHR$^{BB}$, —OC(=O)NR$^{BB}$$_2$, —OC(=O)R$^{BM}$,
—NHC(=NH)NH$_2$,
—C(=O)R$^{BB}$,
—S(=O)NH$_2$, —S(=O)NHR$^{BB}$, —S(=O)NR$^{BB}$$_2$, —S(=O)R$^{BM}$,
—S(=O)$_2$NH$_2$, —S(=O)$_2$NHR$^{BB}$, —S(=O)$_2$NR$^{BB}$$_2$, —S(=O)$_2$R$^{BM}$,
—NHS(=O)R$^{BB}$, —NR$^{BN}$S(=O)R$^{BB}$,
—NHS(=O)$_2$R$^{BB}$, —NR$^{BN}$S(=O)$_2$R$^{BB}$,
—S(=O)R$^{BB}$, —S(=O)$_2$R$^{BB}$,
—SH, —SR$^{BB}$, —CN, and —NO$_2$;
wherein:
each —R$^{BB}$ is independently linear or branched saturated C$_{1-4}$alkyl, phenyl, or benzyl;
each —R$^{BN}$ is linear or branched saturated C$_{1-4}$alkyl;

each —$R^{BM}$ is independently azetidino, pyrrolidino, piperidino, piperazino, morpholino, azepano, or diazepano, and is:
optionally substituted with one or more groups selected from:
—$R^{BMM}$, —C(=O)$R^{BMM}$, —C(=O)O$R^{BMM}$, and —S(=O)$_2 R^{BMM}$;
wherein each —$R^{BMM}$ is independently linear or branched saturated $C_{1-4}$alkyl, phenyl, or benzyl;
—$R^2$ is independently —H or —$R^{22}$;
—$R^{22}$ is independently —$R^{22C}$ or —$R^{22D}$;
—$R^{22C}$ is independently:
—$R^{C1}$, —$R^{C2}$, —$R^{C3}$, —$R^{C4}$, —$R^{C5}$, -$L^C$-$R^{C2}$, -$L^C$-$R^{C3}$, -$L^C$-$R^{C4}$, or -$L^C$-$R^{C5}$;
each —$R^{C1}$ is linear or branched saturated $C_{1-6}$alkyl, and is optionally substituted with one or more groups —$R^{CC2}$;
each —$R^{C2}$ is saturated $C_{3-6}$cycloalkyl, and is optionally substituted with one or more groups —$R^{CC1}$ and one or more groups —$R^{CC2}$;
each —$R^{C3}$ is non-aromatic $C_{3-7}$heterocyclyl, and is optionally substituted with one or more groups —$R^{CC1}$ and one or more groups —$R^{CC2}$;
each —$R^{C4}$ is independently phenyl or naphthyl, and is optionally substituted with one or more groups —$R^{CC1}$ and one or more groups —$R^{CC2}$;
each —$R^{C5}$ is $C_{5-10}$heteroaryl, and is optionally substituted with one or more groups —$R^{CC1}$ and one or more groups —$R^{CC2}$;
each -$L^C$- is linear or branched saturated $C_{1-4}$alkylene;
each —$R^{CC1}$ is independently selected from:
—$R^{CC}$,
-$L^{CC}$-OH, -$L^{CC}$-O$R^{CC}$,
-$L^{CC}$-NH$_2$, -$L^{CC}$-NHR$^{CC}$, -$L^{CC}$-N$R^{CC}_2$, and -$L^{CC}$-$R^{CM}$;
each —$R^{CC2}$ is independently selected from:
—F, —Cl, —Br, —I,
—OH, —O$R^{CC}$,
—OCF$_3$,
—NH$_2$, —NHR$^{CC}$, —N$R^{CC}_2$, —$R^{CM}$,
—C(=O)OH, —C(=O)O$R^{CC}$, —OC(=O)$R^{CC}$,
—C(=O)NH$_2$, —C(=O)NHR$^{CC}$, —C(=O)N$R^{CC}_2$, —C(=O)$R^{CM}$,
—NHC(=O)$R^{CC}$, —N$R^{CN}$C(=O)$R^{CC}$,
—NHC(=O)NH$_2$, —NHC(=O)NHR$^{CC}$, —NHC(=O)N$R^{CC}_2$, —NHC(=O)$R^{CM}$,
—N$R^{CN}$C(=O)NH$_2$, —N$R^{CN}$C(=O)NHR$^{CC}$, —N$R^{CN}$C(=O)N$R^{CC}_2$, —N$R^{CN}$C(=O)$R^{CM}$,
—NHC(=O)O$R^{CC}$, —N$R^{CN}$C(=O)O$R^{CC}$,
—OC(=O)NH$_2$, —OC(=O)NHR$^{CC}$, —OC(=O)N$R^{CC}_2$, —OC(=O)$R^{CM}$,
—NHC(=NH)NH$_2$,
—C(=O)$R^{CC}$,
—S(=O)NH$_2$, —S(=O)NHR$^{CC}$, —S(=O)N$R^{CC}_2$, —S(=O)$R^{CM}$,
—S(=O)$_2$NH$_2$, —S(=O)$_2$NHR$^{CC}$, —S(=O)$_2$N$R^{CC}_2$, —S(=O)$_2 R^{CM}$,
—NHS(=O)$R^{CC}$, —N$R^{CN}$S(=O)$R^{CC}$,
—NHS(=O)$_2 R^{CC}$, —N$R^{CN}$S(=O)$_2 R^{CC}$,
—S(=O)$R^{CC}$, —S(=O)$_2 R^{CC}$,
—SH, —S$R^{CC}$, —CN, and —NO$_2$;
wherein:
each -$L^{CC}$- is linear or branched saturated $C_{1-4}$alkylene;
each —$R^{CC}$ is independently linear or branched saturated $C_{1-4}$alkyl, phenyl, or benzyl;
each —$R^{CN}$ is linear or branched saturated $C_{1-4}$alkyl;

each —$R^{CM}$ is independently azetidino, pyrrolidino, piperidino, piperazino, morpholino, azepano, or diazepano, and is:
optionally substituted with one or more groups selected from:
—$R^{CMM}$, —C(=O)$R^{CMM}$, —C(=O)O$R^{CMM}$, and —S(=O)$_2 R^{CMM}$;
wherein each —$R^{AMM}$ is independently linear or branched saturated $C_{1-4}$alkyl, phenyl, or benzyl;
—$R^{22D}$ is independently selected from:
—F, —Cl, —Br, —I,
—OH, —O$R^{DD}$,
—OCF$_3$,
—NH$_2$, —NHR$^{DD}$, —N$R^{DD}_2$, —$R^{DM}$,
—C(=O)OH, —C(=O)O$R^{DD}$, —OC(=O)$R^{DD}$,
—C(=O)NH$_2$, —C(=O)NHR$^{DD}$, —C(=O)N$R^{DD}_2$, —C(=O)$R^{DM}$,
—NHC(=O)$R^{DD}$, —N$R^{DN}$C(=O)$R^{DD}$,
—NHC(=O)NH$_2$, —NHC(=O)NHR$^{DD}$, —NHC(=O)N$R^{DD}_2$, —NHC(=O)$R^{DM}$,
—N$R^{DN}$C(=O)NH$_2$, —N$R^{DN}$C(=O)NHR$^{DD}$,
—N$R^{DN}$C(=O)N$R^{DD}_2$, —N$R^{DN}$C(=O)$R^{DM}$,
—NHC(=O)O$R^{DD}$, —N$R^{DN}$C(=O)O$R^{DD}$,
—OC(=O)NH$_2$, —OC(=O)NHR$^{DD}$, —OC(=O)N$R^{DD}_2$, —OC(=O)$R^{DM}$,
—NHC(=NH)NH$_2$,
—C(=O)$R^{DD}$,
—S(=O)NH$_2$, —S(=O)NHR$^{DD}$, —S(=O)N$R^{DD}_2$, —S(=O)$R^{DM}$,
—S(=O)$_2$NH$_2$, —S(=O)$_2$NHR$^{DD}$, —S(=O)$_2$N$R^{DD}_2$, —S(=O)$_2 R^{DM}$,
—NHS(=O)$R^{DD}$, —N$R^{DN}$S(=O)$R^{DD}$,
—NHS(=O)$_2 R^{DD}$, —N$R^{DN}$S(=O)$_2 R^{DD}$,
—S(=O)$R^{DD}$, —S(=O)$_2 R^{DD}$,
—SH, —S$R^{DD}$, —CN, and —NO$_2$;
wherein:
each —$R^{DD}$ is independently linear or branched saturated $C_{1-4}$alkyl, phenyl, or benzyl;
each —$R^{DN}$ is linear or branched saturated $C_{1-4}$alkyl;
each —$R^{DM}$ is independently azetidino, pyrrolidino, piperidino, piperazino, morpholino, azepano, or diazepano, and is:
optionally substituted with one or more groups selected from:
—$R^{DMM}$, —C(=O)$R^{DMM}$, —C(=O)O$R^{DMM}$, and —S(=O)$_2 R^{DMM}$;
wherein each —$R^{BMM}$ is independently linear or branched saturated $C_{1-4}$alkyl, phenyl, or benzyl;
or —$R^1$ and —$R^2$, together with the carbon atom to which they are attached, form a saturated $C_{3-6}$cycloalkyl or a non-aromatic $C_{3-7}$heterocyclyl, and is optionally substituted with one or more groups —$R^{CC2}$.

For convenience, the following table sets out the various groups mentioned above.

TABLE 1

List of Groups

| | | | | | |
|---|---|---|---|---|---|
| A | $A^C$ | $R^X$ | $L^{XX}$ | | |
|  | $A^H$ |  | $R^{XX}$ | | |
|  |  |  | $R^{XXU}$ | | |
|  |  |  | $R^{XXV}$ | | |
|  |  |  | $R^{XXH}$ | $R^{XXM}$ | |
|  |  |  | $R^{XN}$ | | |
|  |  |  | $R^{XM}$ | $R^{XXM}$ | |
| $R^1$ | $R^{11}$ | $R^{11A}$ | $R^{A1}$ | $R^{AA1}$ | $L^{AA}$ |
|  |  |  | $R^{A2}$ | $R^{AA2}$ | $R^{AA}$ |

TABLE 1-continued

List of Groups

| | | | | | | |
|---|---|---|---|---|---|---|
| | | | $R^{A3}$ | | $R^{AN}$ | |
| | | | $R^{A4}$ | | $R^{AM}$ | $R^{AMM}$ |
| | | | $R^{A5}$ | | | |
| | | | $L^{A}$ | | | |
| | $R^{11B}$ | | $R^{BB}$ | | | |
| | | | $R^{BN}$ | | | |
| | | | $R^{BM}$ | $R^{BMM}$ | | |
| $R^2$ | $R^{22}$ | $R^{22C}$ | $R^{C1}$ | $R^{CC1}$ | $L^{CC}$ | |
| | | | $R^{C2}$ | $R^{CC2}$ | $R^{CC}$ | |
| | | | $R^{C3}$ | | $R^{CN}$ | |
| | | | $R^{C4}$ | | $R^{CM}$ | $R^{CMM}$ |
| | | | $R^{C5}$ | | | |
| | | | $L^{C}$ | | | |
| | | $R^{22D}$ | $R^{DD}$ | | | |
| | | | $R^{DN}$ | | | |
| | | | $R^{DM}$ | $R^{DMM}$ | | |

For the avoidance of doubt, it is intended that the —NH$_2$ group (which forms part of the —S(=O)—NH—C(=O)—C(NH$_2$)<linkage) is unmodified (e.g., is unsubstituted; is unprotected; etc.).

Furthermore, for the avoidance of doubt, it is intended that the —NH— group (which forms part of the —S(=O)—NH—C(=O)—C(NH$_2$)<linkage) is unmodified (e.g., is unsubstituted; is unprotected; etc.).

Furthermore, for the avoidance of doubt, it is not intended that any part of the —S(=O)—NH—C(=O)—C(NH$_2$) <linkage forms part of ring.

Furthermore, for the avoidance of doubt, it is not intended that -A and —R$^1$, taken together, or -A and —R$^2$, taken together, form part of a ring. For example, it is not intended that -A and —R$^1$ are additionally linked, other than via the linkage —S(=O)—NH—C(=O)—CR$^2$—. Similarly, it is not intended that -A and —R$^2$ are additionally linked, other than via the linkage —S(=O)—NH—C(=O)—CR$^1$—. However, in certain embodiments, as described herein, —R$^1$ and —R$^2$, together with the carbon atom to which they are attached, may form a ring.

Note that the compounds have at least one chiral centre, specifically, the sulfur atom which forms part of the sulfoxide group, marked with an asterisk (*) in the following formula. Unless otherwise stated, the sulfur atom at this position may be in either (R) or (S) configuration.

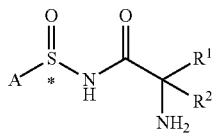

Also note that, depending upon the identity of the groups —R$^1$ and —R$^2$, the compounds may have a second chiral centre, specifically, the carbon atom to which —R$^1$ and —R$^2$ are attached, marked with a hash (#) in the following formula. Unless otherwise stated, the carbon atom at this position may be in either (R) or (S) configuration.

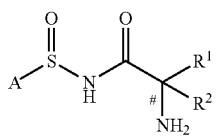

For the avoidance of doubt, and unless otherwise stated, a reference to a compound or compounds without specifying the configuration of one or both chiral centres is intended to encompass all possible configurations. For example, the following formula (which is silent with respect to stereochemistry):

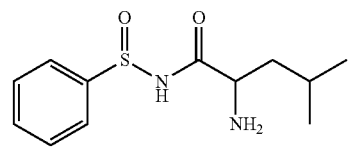 [SMILES: CC(C)CC(N)C(=O)NS(=O)c1ccccc1]

is intended to encompass all four diastereomers:

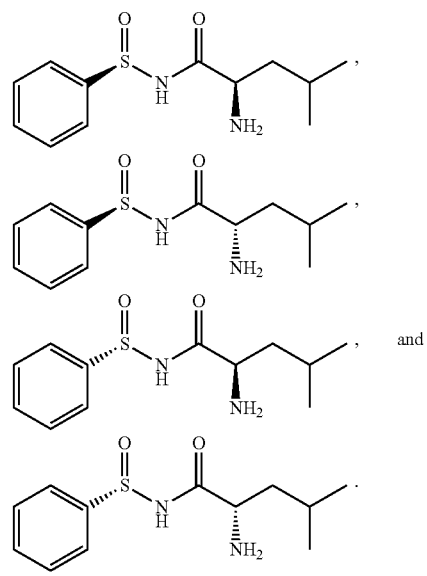

Similarly, the following formula (which is silent with respect to the stereochemistry at the sulfur atom):

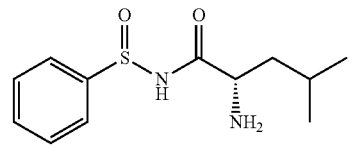 [SMILES: CC(C)C[C@H](N)C(=O)NS(=O)c1ccccc1]

is intended to encompass both enantiomers:

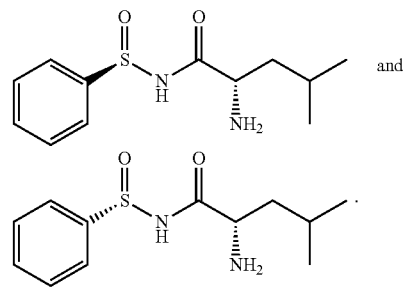

The Group -A
(2) A compound according to (1), wherein -A is -A$^C$.
(3) A compound according to (1), wherein -A is -A$^H$.

The Group -A$^C$
(4) A compound according to any one of (1) to (3), wherein -A$^C$, if present, is phenyl or naphthyl, and is optionally substituted with 1, 2, or 3 substituents —R$^X$.
(5) A compound according to any one of (1) to (3), wherein -A$^C$, if present, is phenyl, and is optionally substituted with one or more substituents —R$^X$.
(6) A compound according to any one of (1) to (3), wherein -A$^C$, if present, is phenyl, and is optionally substituted with 1, 2, or 3 substituents —R$^X$.
(7) A compound according to any one of (1) to (3), wherein -A$^C$, if present, is independently selected from:

[chemical structures]

wherein each —R$^{X1}$, —R$^{X2}$, —R$^{X3}$, —R$^{X4}$, —R$^{X5}$, and —R$^{X6}$ is independently as defined for —R$^X$.

(8) A compound according to any one of (1) to (3), wherein -A$^C$, if present, is independently selected from:

[chemical structures]

wherein each —R$^{X1}$, —R$^{X2}$, and —R$^{X3}$ is independently as defined for —R$^X$.

(9) A compound according to any one of (1) to (3), wherein -A$^C$, if present, is:

[chemical structure]

wherein —R$^{X1}$ is independently as defined for —R$^X$.

(10) A compound according to any one of (1) to (3), wherein -A$^C$, if present, is:

[chemical structure]

wherein —R$^{X2}$ is independently as defined for —R$^X$.

(11) A compound according to any one of (1) to (3), wherein -A$^C$, if present, is:

[chemical structure]

wherein —R$^{X3}$ is independently as defined for —R$^X$.

(12) A compound according to any one of (1) to (3), wherein -A$^C$, if present, is phenyl.
(13) A compound according to any one of (1) to (3), wherein -A$^C$, if present, is naphthyl, and is optionally substituted with one or more substituents —R$^X$.
(14) A compound according to any one of (1) to (3), wherein -A$^C$, if present, is naphthyl, and is optionally substituted with 1, 2, or 3 substituents —R$^X$.
(15) A compound according to any one of (1) to (3), wherein -A$^C$, if present, is naphthyl.

The Group -A$^H$
(16) A compound according to any one of (1) to (15), wherein -A$^H$, if present, is C$_{5-10}$ heteroaryl, and is optionally substituted with one or more substituents —R$^X$.
(17) A compound according to any one of (1) to (15), wherein -A$^H$, if present, is C$_{5-10}$ heteroaryl, and is optionally substituted with 1, 2, or 3 substituents —R$^X$.
(18) A compound according to any one of (1) to (15), wherein -A$^H$, if present, is C$_{5-6}$heteroaryl or C$_{9-10}$ heteroaryl, and is optionally substituted with one or more substituents —R$^X$.
(19) A compound according to any one of (1) to (15), wherein -A$^H$, if present, is furanyl, thienyl, pyrrolyl, pyrazolyl, imidazolyl, oxazolyl, isoxazolyl, thiazolyl, isothiazolyl, pyridyl, pyridazinyl, pyrimidinyl, pyrazinyl, indolyl, benzimidazolyl, indazolyl, benzofuranyl, benzothienyl, benzooxazolyl, benzoisoxazolyl, benzothiazolyl, benzoisothiazolyl, quinolinyl, isoquinolinyl, cinnolinyl, quinazolinyl, quinoxalinyl, phthalazinyl, or benzopyranyl, and is optionally substituted with one or more substituents —$R^X$.

(20) A compound according to any one of (1) to (15), wherein -$A^H$, if present, is furanyl, thienyl, pyrrolyl, pyrazolyl, imidazolyl, oxazolyl, isoxazolyl, thiazolyl, isothiazolyl, pyridyl, pyridazinyl, pyrimidinyl, pyrazinyl, and is optionally substituted with one or more substituents —$R^X$.

(21) A compound according to any one of (1) to (15), wherein -$A^H$, if present, is pyridyl, pyridazinyl, pyrimidinyl, or pyrazinyl, and is optionally substituted with one or more substituents —$R^X$.

(22) A compound according to any one of (1) to (15), wherein -$A^H$, if present, is pyridyl, furanyl, or thienyl, and is optionally substituted with one or more substituents —$R^X$.

(23) A compound according to any one of (1) to (15), wherein -$A^H$, if present, is pyridyl, and is optionally substituted with one or more substituents —$R^X$.

(24) A compound according to any one of (1) to (15), wherein -$A^H$, if present, is furanyl, and is optionally substituted with one or more substituents —$R^X$.

(25) A compound according to any one of (1) to (15), wherein -$A^H$, if present, is thienyl, and is optionally substituted with one or more substituents —$R^X$.

(26) A compound according to any one of (1) to (15), wherein -$A^H$, if present, is indolyl, benzimidazolyl, indazolyl, benzofuranyl, benzothienyl, benzooxazolyl, benzoisoxazolyl, benzothiazolyl, benzoisothiazolyl, quinolinyl, isoquinolinyl, cinnolinyl, quinazolinyl, quinoxalinyl, phthalazinyl, or benzopyranyl, and is optionally substituted with one or more substituents —$R^X$.

(27) A compound according to any one of (1) to (15), wherein -$A^H$, if present, is indolyl, benzimidazolyl, indazolyl, benzofuranyl, quinolinyl, isoquinolinyl, quinazolinyl, or quinoxalinyl, and is optionally substituted with one or more substituents —$R^X$.

(28) A compound according to any one of (1) to (15), wherein -$A^H$, if present, is quinolinyl or isoquinolinyl, and is optionally substituted with one or more substituents —$R^X$.

(29) A compound according to any one of (1) to (15), wherein -$A^H$, if present, is quinolinyl, and is optionally substituted with one or more substituents —$R^X$.

The Group(s) —$R^X$

(30) A compound according to any one of (1) to (29), wherein each —$R^X$, if present, is independently selected from:
—$R^{XX}$,
—F, —Cl, —Br, —I,
—OH, —$OR^{XX}$,
$L^{XX}$-OH, -$L^{XX}$-$OR^{XX}$,
—$CF_3$, —$OCF_3$,
—$NH_2$, —$NHR^{XX}$, —$NR^{XX}_2$, —$R^{XM}$,
$L^{XX}$-$NH_2$, -$L^{XX}$-$NHR^{XX}$, -$L^{XX}$-$NR^{XX}_2$, -$L^{XX}$-$R^{XM}$,
—C(=O)OH, —C(=O)$OR^{XX}$, —OC(=O)$R^{XX}$,
—C(=O)$NH_2$, —C(=O)$NHR^{XX}$, —C(=O)$NR^{XX}_2$,
—C(=O)$R^{XM}$,
—NHC(=O)$R^{XX}$, —$NR^{XN}$C(=O)$R^{XX}$,
—NHC(=O)$NH_2$, —NHC(=O)$NHR^{XX}$, —NHC(=O)$NR^{XX}_2$, —NHC(=O)$R^{XM}$,
—$NR^{XN}$C(=O)$NH_2$, —$NR^{XN}$C(=O)$NHR^{XX}$,
—$NR^{XN}$C(=O)$NR^{XX}_2$, —$NR^{XN}$C(=O)$R^{XM}$,
—NHC(=O)$OR^{XX}$, —$NR^{XN}$C(=O)$OR^{XX}$,
—OC(=O)$NH_2$, —OC(=O)$NHR^{XX}$, —OC(=O)$NR^{XX}_2$, —OC(=O)$R^{XM}$,
—NHC(=NH)$NH_2$,
—C(=O)$R^{XX}$,
—S(=O)$NH_2$, —S(=O)$NHR^{XX}$, —S(=O)$NR^{XX}_2$,
—S(=O)$R^{XM}$,
—$S(=O)_2NH_2$, —$S(=O)_2NHR^{XX}$, —$S(=O)_2NR^{XX}_2$,
—$S(=O)_2R^{XM}$,
—NHS(=O)$R^{XX}$, —$NR^{XN}$S(=O)$R^{XX}$,
—$NHS(=O)_2R^{XX}$, —$NR^{XN}S(=O)_2R^{XX}$,
—S(=O)$R^{XX}$, —$S(=O)_2R^{XX}$,
—SH, —$SR^{XX}$, —CN, and —$NO_2$;
and additionally, two adjacent groups —$R^X$, if present, may together form:
—O—$CH_2$—O— or —O—$CH_2CH_2$—O—.

(31) A compound according to any one of (1) to (29), wherein each —$R^X$, if present, is independently selected from:
—$R^{XX}$, —$R^{XXU}$, —$R^{XXV}$, —$R^{XXH}$,
—F, —Cl, —Br, —I,
—OH, —$OR^{XX}$,
—$CF_3$, —$OCF_3$,
—$NH_2$, —$NHR^{XX}$, —$NR^{XX}_2$, —$R^{XM}$
—C(=O)OH, —C(=O)$OR^{XX}$, —OC(=O)$R^{XX}$,
—C(=O)$NH_2$, —C(=O)$NHR^{XX}$, —C(=O)$NR^{XX}_2$,
—C(=O)$R^{XM}$,
—NHC(=O)$R^{XX}$, —$NR^{XN}$C(=O)$R^{XX}$,
—C(=O)$R^{XX}$
—S(=O)$NH_2$, —S(=O)$NHR^{XX}$, —S(=O)$NR^{XX}_2$,
—S(=O)$R^{XM}$,
—$S(=O)_2NH_2$, —$S(=O)_2NHR^{XX}$, —$S(=O)_2NR^{XX}_2$,
—$S(=O)_2R^{XM}$,
—NHS(=O)$R^{XX}$, —$NR^{XN}$S(=O)$R^{XX}$,
—$NHS(=O)_2R^{XX}$, —$NR^{XN}S(=O)_2R^{XX}$,
—S(=O)$R^{XX}$, —$S(=O)_2R^{XX}$,
—$SR^{XX}$, —CN, and —$NO_2$.

(32) A compound according to any one of (1) to (29), wherein each —$R^X$, if present, is independently selected from:
—$R^{XX}$,
—F, —Cl, —Br, —I,
—OH, —$OR^{XX}$,
—$CF_3$, —$OCF_3$,
—$NH_2$, —$NHR^{XX}$, —$NR^{XX}_2$, —$R^{XM}$,
—C(=O)OH, —C(=O)$OR^{XX}$, —OC(=O)$R^{XX}$,
—C(=O)$NH_2$, —C(=O)$NHR^{XX}$, —C(=O)$NR^{XX}_2$,
—C(=O)$R^{XM}$,
—NHC(=O)$R^{XX}$, —$NR^{XN}$C(=O)$R^{XX}$,
—C(=O)$R^{XX}$,
—S(=O)$NH_2$, —S(=O)$NHR^{XX}$, —S(=O)$NR^{XX}_2$,
—S(=O)$R^{XM}$,
—$S(=O)_2NH_2$, —$S(=O)_2NHR^{XX}$, —$S(=O)_2NR^{XX}_2$,
—$S(=O)_2R^{XM}$,
—NHS(=O)$R^{XX}$, —$NR^{XN}$S(=O)$R^{XX}$,
—$NHS(=O)_2R^{XX}$, —$NR^{XN}S(=O)_2R^{XX}$,
—S(=O)$R^{XX}$, —$S(=O)_2R^{XX}$,
—$SR^{XX}$, —CN, and —$NO_2$.

(33) A compound according to any one of (1) to (29), wherein each —$R^X$, if present, is independently selected from:
—$R^{XX}$, —$R^{XXU}$, —$R^{XXV}$,
—F, —Cl, —Br, —I,
—OH, —$OR^{XX}$,
—$CF_3$, —$OCF_3$, —NH$_2$, —NHR$^{XX}$, —NR$^{XX}_2$, —R$^{XM}$,
—C(=O)OH, —C(=O)OR$^{XX}$, —OC(=O)R$^{XX}$,
—SR$^{XX}$, —CN, and —NO$_2$.

(34) A compound according to any one of (1) to (29), wherein each —R$^X$, if present, is independently selected from:
—R$^{XX}$,
—F, —Cl, —Br, —I,
—OH, —OR$^{XX}$,
—CF$_3$, —OCF$_3$,
—NH$_2$, —NHR$^{XX}$, —NR$^{XX}_2$, —R$^{XM}$, and
—CN.

(35) A compound according to any one of (1) to (29), wherein each —R$^X$, if present, is independently selected from:
—R$^{XX}$,
—F, —Cl, —Br, —I,
—OH, —OR$^{XX}$,
—CF$_3$, and —OCF$_3$.

The Group -L$^{XX}$-

(36) A compound according to any one of (1) to (35), wherein each -L$^{XX}$-, if present, is independently —CH$_2$CH$_2$CH$_2$—, —CH$_2$CH$_2$—, —CH(CH$_3$)CH$_2$—, —CH(CH$_3$)—, or —CH$_2$—.

(37) A compound according to any one of (1) to (35), wherein each -L$^{XX}$-, if present, is independently —CH$_2$CH$_2$ or —CH$_2$—.

(38) A compound according to any one of (1) to (35), wherein each -L$^{XX}$-, if present, is —CH$_2$—.

The Group —R$^{XX}$

(39) A compound according to any one of (1) to (38), wherein each —R$^{XX}$, if present, is linear or branched saturated C$_{1-4}$alkyl.

(40) A compound according to any one of (1) to (38), wherein each —R$^{XX}$, if present, is -Me.

The Group —R$^{XXU}$

(41) A compound according to any one of (1) to (40), wherein each —R$^{XXU}$, if present, is independently —CH=CH$_2$ or —CH$_2$—CH=CH$_2$.

(42) A compound according to any one of (1) to (40), wherein each —R$^{XXU}$, if present, is —CH=CH$_2$.

The Group —R$^{XXV}$

(43) A compound according to any one of (1) to (42), wherein each —R$^{XXV}$, if present, is independently —CH≡CH or —CH$_2$—C≡CH.

(44) A compound according to any one of (1) to (42), wherein each —R$^{XXV}$, if present, is —CH≡CH.

The Group —R$^{XXH}$

(45) A compound according to any one of (1) to (44), wherein each —R$^{XXH}$, if present, is C$_{5-6}$heteroaryl, and is optionally substituted with one or more substituents —R$^{XMM}$.

(46) A compound according to any one of (1) to (44), wherein each —R$^{XXH}$, if present, is independently furanyl, thienyl, pyrrolyl, pyrazolyl, imidazolyl, oxazolyl, isoxazolyl, thiazolyl, isothiazolyl, pyridyl, pyridazinyl, pyrimidinyl, or pyrazinyl, and is optionally substituted with one or more substituents —R$^{XMM}$.

(47) A compound according to any one of (1) to (44), wherein each —R$^{XXH}$, if present, is independently pyrazolyl, and is optionally substituted with one or more substituents —R$^{XMM}$.

The Group —R$^{XN}$

(48) A compound according to any one of (1) to (47), wherein each —R$^{XN}$, if present, is independently -Me, -Et, -nPr, or -iPr.

(49) A compound according to any one of (1) to (47), wherein each —R$^{XN}$, if present, is -Me.

The Group —R$^{XM}$

(50) A compound according to any one of (1) to (49), wherein each —R$^{XM}$, if present, is independently pyrrolidino, piperidino, piperazino, or morpholino, and is: optionally substituted with one or more groups selected from:
—R$^{XMM}$, —C(=O)R$^{XMM}$, —C(=O)OR$^{XMM}$, and —S(=O)$_2$R$^{XMM}$.

(51) A compound according to any one of (1) to (49), wherein each —R$^{XM}$, if present, is independently pyrrolidino, piperidino, piperazino, or morpholino.

The Group —R$^{XMM}$

(52) A compound according to any one of (1) to (51), wherein each —R$^{XMM}$, if present, is linear or branched saturated C$_{1-4}$alkyl.

(53) A compound according to any one of (1) to (51), wherein each —R$^{XMM}$, if present, is -Me.

The Group —R$^1$

(54) A compound according to any one of (1) to (53), wherein —R$^1$ is —R$^{11}$.

(55) A compound according to any one of (1) to (53), wherein —R$^1$ is —H.

The Group —R$^{11}$

(56) A compound according to any one of (1) to (55), wherein —R$^{11}$, if present, is —R$^{11A}$.

(57) A compound according to any one of (1) to (55), wherein —R$^{11}$, if present, is —R$^{11B}$.

The Group —R$^{11A}$

(58) A compound according to any one of (1) to (57), wherein —R$^{11A}$, if present, is independently —R$^{41}$, —R$^{44}$, -L$^A$-R$^{44}$, or -L$^A$-R$^{45}$.

(59) A compound according to any one of (1) to (57), wherein —R$^{11A}$, if present, is independently —R$^{41}$, -L$^A$-R$^{44}$, or -L$^A$-R$^{45}$.

(60) A compound according to any one of (1) to (57), wherein —R$^{11A}$, if present, is independently —R$^{41}$ or -L$^A$-R$^{44}$.

(61) A compound according to any one of (1) to (57), wherein —R$^{11A}$, if present, is —R$^{41}$.

(62) A compound according to any one of (1) to (57), wherein —R$^{11A}$, if present, is -L$^A$-R$^{44}$.

(63) A compound according to any one of (1) to (57), wherein —R$^{11A}$, if present, is -L$^A$-R$^{45}$.

The Group —R$^{41}$

(64) A compound according to any one of (1) to (63), wherein each —R$^{41}$, if present, is independently -Me, -Et, -nPr, -iPr, -nBu, -iBu, -sBu, or -tBu; and is optionally substituted with one or more groups —R$^{AA2}$.

(65) A compound according to any one of (1) to (63), wherein each —R$^{41}$, if present, is -iBu; and is optionally substituted with one or more groups —R$^{AA2}$.

(66) A compound according to any one of (1) to (63), wherein each —R$^{41}$, if present, is -iPr; and is optionally substituted with one or more groups —R$^{AA2}$.

(67) A compound according to any one of (1) to (63), wherein each —R$^{41}$, if present, is -Me; and is optionally substituted with one or more groups —R$^{AA2}$.

(68) A compound according to any one of (1) to (63), wherein each —R$^{41}$, if present, is independently -Me, -Et, -nPr, -iPr, -nBu, -iBu, -sBu, or -tBu.

(69) A compound according to any one of (1) to (63), wherein each —R$^{41}$, if present, is -iBu.

(70) A compound according to any one of (1) to (63), wherein each —R$^{41}$, if present, is -iPr.

(71) A compound according to any one of (1) to (63), wherein each —$R^{41}$, if present, is -Me.

The Group —$R^{42}$

(72) A compound according to any one of (1) to (71), wherein each —$R^{42}$, if present, is independently cyclopropyl, cyclobutyl, cyclopentyl, or cyclohexyl, and is optionally substituted with one or more groups —$R^{41}$ and one or more groups —$R^{AA2}$.

(73) A compound according to any one of (1) to (71), wherein each —$R^{42}$, if present, is independently cyclopropyl, cyclobutyl, cyclopentyl, or cyclohexyl.

The Group —$R^{43}$

(74) A compound according to any one of (1) to (73), wherein each —$R^{43}$, if present, is independently oxetanyl, tetrahydrofuranyl, tetrahydropyranyl, dioxanyl, azetidinyl, pyrrolidinyl, piperidinyl, piperazinyl, morpholinyl, azepanyl, or diazepanyl, and is optionally substituted with one or more groups —$R^{41}$ and one or more groups —$R^{AA2}$.

(75) A compound according to any one of (1) to (73), wherein each —$R^{43}$, if present, is independently tetrahydrofuranyl, tetrahydropyranyl, dioxanyl, pyrrolidinyl, piperidinyl, piperazinyl, or morpholinyl, and is optionally substituted with one or more groups —$R^{AA1}$ and one or more groups —$R^{AA2}$.

(76) A compound according to any one of (1) to (73), wherein each —$R^{43}$, if present, is independently tetrahydrofuranyl, tetrahydropyranyl, or dioxanyl, and is optionally substituted with one or more groups —$R^{41}$ and one or more groups —$R^{AA2}$.

(77) A compound according to any one of (1) to (73), wherein each —$R^{43}$, if present, is independently pyrrolidinyl, piperidinyl, piperazinyl, or morpholinyl, and is optionally substituted with one or more groups —$R^{41}$ and one or more groups —$R^{AA2}$.

(78) A compound according to any one of (1) to (73), wherein each —$R^{43}$, if present, is independently tetrahydrofuranyl, tetrahydropyranyl, dioxanyl, pyrrolidinyl, piperidinyl, piperazinyl, or morpholinyl.

(79) A compound according to any one of (1) to (73), wherein each —$R^{43}$, if present, is independently tetrahydrofuranyl, tetrahydropyranyl, or dioxanyl.

(80) A compound according to any one of (1) to (73), wherein each —$R^{43}$, if present, is independently pyrrolidinyl, piperidinyl, piperazinyl, or morpholinyl.

The Group —$R^{44}$

(81) A compound according to any one of (1) to (80), wherein each —$R^{44}$, if present, is phenyl, and is optionally substituted with one or more groups —$R^{AA1}$ and one or more groups —$R^{AA2}$.

(82) A compound according to any one of (1) to (80), wherein each —$R^{44}$, if present, is phenyl.

The Group —$R^{45}$

(83) A compound according to any one of (1) to (82), wherein each —$R^{45}$, if present, is independently furanyl, thienyl, pyrrolyl, imidazolyl, oxazolyl, thiazolyl, pyrazolyl, isoxazolyl, isothiazolyl, pyridyl, pyridazinyl, pyrimidinyl, pyrazinyl, indolyl, benzoimidazolyl, indazolyl, benzofuranyl, benzothienyl, benzooxazolyl, benzothiazolyl, benzoisoxazolyl, benzoisothiazolyl, quinolinyl, isoquinolinyl, cinnolinyl, quinoxalinyl, quinazolinyl, or phthalazinyl, and is optionally substituted with one or more groups —$R^{AA1}$ and one or more groups —$R^{AA2}$.

(84) A compound according to any one of (1) to (82), wherein each —$R^{45}$, if present, is independently furanyl, thienyl, pyrrolyl, imidazolyl, oxazolyl, thiazolyl, pyrazolyl, isoxazolyl, isothiazolyl, pyridyl, pyridazinyl, pyrimidinyl, or pyrazinyl, and is optionally substituted with one or more groups —$R^{AA1}$ and one or more groups —$R^{AA2}$.

(85) A compound according to any one of (1) to (82), wherein each —$R^{45}$, if present, is independently furanyl, thienyl, pyrrolyl, imidazolyl, oxazolyl, thiazolyl, pyrazolyl, isoxazolyl, or isothiazolyl, and is optionally substituted with one or more groups —$R^{AA1}$ and one or more groups —$R^{AA2}$.

(86) A compound according to any one of (1) to (82), wherein each —$R^{45}$, if present, is independently pyridyl, pyridazinyl, pyrimidinyl, or pyrazinyl, and is optionally substituted with one or more groups —$R^{AA1}$ and one or more groups —$R^{AA2}$.

(87) A compound according to any one of (1) to (82), wherein each —$R^{45}$, if present, is independently imidazolyl or indolyl, and is optionally substituted with one or more groups —$R^{AA1}$ and one or more groups —$R^{AA2}$.

(88) A compound according to any one of (1) to (82), wherein each —$R^{45}$, if present, is independently furanyl, thienyl, pyrrolyl, imidazolyl, oxazolyl, thiazolyl, pyrazolyl, isoxazolyl, isothiazolyl, pyridyl, pyridazinyl, pyrimidinyl, or pyrazinyl.

(89) A compound according to any one of (1) to (82), wherein each —$R^{45}$, if present, is independently furanyl, thienyl, pyrrolyl, imidazolyl, oxazolyl, thiazolyl, pyrazolyl, isoxazolyl, or isothiazolyl.

(90) A compound according to any one of (1) to (82), wherein each —$R^{45}$, if present, is independently pyridyl, pyridazinyl, pyrimidinyl, or pyrazinyl.

(91) A compound according to any one of (1) to (82), wherein each —$R^{45}$, if present, is independently imidazolyl or indolyl.

The Group -$L^A$-

(92) A compound according to any one of (1) to (91), wherein each -$L^A$-, if present, is independently —$CH_2CH_2CH_2$—, —$CH_2CH_2$—, —$CH(CH_3)CH_2$—, —$CH(CH_3)$—, or —$CH_2$—.

(93) A compound according to any one of (1) to (91), wherein each -$L^A$-, if present, is independently —$CH_2CH_2$ or —$CH_2$—.

(94) A compound according to any one of (1) to (91), wherein each -$L^A$-, if present, is —$CH_2$—.

The Group —$R^{AA1}$

(95) A compound according to any one of (1) to (94), wherein each —$R^{AA1}$, if present, is —$R^{AA}$.

The Group —$R^{AA2}$

(96) A compound according to any one of (1) to (95), wherein each —$R^{AA2}$, if present, is independently selected from:

—F, —Cl, —Br, —I,
—OH, —$OR^{AA}$,
—$OCF_3$,
—$NH_2$, —$NHR^{AA}$, —$NR^{AA}_2$, —$R^{AM}$,
—C(=O)OH, —C(=O)$OR^{AA}$, —OC(=O)$R^{AA}$,
—C(=O)$NH_2$, —C(=O)$NHR^{AA}$, —C(=O)$NR^{AA2}$,
—C(=O)$R^{AM}$,
—NHC(=O)$R^{AA}$, —$NR^{AN}$C(=O)$R^{AA}$,
—C(=O)$R^{AA}$,
—S(=O)$NH_2$, —S(=O)$NHR^{AA}$, —S(=O)$NR^{AA2}$,
—S(=O)$R^{AM}$,
—S(=O)$_2NH_2$, —S(=O)$_2NHR^{AA}$, —S(=O)$_2NR^{AA2}$,
—S(=O)$_2R^{AM}$,
—NHS(=O)$R^{AA}$, —$NR^{AN}$S(=O)$R^{AA}$,
—NHS(=O)$_2R^{AA}$, —$NR^{AN}$S(=O)$_2R^{AA}$,

—S(=O)R$^{AA}$, —S(=O)$_2$R$^{AA}$,
—SH, —SR$^{AA}$, —CN, and —NO$_2$.

(97) A compound according to any one of (1) to (95), wherein each —R$^{AA2}$, if present, is independently selected from:
—F, —Cl, —Br, —I,
—OH, —OR$^{AA}$,
—OCF$_3$,
—NH$_2$, —NHR$^{AA}$, —NR$^{AA}{}_2$, —R$^{AM}$, and
—CN.

(98) A compound according to any one of (1) to (95), wherein each —R$^{AA2}$, if present, is independently selected from:
—F, —Cl, —Br, —I,
—OH, —OR$^{AA}$, and
—OCF$_3$.

(99) A compound according to any one of (1) to (95), wherein each —R$^{AA2}$, if present, is independently selected from:
—OH, —OR$^{AA}$,
—NH$_2$, —NHR$^{AA}$, —NR$^{AA}{}_2$, —R$^{AM}$,
—C(=O)OH, —C(=O)OR$^{AA}$
—C(=O)NH$_2$, —C(=O)NHR$^{AA}$, —C(=O)NR$^{AA2}$,
—C(=O)R$^{AM}$,
—NHC(=NH)NH$_2$,
—SH, and —SR$^{AA}$.

(100) A compound according to any one of (1) to (95), wherein each —R$^{AA2}$, if present, is independently selected from:
—OH,
—NH$_2$,
—C(=O)OH,
—C(=O)NH$_2$,
—NHC(=NH)NH$_2$,
—SH, and —SMe.

The Group -L$^{AA}$-
(101) A compound according to any one of (1) to (100), wherein each -L$^{AA}$-, if present, is independently —CH$_2$CH$_2$CH$_2$—, —CH$_2$CH$_2$—, —CH(CH$_3$)CH$_2$—, —CH(CH$_3$)—, or —CH$_2$—.

(102) A compound according to any one of (1) to (100), wherein each -L$^{AA}$-, if present, is independently —CH$_2$CH$_2$ or —CH$_2$—.

The Group —R$^{AA}$
(103) A compound according to any one of (1) to (102), wherein each —R$^{AA}$, if present, is linear or branched saturated C$_{1-4}$alkyl.

(104) A compound according to any one of (1) to (102), wherein each —R$^{AA}$, if present, is -Me.

The Group —R$^{AN}$
(105) A compound according to any one of (1) to (104), wherein each —R$^{AN}$, if present, is independently -Me, -Et, -nPr, or -iPr.

(106) A compound according to any one of (1) to (104), wherein each —R$^{AN}$, if present, is -Me.

The Group —R$^{AM}$
(107) A compound according to any one of (1) to (106), wherein each —R$^{AM}$, if present, is independently pyrrolidino, piperidino, piperazino, or morpholino, and is: optionally substituted with one or more groups selected from:
—R$^{AMM}$, —C(=O)R$^{AMM}$, —C(=O)OR$^{AMM}$, and —S(=O)$_2$R$^{AMM}$.

(108) A compound according to any one of (1) to (106), wherein each —R$^{AM}$, if present, is independently pyrrolidino, piperidino, piperazino, or morpholino.

The Group —R$^{AMM}$
(109) A compound according to any one of (1) to (108), wherein each —R$^{AMM}$, if present, is linear or branched saturated C$_{1-4}$alkyl.

(110) A compound according to any one of (1) to (108), wherein each —R$^{AMM}$, if present, is -Me.

The Group —R$^{11A}$: Some Specific Groups
(111) A compound according to any one of (1) to (57), wherein —R$^{11A}$, if present, is independently selected from:
—CH$_3$ (e.g., as in alanine),
—CH$_2$CH$_3$ (e.g., as in isoleucine),
—CH$_2$CH(CH$_3$)$_2$ (e.g., as in leucine),
—CH$_2$CH$_2$—S—CH$_3$ (e.g., as in methionine),
—CH$_2$-(phenyl) (e.g., as in phenylalanine),
—CH$_2$-(1H-indol-3-yl) (e.g., as in tryptophan),
—CH(CH$_3$)$_2$ (e.g., as in valine),
—CH$_2$—C(=O)NH$_2$ (e.g., as in asparagine),
—CH$_2$—SH (e.g., as in cysteine),
—CH$_2$CH$_2$—C(=O)NH$_2$ (e.g., as in glutamine),
—CH$_2$—OH (e.g., as in serine),
—CH(OH)CH$_3$ (e.g., as in threonine),
—CH$_2$-(4-hydroxy-phenyl) (e.g., as in tyrosine),
—CH$_2$CH$_2$CH$_2$—NH—C(=NH)—NH$_2$ (e.g., as in arginine),
—CH$_2$-(1H-imidazol-4-yl) (e.g., as in histidine),
—CH$_2$CH$_2$CH$_2$CH$_2$—NH$_2$ (e.g., as in lysine),
—CH$_2$—C(=O)OH (e.g., as in aspartic acid), and
—CH$_2$CH$_2$—C(=O)OH (e.g., as in glutamic acid).

The Group —R$^{11B}$
(112) A compound according to any one of (1) to (111), wherein —R$^{11B}$, if present, is independently selected from:
—F, —Cl, —Br, —I,
—OH, —OR$^{BB}$,
—OCF$_3$,
—NH$_2$, —NHR$^{BB}$, —NR$^{BB}{}_2$, —R$^{BM}$,
—C(=O)OH, —C(=O)OR$^{BB}$, —OC(=O)R$^{BB}$,
—C(=O)NH$_2$, —C(=O)NHR$^{BB}$, —C(=O)NR$^{BB}{}_2$,
—C(=O)R$^{BM}$,
—NHC(=O)R$^{BB}$, —NR$^{BN}$C(=O)R$^{BB}$,
—C(=O)R$^{BB}$,
—S(=O)NH$_2$, —S(=O)NHR$^{BB}$, —S(=O)NR$^{BB}{}_2$,
—S(=O)R$^{BM}$,
—S(=O)$_2$NH$_2$, —S(=O)$_2$NHR$^{BB}$, —S(=O)$_2$NR$^{BB}{}_2$,
—S(=O)$_2$R$^{BM}$,
—NHS(=O)R$^{BB}$, —NR$^{BN}$S(=O)R$^{BB}$,
—NHS(=O)$_2$R$^{BB}$, —NR$^{BN}$S(=O)$_2$R$^{BB}$,
—S(=O)R$^{BB}$, —S(=O)$_2$R$^{BB}$,
—SR$^{BB}$, —CN, and —NO$_2$.

(113) A compound according to any one of (1) to (111), wherein each —R$^{11B}$, if present, is independently selected from:
—F, —Cl, —Br, —I,
—OH, —OR$^{BB}$,
—OCF$_3$,
—NH$_2$, —NHR$^{BB}$, —NR$^{BB}{}_2$, —R$^{BM}$, and
—CN.

(114) A compound according to any one of (1) to (111), wherein each —R$^{11B}$, if present, is independently selected from:
—F, —Cl, —Br, —I,
—OH, —OR$^{BB}$, and
—OCF$_3$.

The Group —R$^{BB}$
(115) A compound according to any one of (1) to (114), wherein each —R$^{BB}$, if present, is linear or branched saturated C$_{1-4}$alkyl.

(116) A compound according to any one of (1) to (114), wherein each —$R^{BB}$, if present, is -Me.

The Group —$R^{BN}$ (117) A compound according to any one of (1) to (116), wherein each —$R^{BN}$, if present, is independently -Me, -Et, -nPr, or -iPr.

(118) A compound according to any one of (1) to (116), wherein each —$R^{BN}$, if present, is -Me.

The Group —$R^{BM}$ (119) A compound according to any one of (1) to (118), wherein each —$R^{BM}$, if present, is independently pyrrolidino, piperidino, piperazino, or morpholino, and is: optionally substituted with one or more groups selected from:
—$R^{BMM}$, —C(=O)$R^{BMM}$, —C(=O)O$R^{BMM}$, and —S(=O)$_2R^{BMM}$.

(120) A compound according to any one of (1) to (118), wherein each —$R^{BM}$, if present, is independently pyrrolidino, piperidino, piperazino, or morpholino.

The Group —$R^{BMM}$ (121) A compound according to any one of (1) to (120), wherein each —$R^{BMM}$, if present, is linear or branched saturated $C_{1-4}$alkyl.

(122) A compound according to any one of (1) to (120), wherein each —$R^{BMM}$, if present, is -Me.

The Group —$R^2$ (123) A compound according to any one of (1) to (122), wherein —$R^2$ is —H.

(124) A compound according to any one of (1) to (122), wherein —$R^2$ is —$R^{22}$.

The Group —$R^{22}$ (125) A compound according to any one of (1) to (124), wherein —$R^{22}$, if present, is —$R^{22C}$.

(126) A compound according to any one of (1) to (124), wherein —$R^{22}$, if present, is —$R^{22D}$.

The Group —$R^{22C}$ (127) A compound according to any one of (1) to (126), wherein —$R^{22C}$, if present, is independently —$R^{C1}$, —$R^4$, -$L^C$-$R^{C4}$, or -$L^C$-$R^{C5}$.

(128) A compound according to any one of (1) to (126), wherein —$R^{22C}$, if present, is independently —$R^{C1}$, -$L^C$-$R^{C4}$, or -$L^C$-$R^{C5}$.

(129) A compound according to any one of (1) to (126), wherein —$R^{22C}$, if present, is independently —$R^{C1}$ or -$L^C$-$R^{C4}$.

(130) A compound according to any one of (1) to (126), wherein —$R^{11A}$, if present, is —$R^{C1}$.

(131) A compound according to any one of (1) to (126), wherein —$R^{11A}$, if present, is -$L^C$-$R^{C4}$.

(132) A compound according to any one of (1) to (126), wherein —$R^{11A}$, if present, is -$L^C$-$R^{C5}$.

The Group —$R^{C1}$ (132) A compound according to any one of (1) to (132), wherein each —$R^{C1}$, if present, is independently -Me, -Et, -nPr, -iPr, -nBu, -iBu, -sBu, or -tBu; and is optionally substituted with one or more groups —$R^{CC2}$.

(133) A compound according to any one of (1) to (132), wherein each —$R^{C1}$, if present, is independently -Me; and is optionally substituted with one or more groups —$R^{CC2}$.

(134) A compound according to any one of (1) to (132), wherein each —$R^{C1}$, if present, is independently -iPr; and is optionally substituted with one or more groups —$R^{CC2}$.

(135) A compound according to any one of (1) to (132), wherein each —$R^{C1}$, if present, is independently -iBu; and is optionally substituted with one or more groups —$R^{CC2}$.

(136) A compound according to any one of (1) to (132), wherein each —$R^{C1}$, if present, is independently -Me, -Et, -nPr, -iPr, -nBu, -iBu, -sBu, or -tBu.

(137) A compound according to any one of (1) to (132), wherein each —$R^{C1}$, if present, is independently -Me.

(138) A compound according to any one of (1) to (132), wherein each —$R^{C1}$, if present, is independently -iPr.

(139) A compound according to any one of (1) to (132), wherein each —$R^{C1}$, if present, is independently -iBu.

The Group —$R^{C2}$ (140) A compound according to any one of (1) to (139), wherein each —$R^{C2}$, if present, is independently cyclopropyl, cyclobutyl, cyclopentyl, or cyclohexyl, and is optionally substituted with one or more groups —$R^{CC1}$ and one or more groups —$R^{CC2}$.

(141) A compound according to any one of (1) to (139), wherein each —$R^{C2}$, if present, is independently cyclopropyl, cyclobutyl, cyclopentyl, or cyclohexyl.

The Group —$R^{C3}$ (142) A compound according to any one of (1) to (141), wherein each —$R^{C3}$, if present, is independently oxetanyl, tetrahydrofuranyl, tetrahydropyranyl, dioxanyl, azetidinyl, pyrrolidinyl, piperidinyl, piperazinyl, morpholinyl, azepanyl, or diazepanyl, and is optionally substituted with one or more groups —$R^{CC1}$ and one or more groups —$R^{CC2}$.

(143) A compound according to any one of (1) to (141), wherein each —$R^{C3}$, if present, is independently tetrahydrofuranyl, tetrahydropyranyl, dioxanyl, pyrrolidinyl, piperidinyl, piperazinyl, or morpholinyl, and is optionally substituted with one or more groups —$R^{CC1}$ and one or more groups —$R^{CC2}$.

(144) A compound according to any one of (1) to (141), wherein each —$R^{C3}$, if present, is independently tetrahydrofuranyl, tetrahydropyranyl, or dioxanyl, and is optionally substituted with one or more groups —$R^{CC1}$ and one or more groups —$R^{CC2}$.

(145) A compound according to any one of (1) to (141), wherein each —$R^{C3}$, if present, is independently pyrrolidinyl, piperidinyl, piperazinyl, or morpholinyl, and is optionally substituted with one or more groups —$R^{CC1}$ and one or more groups —$R^{CC2}$.

(146) A compound according to any one of (1) to (141), wherein each —$R^{C3}$, if present, is independently tetrahydrofuranyl, tetrahydropyranyl, dioxanyl, pyrrolidinyl, piperidinyl, piperazinyl, or morpholinyl.

(147) A compound according to any one of (1) to (141), wherein each —$R^{C3}$, if present, is independently tetrahydrofuranyl, tetrahydropyranyl, or dioxanyl.

(148) A compound according to any one of (1) to (141), wherein each —$R^{C3}$, if present, is independently pyrrolidinyl, piperidinyl, piperazinyl, or morpholinyl.

The Group —$R^{C4}$ (149) A compound according to any one of (1) to (148), wherein each —$R^{C4}$, if present, is phenyl, and is optionally substituted with one or more groups —$R^{CC1}$ and one or more groups —$R^{CC2}$.

(150) A compound according to any one of (1) to (148), wherein each —$R^{C4}$, if present, is phenyl.

The Group —$R^{C5}$ (151) A compound according to any one of (1) to (150), wherein each —$R^{C5}$, if present, is independently furanyl, thienyl, pyrrolyl, imidazolyl, oxazolyl, thiazolyl, pyrazolyl, isoxazolyl, isothiazolyl, pyridyl, pyridazinyl, pyrimidinyl, pyrazinyl, indolyl, benzoimidazolyl, indazolyl, benzofuranyl, benzothienyl, benzooxazolyl, benzothiazolyl, benzoisoxazolyl, benzoisothiazolyl, quinolinyl, isoquinolinyl, cinnolinyl, quinoxalinyl, quinazolinyl, or phthalazinyl, and is optionally substituted with one or more groups —$R^{CC1}$ and one or more groups —$R^{CC2}$.

(152) A compound according to any one of (1) to (150), wherein each —$R^{C5}$, if present, is independently furanyl, thienyl, pyrrolyl, imidazolyl, oxazolyl, thiazolyl, pyrazolyl, isoxazolyl, isothiazolyl, pyridyl, pyridazinyl, pyrimidinyl, or pyrazinyl, and is optionally substituted with one or more groups —$R^{CC1}$ and one or more groups —$R^{CC2}$.

(153) A compound according to any one of (1) to (150), wherein each —$R^{C5}$, if present, is independently furanyl, thienyl, pyrrolyl, imidazolyl, oxazolyl, thiazolyl, pyrazolyl, isoxazolyl, or isothiazolyl, and is optionally substituted with one or more groups —$R^{CC1}$ and one or more groups —$R^{CC2}$.

(154) A compound according to any one of (1) to (150), wherein each —$R^{C5}$, if present, is independently pyridyl, pyridazinyl, pyrimidinyl, or pyrazinyl, and is optionally substituted with one or more groups —$R^{CC1}$ and one or more groups —$R^{CC2}$.

(155) A compound according to any one of (1) to (150), wherein each —$R^{C5}$, if present, is independently imidazolyl or indolyl, and is optionally substituted with one or more groups —$R^{CC1}$ and one or more groups —$R^{CC2}$.

(156) A compound according to any one of (1) to (150), wherein each —$R^{C5}$, if present, is independently furanyl, thienyl, pyrrolyl, imidazolyl, oxazolyl, thiazolyl, pyrazolyl, isoxazolyl, 156, pyridyl, pyridazinyl, pyrimidinyl, or pyrazinyl.

(157) A compound according to any one of (1) to (150), wherein each —$R^{C5}$, if present, is independently furanyl, thienyl, pyrrolyl, imidazolyl, oxazolyl, thiazolyl, pyrazolyl, isoxazolyl, or isothiazolyl.

(158) A compound according to any one of (1) to (150), wherein each —$R^{C5}$, if present, is independently pyridyl, pyridazinyl, pyrimidinyl, or pyrazinyl.

(159) A compound according to any one of (1) to (150), wherein each —$R^{C5}$, if present, is independently imidazolyl or indolyl.

The Group -$L^C$-

(160) A compound according to any one of (1) to (159), wherein each -$L^C$-, if present, is independently —$CH_2CH_2CH_2$—, —$CH_2CH_2$—, —$CH(CH_3)CH_2$—, —$CH(CH_3)$—, or —$CH_2$—.

(161) A compound according to any one of (1) to (159), wherein each -$L^C$-, if present, is independently —$CH_2CH_2$ or —$CH_2$—.

(162) A compound according to any one of (1) to (159), wherein each -$L^C$-, if present, is —$CH_2$—.

The Group —$R^{CC1}$ (163) A compound according to any one of (1) to (162), wherein each —$R^{CC1}$, if present, is —$R^{CC}$.

The Group —$R^{CC2}$ (164) A compound according to any one of (1) to (163), wherein each —$R^{CC2}$, if present, is independently selected from:
—F, —Cl, —Br, —I,
—OH, —$OR^{CC}$,
—$OCF_3$,
—$NH_2$, —$NHR^{CC}$, —$NR^{CC}_2$, —$R^{CM}$,
—C(=O)OH, —C(=O)$OR^{CC}$, —OC(=O)$R^{CC}$,
—C(=O)$NH_2$, —C(=O)$NHR^{CC}$, —C(=O)$NR^{CC}_2$,
—C(=O)$R^{CM}$,
—NHC(=O)$R^{CC}$, —$NR^{CN}$C(=O)$R^{CC}$,
—C(=O)$R^{CC}$,
—S(=O)$NH_2$, —S(=O)$NHR^{CC}$, —S(=O)$NR^{CC}_2$,
—S(=O)$R^{CM}$,
—S(=O)$_2NH_2$, —S(=O)$_2NHR^{CC}$, —S(=O)$_2NR^{CC}_2$,
—S(=O)$_2R^{CM}$,
—NHS(=O)$R^{CC}$, —$NR^{CN}$S(=O)$R^{CC}$,
—NHS(=O)$_2R^{CC}$, —$NR^{CN}$S(=O)$_2R^{CC}$,
—S(=O)$R^{CC}$, —S(=O)$_2R^{CC}$,
—SH, —$SR^{CC}$, —CN, and —$NO_2$.

(165) A compound according to any one of (1) to (163), wherein each —$R^{CC2}$, if present, is independently selected from:
—F, —Cl, —Br, —I,
—OH, —$OR^{CC}$,
—$OCF_3$,
—$NH_2$, —$NHR^{CC}$, —$NR^{CC}_2$, —$R^{CM}$, and
—CN.

(166) A compound according to any one of (1) to (163), wherein each —$R^{CC2}$, if present, is independently selected from:
—F, —Cl, —Br, —I,
—OH, —$OR^{CC}$, and
—$OCF_3$.

(167) A compound according to any one of (1) to (163), wherein each —$R^{CC2}$, if present, is independently selected from:
—OH, —$OR^{CC}$,
—$NH_2$, —$NHR^{CC}$, —$NR^{CC}_2$, —$R^{CM}$,
—C(=O)OH, —C(=O)$OR^{CC}$,
—C(=O)$NH_2$, —C(=O)$NHR^{CC}$, —C(=O)$NR^{CC}_2$,
—C(=O)$R^{CM}$,
—NHC(=NH)$NH_2$,
—SH, and —$SR^{CC}$ (168) A compound according to any one of (1) to (163), wherein each —$R^{CC2}$, if present, is independently selected from:
—OH,
—$NH_2$,
—C(=O)OH,
—C(=O)$NH_2$,
—NHC(=NH)$NH_2$,
—SH, and —SMe.

The Group -$L^{CC}$-

(169) A compound according to any one of (1) to (168), wherein each -$L^{CC}$-, if present, is independently —$CH_2CH_2CH_2$—, —$CH_2CH_2$—, —$CH(CH_3)CH_2$—, —$CH(CH_3)$—, or —$CH_2$—.

(170) A compound according to any one of (1) to (168), wherein each -$L^{CC}$-, if present, is independently —$CH_2CH_2$ or —$CH_2$—.

(171) A compound according to any one of (1) to (168), wherein each -$L^{CC}$-, if present, is —$CH_2$—.

The Group —$R^{CC}$ (172) A compound according to any one of (1) to (171), wherein each —$R^{CC}$, if present, is linear or branched saturated $C_{1-4}$alkyl.

(173) A compound according to any one of (1) to (171), wherein each —$R^{CC}$, if present, is -Me.

The Group —$R^{CN}$ (174) A compound according to any one of (1) to (173), wherein each —$R^{CN}$, if present, is independently -Me, -Et, -nPr, or -iPr.

(175) A compound according to any one of (1) to (173), wherein each —R$^{CN}$, if present, is -Me.

The Group —R$^{CM}$ (176) A compound according to any one of (1) to (175), wherein each —R$^{CM}$, if present, is independently pyrrolidino, piperidino, piperazino, or morpholino, and is: optionally substituted with one or more groups selected from:
—R$^{CMM}$, —C(=O)R$^{CMM}$, —C(=O)OR$^{CMM}$, and —S(=O)$_2$R$^{CMM}$.

(177) A compound according to any one of (1) to (175), wherein each —R$^{CM}$, if present, is independently pyrrolidino, piperidino, piperazino, or morpholino.

The Group —R$^{CMM}$ (178) A compound according to any one of (1) to (177), wherein each —R$^{CMM}$, if present, is linear or branched saturated C$_{1-4}$alkyl.

(179) A compound according to any one of (1) to (177), wherein each —R$^{CMM}$, if present, is -Me.

The Group —R$^{22C}$: Some Specific Groups (180) A compound according to any one of (1) to (126), wherein —R$^{22C}$, if present, is independently selected from:
—CH$_3$ (e.g., as in alanine),
—CH$_2$CH$_3$ (e.g., as in isoleucine),
—CH$_2$CH(CH$_3$)$_2$ (e.g., as in leucine),
—CH$_2$CH$_2$—S—CH$_3$ (e.g., as in methionine),
—CH$_2$-(phenyl) (e.g., as in phenylalanine),
—CH$_2$-(1H-indol-3-yl) (e.g., as in tryptophan),
—CH(CH$_3$)$_2$ (e.g., as in valine),
—CH$_2$—C(=O)NH$_2$ (e.g., as in asparagine),
—CH$_2$—SH (e.g., as in cysteine),
—CH$_2$CH$_2$—C(=O)NH$_2$ (e.g., as in glutamine),
—CH$_2$—OH (e.g., as in serine),
—CH(OH)CH$_3$ (e.g., as in threonine),
—CH$_2$-(4-hydroxy-phenyl) (e.g., as in tyrosine),
—CH$_2$CH$_2$CH$_2$—NH—C(=NH)—NH$_2$ (e.g., as in arginine),
—CH$_2$-(1H-imidazol-4-yl) (e.g., as in histidine),
—CH$_2$CH$_2$CH$_2$CH$_2$—NH$_2$ (e.g., as in lysine),
—CH$_2$—C(=O)OH (e.g., as in aspartic acid), and
—CH$_2$CH$_2$—C(=O)OH (e.g., as in glutamic acid).

The Group —R$^{22D}$ (181) A compound according to any one of (1) to (180), wherein —R$^{22D}$, if present, is independently selected from:
—F, —Cl, —Br, —I,
—OH, —OR$^{DD}$,
—OCF$_3$,
—NH$_2$, —NHR$^{DD}$, —NR$^{DD}$$_2$, —R$^{DM}$,
—C(=O)OH, —C(=O)OR$^{DD}$, —OC(=O)R$^{DD}$,
—C(=O)NH$_2$, —C(=O)NHR$^{DD}$, —C(=O)NR$^{DD}$$_2$,
—C(=O)R$^{DM}$,
—NHC(=O)R$^{DD}$, —NR$^{DN}$C(=O)R$^{DD}$,
—C(=O)R$^{DD}$,
—S(=O)NH$_2$, —S(=O)NHR$^{DD}$, —S(=O)NR$^{DD}$$_2$,
—S(=O)R$^{DM}$,
—S(=O)$_2$NH$_2$, —S(=O)$_2$NHR$^{DD}$, —S(=O)$_2$NR$^{DD}$$_2$, —S(=O)$_2$R$^{DM}$,
—NHS(=O)R$^{DD}$, —NR$^{DN}$S(=O)R$^{DD}$,
—NHS(=O)$_2$R$^{DD}$, —NR$^{DN}$S(=O)$_2$R$^{DD}$,
—S(=O)R$^{DD}$, —S(=O)$_2$R$^{DD}$,
—SR$^{DD}$, —CN, and —NO$_2$.

(182) A compound according to any one of (1) to (180), wherein each —R$^{22D}$, if present, is independently selected from:
—F, —Cl, —Br, —I,
—OH, —OR$^{DD}$,
—OCF$_3$,
—NH$_2$, —NHR$^{DD}$, —NR$^{DD}$$_2$, —R$^{DM}$, and
—CN.

(183) A compound according to any one of (1) to (180), wherein each —R$^{22D}$, if present, is independently selected from:
—F, —Cl, —Br, —I,
—OH, —OR$^{DD}$, and
—OCF$_3$.

The Group —R$^{DD}$ (184) A compound according to any one of (1) to (183), wherein each —R$^{DD}$, if present, is linear or branched saturated C$_{1-4}$alkyl.

(185) A compound according to any one of (1) to (183), wherein each —R$^{DD}$, if present, is -Me.

The Group —R$^{DN}$ (186) A compound according to any one of (1) to (185), wherein each —R$^{DN}$, if present, is independently -Me, -Et, -nPr, or -iPr.

(187) A compound according to any one of (1) to (185), wherein each —R$^{DN}$, if present, is -Me.

The Group —R$^{DM}$ (188) A compound according to any one of (1) to (187), wherein each —R$^{DM}$, if present, is independently pyrrolidino, piperidino, piperazino, or morpholino, and is: optionally substituted with one or more groups selected from:
—R$^{DMM}$, —C(=O)R$^{DMM}$, —C(=O)OR$^{DMM}$, and —S(=O)$_2$R$^{DMM}$.

(189) A compound according to any one of (1) to (187), wherein each —R$^{DM}$, if present, is independently pyrrolidino, piperidino, piperazino, or morpholino.

The Group —R$^{DMM}$ (190) A compound according to any one of (1) to (189), wherein each —R$^{DMM}$, if present, is linear or branched saturated C$_{1-4}$alkyl.

(191) A compound according to any one of (1) to (189), wherein each —R$^{DMM}$, if present, is -Me.

Specific Compounds (192) A compound according to (1), which is selected from compounds of the following formulae, and pharmaceutically acceptable salts, hydrates, and solvates thereof:

| Structure | Code |
|---|---|
| (phenyl-S(=O)-NH-C(=O)-CH(NH$_2$)-CH$_2$-CH(CH$_3$)$_2$) | ANASA-001 |
| (phenyl-S(=O)-NH-C(=O)-CH(NH$_2$)-CH$_2$-CH$_2$-CH$_3$) | ANASA-002 |
| (phenyl-S(=O)-NH-C(=O)-CH(NH$_2$)-CH(CH$_3$)-CH$_2$-CH$_3$) | ANASA-003 |

-continued
| Structure | Code |
|---|---|
| 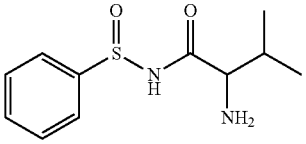 [SMILES: CC(C)C(N)C(=O)NS(=O)c1ccccc1] | ANASA-004 |
| 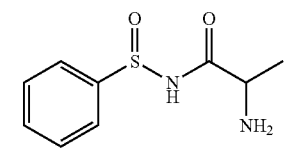 | ANASA-005 |
| 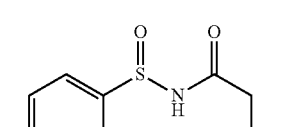 | ANASA-006 |
| 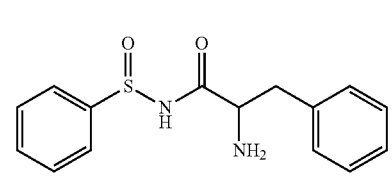 [SMILES: NC(Cc1ccccc1)C(=O)NS(=O)c1ccccc1] | ANASA-007 |
| 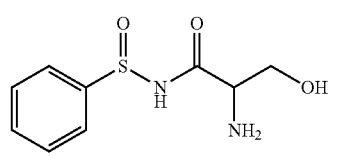 [SMILES: NC(CO)C(=O)NS(=O)c1ccccc1] | ANASA-008 |
| 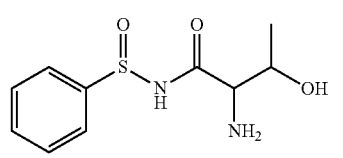 [SMILES: CC(O)C(N)C(=O)NS(=O)c1ccccc1] | ANASA-009 |
| 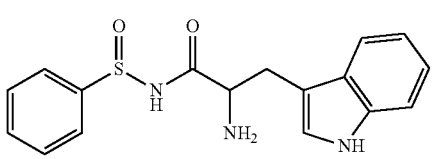 [SMILES: NC(Cc1c[nH]c2ccccc12)C(=O)NS(=O)c1ccccc1] | ANASA-010 |
| 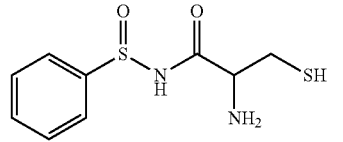 [SMILES: NC(CS)C(=O)NS(=O)c1ccccc1] | ANASA-011 |
| 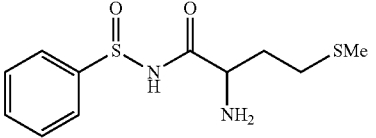 [SMILES: CSCCC(N)C(=O)NS(=O)c1ccccc1] | ANASA-012 |
-continued
| Structure | Code |
|---|---|
| 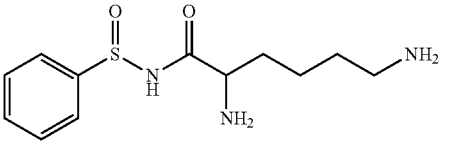 [SMILES: NCCCCC(N)C(=O)NS(=O)c1ccccc1] | ANASA-013 |
| 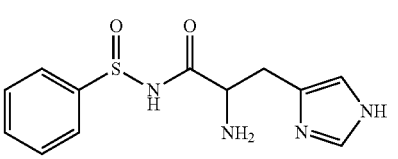 [SMILES: NC(Cc1c[nH]cn1)C(=O)NS(=O)c1ccccc1] | ANASA-014 |
| 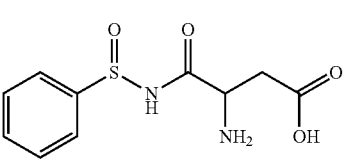 [SMILES: NC(CC(=O)O)C(=O)NS(=O)c1ccccc1] | ANASA-015 |
| 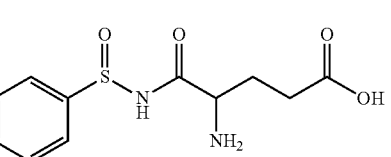 | ANASA-016 |
| 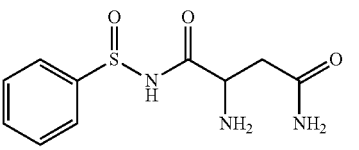 [SMILES: NC(=O)CC(N)C(=O)NS(=O)c1ccccc1] | ANASA-017 |
| 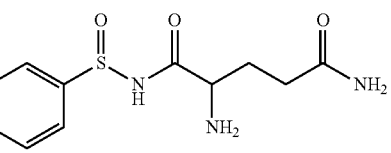 | ANASA-018 |
| 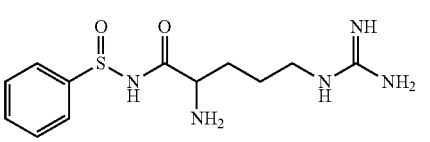 [SMILES: N=C(N)NCCCC(N)C(=O)NS(=O)c1ccccc1] | ANASA-019 |
| 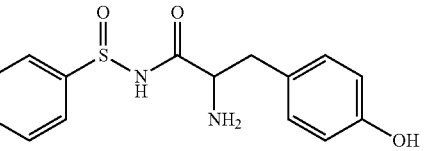 | ANASA-020 |
| 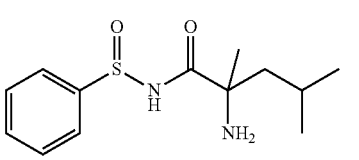 | ANASA-021 |

-continued
| Structure | Code |
|---|---|
| 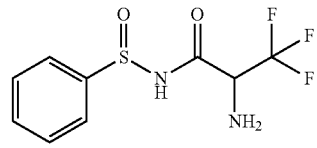 [SMILES: NC(C(=O)NS(=O)c1ccccc1)C(F)(F)F] | ANASA-022 |
| 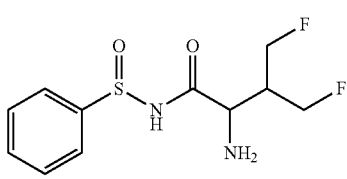 [SMILES: NC(C(=O)NS(=O)c1ccccc1)C(CF)CF] | ANASA-023 |
| 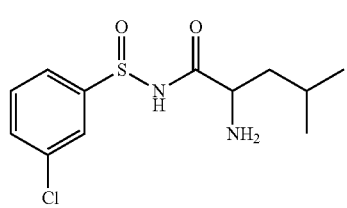 [SMILES: CC(C)CC(N)C(=O)NS(=O)c1cccc(Cl)c1] | ANASA-024 |
| 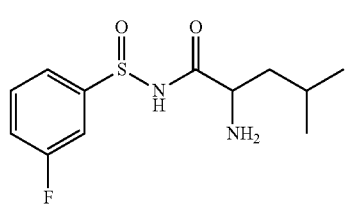 [SMILES: CC(C)CC(N)C(=O)NS(=O)c1cccc(F)c1] | ANASA-025 |
| 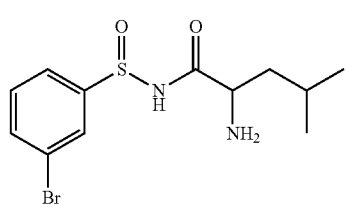 [SMILES: CC(C)CC(N)C(=O)NS(=O)c1cccc(Br)c1] | ANASA-026 |
| 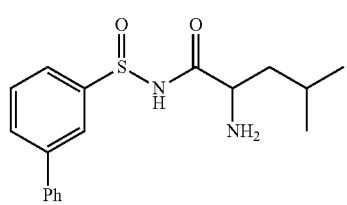 [SMILES: CC(C)CC(N)C(=O)NS(=O)c1cccc(-c2ccccc2)c1] | ANASA-027 |
| 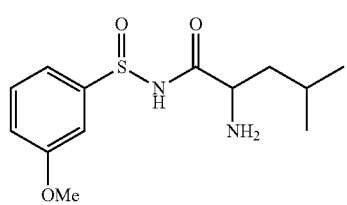 [SMILES: COc1cccc(S(=O)NC(=O)C(N)CC(C)C)c1] | ANASA-028 |
-continued
| Structure | Code |
|---|---|
| 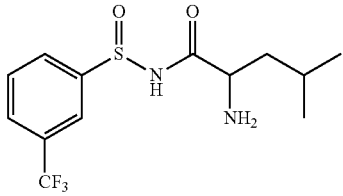 [SMILES: CC(C)CC(N)C(=O)NS(=O)c1cccc(C(F)(F)F)c1] | ANASA-029 |
| 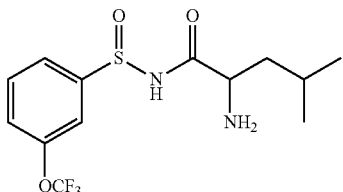 | ANASA-030 |
| 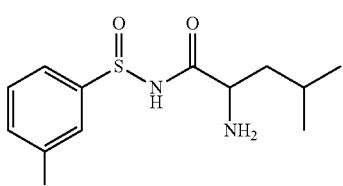 | ANASA-031 |
| 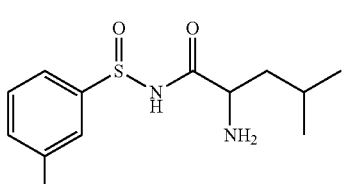 | ANASA-032 |
| 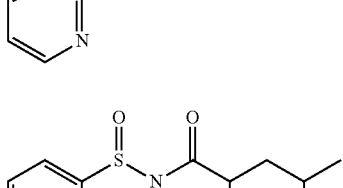 | ANASA-033 |
| 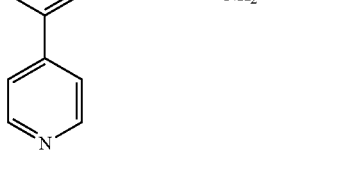 | ANASA-034 |
| 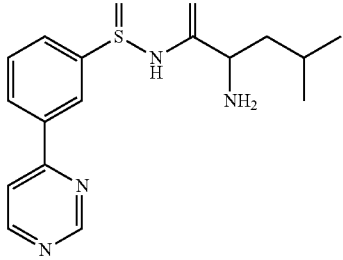 | |

-continued
| Structure | Code |
|---|---|
| 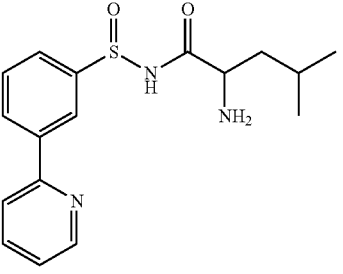 [SMILES: CC(C)CC(N)C(=O)NS(=O)c1cccc(-c2ccccn2)c1] | ANASA-035 |
| 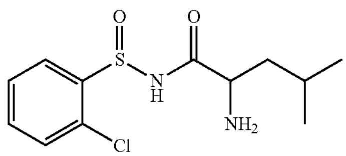 [SMILES: CC(C)CC(N)C(=O)NS(=O)c1ccccc1Cl] | ANASA-036 |
| 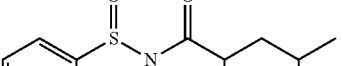 | ANASA-037 |
| 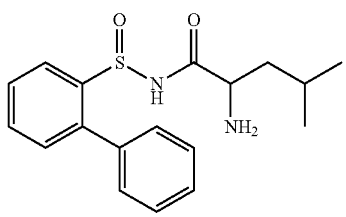 [SMILES: CC(C)CC(N)C(=O)NS(=O)c1ccccc1-c1ccccc1] | ANASA-038 |
| 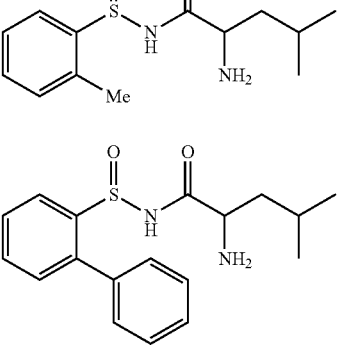 | ANASA-039 |
| 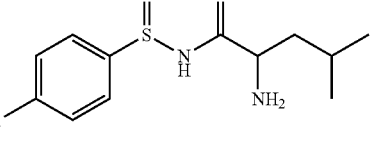 | ANASA-040 |
| 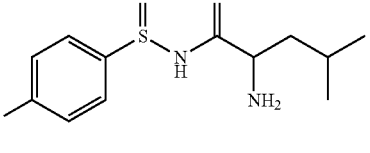 | ANASA-041 |
| 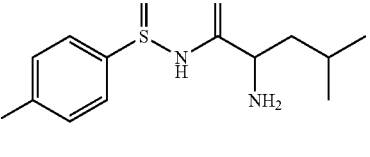 | ANASA-042 |
-continued
| Structure | Code |
|---|---|
| 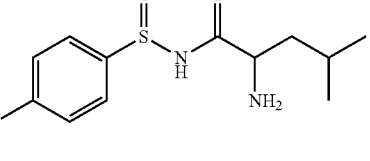 | ANASA-043 |
| 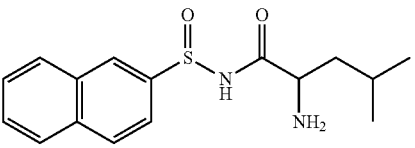 [SMILES: CC(C)CC(N)C(=O)NS(=O)c1ccc2ccccc2c1] | ANASA-044 |
| 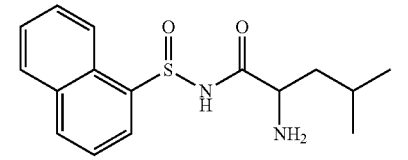 [SMILES: CC(C)CC(N)C(=O)NS(=O)c1cccc2ccccc12] | ANASA-045 |
| 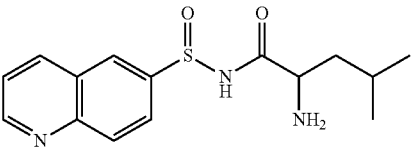 [SMILES: CC(C)CC(N)C(=O)NS(=O)c1ccc2ncccc2c1] | ANASA-046 |
| 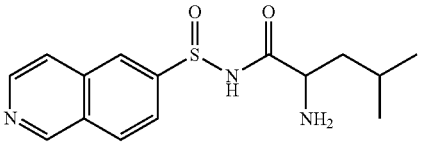 [SMILES: CC(C)CC(N)C(=O)NS(=O)c1ccc2cnccc2c1] | ANASA-047 |
| 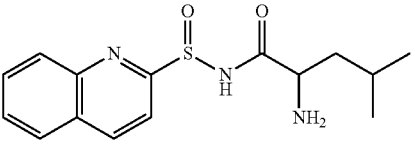 [SMILES: CC(C)CC(N)C(=O)NS(=O)c1ccc2ccccc2n1] | ANASA-048 |
| 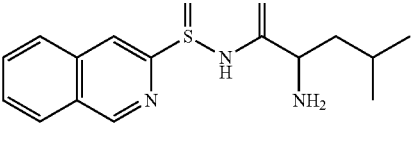 | ANASA-049 |
| 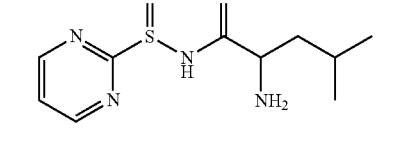 | ANASA-050 |
| 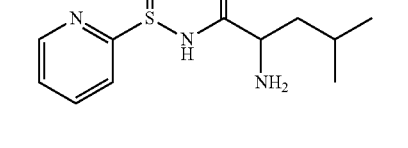 | ANASA-051 |

-continued
| Structure | Code |
|---|---|
| 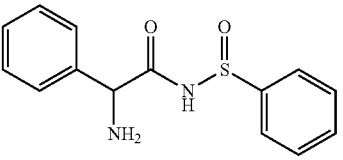 [SMILES: NC(C(=O)NS(=O)c1ccccc1)c1ccccc1] | ANASA-052 |
| 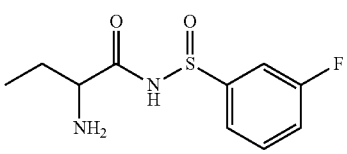 [SMILES: CCC(N)C(=O)NS(=O)c1cccc(F)c1] | ANASA-053 |
| 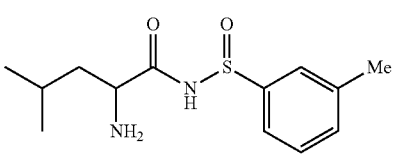 [SMILES: Cc1cccc(S(=O)NC(=O)C(N)CC(C)C)c1] | ANASA-054 |
| 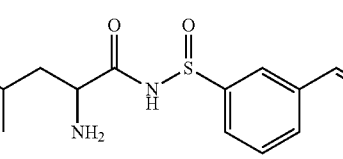 | ANASA-055 |
| 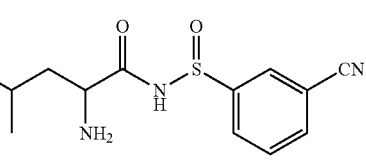 | ANASA-056 |
| 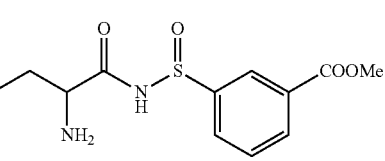 | ANASA-057 |
| 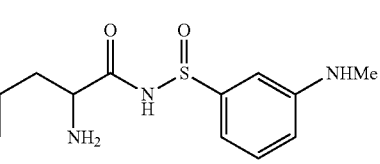 | ANASA-058 |
| 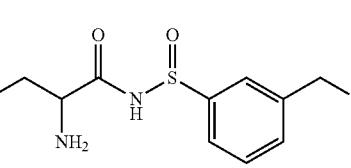 | ANASA-059 |
| 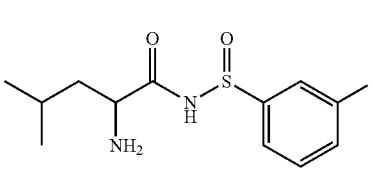 | ANASA-060 |
-continued
| Structure | Code |
|---|---|
| 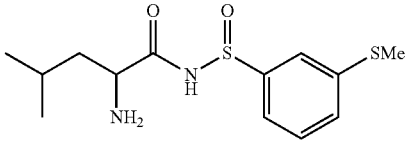 | ANASA-061 |
| 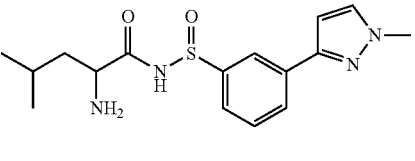 [SMILES: CC(C)CC(N)C(=O)NS(=O)c1cccc(-c2ccn(C)n2)c1] | ANASA-062 |
| 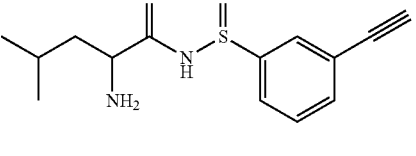 | ANASA-063 |
| 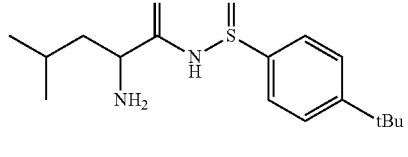 | ANASA-064 |
| 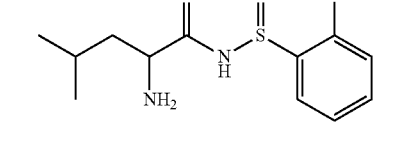 | ANASA-065 |
| 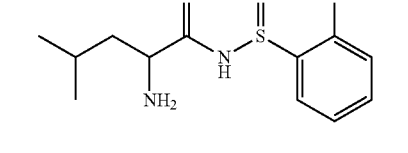 | ANASA-066 |
| 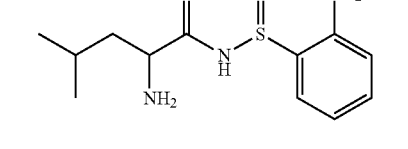 | ANASA-067 |
| 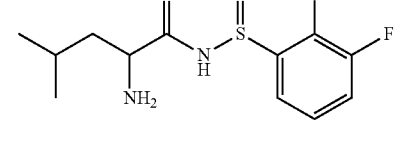 | ANASA-068 |
| 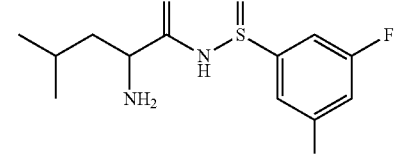 | ANASA-069 |

| Structure | Code |
|---|---|
| 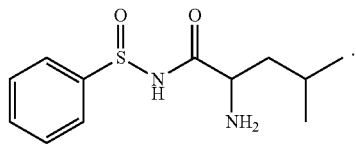 [SMILES: CC(C)CC(N)C(=O)NS(=O)c1ccccc1] | ANASA-070 |
| 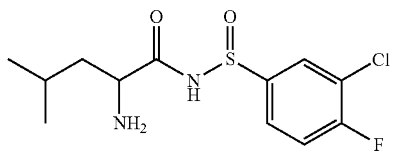 [SMILES: CC(C)CC(N)C(=O)NS(=O)c1ccc(F)c(Cl)c1] | ANASA-071 |
| 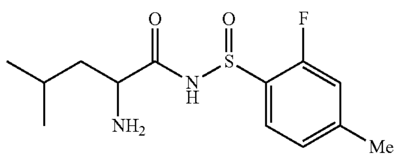 [SMILES: Cc1ccc(S(=O)NC(=O)C(N)CC(C)C)c(F)c1] | ANASA-072 |
| 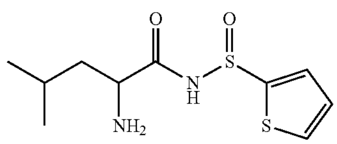 [SMILES: CC(C)CC(N)C(=O)NS(=O)c1cccs1] | ANASA-073 |
| 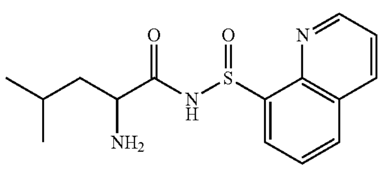 [SMILES: CC(C)CC(N)C(=O)NS(=O)c1cccc2cccnc12] | ANASA-074 |
| 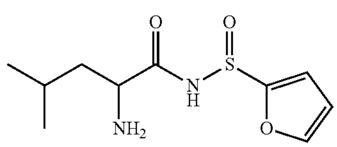 [SMILES: CC(C)CC(N)C(=O)NS(=O)c1ccco1] | ANASA-075 |

(193) A compound according to (1), which is selected from compounds of the following formulae, and pharmaceutically acceptable salts, hydrates, and solvates thereof:

ANASA-001; ANASA-002; ANASA-003; ANASA-004; ANASA-007; ANASA-012; ANASA-021; ANASA-024; ANASA-025; ANASA-026; ANASA-027; ANASA-028; ANASA-029; ANASA-030; ANASA-036; ANASA-040; ANASA-043; ANASA-044; ANASA-050; ANASA-052; ANASA-053; ANASA-054; ANASA-055; ANASA-056; ANASA-057; ANASA-058; ANASA-059; ANASA-060; ANASA-061; ANASA-062; ANASA-063; ANASA-064; ANASA-065; ANASA-066; ANASA-067; ANASA-068; ANASA-069; ANASA-070; ANASA-071; ANASA-072; ANASA-073; ANASA-074; ANASA-075.

(194) A compound according to (1), which is selected from compounds of the following formula, and pharmaceutically acceptable salts, hydrates, and solvates thereof:

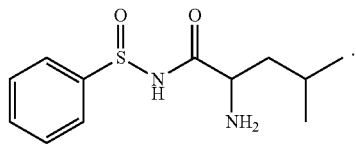 [SMILES: CC(C)CC(N)C(=O)NS(=O)c1ccccc1]

Chiral Centres (195) A compound according to any one of (1) to (194), wherein the sulfur atom which forms part of the sulfoxide group (i.e., marked with an asterisk (*) in the following formula), is in the (R) configuration.

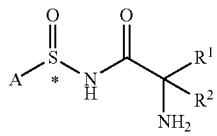

(196) A compound according to any one of (1) to (194), wherein the sulfur atom which forms part of the sulfoxide group (i.e., marked with an asterisk (*) in the previous formula) is in the (S) configuration.

(197) A compound according to any one of (1) to (194), wherein the carbon atom to which —$R^1$ and —$R^2$ are attached (i.e., marked with a hash (#) in the following formula) is in the (R) configuration.

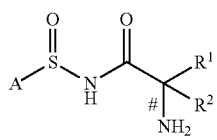

(198) A compound according to any one of (1) to (194), wherein the carbon atom to which —$R^1$ and —$R^2$ are attached (i.e., marked with a hash (#) in the previous formula) is in the (S) configuration.

(199) A compound according to any one of (1) to (194), wherein:
the sulfur atom which forms part of the sulfoxide group (i.e., marked with an asterisk (*) in the following formula) is in the (R) configuration; and
the carbon atom to which —$R^1$ and —$R^2$ are attached (i.e., marked with a hash (#) in the following formula) is in the (R) configuration.

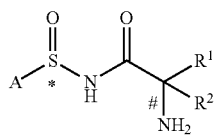

(200) A compound according to any one of (1) to (194), wherein:
the sulfur atom which forms part of the sulfoxide group (i.e., marked with an asterisk (*) in the above formula) is in the (R) configuration; and
the carbon atom to which —$R^1$ and —$R^2$ are attached (i.e., marked with a hash (#) in the above formula) is in the (S) configuration.

(201) A compound according to any one of (1) to (194), wherein:
the sulfur atom which forms part of the sulfoxide group (i.e., marked with an asterisk (*) in the above formula) is in the (S) configuration; and
the carbon atom to which —R¹ and —R² are attached (i.e., marked with a hash (#) in the above formula) is in the (R) configuration.

(202) A compound according to any one of (1) to (194), wherein:
the sulfur atom which forms part of the sulfoxide group (i.e., marked with an asterisk (*) in the above formula) is in the (S) configuration; and
the carbon atom to which —R¹ and —R² are attached (i.e., marked with a hash (#) in the above formula) is in the (S) configuration.

(203) A compound according to any one of (1) to (194), wherein:
the sulfur atom which forms part of the sulfoxide group (i.e., marked with an asterisk (*) in the following formula) is in the (R) configuration; and
the carbon atom to which —R¹ and —R² are attached (i.e., marked with a hash (#) in the following formula) is not chiral (i.e., —R¹ and —R² are the same).

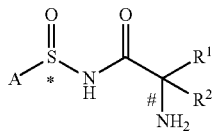

(204) A compound according to any one of (1) to (194), wherein:
the sulfur atom which forms part of the sulfoxide group (i.e., marked with an asterisk (*) in the above formula) is in the (S) configuration; and
the carbon atom to which —R¹ and —R² are attached (i.e., marked with a hash (#) in the following formula) is not chiral (i.e., —R¹ and —R² are the same).

(205) A compound according to (1), which is selected from compounds of the following formula, and pharmaceutically acceptable salts, hydrates, and solvates thereof:

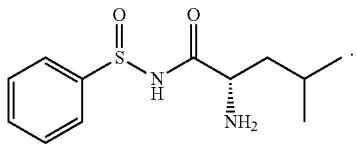 [SMILES: CC(C)C[C@H](N)C(=O)NS(=O)c1ccccc1]

(206) A compound according to (1), which is selected from compounds of the following formula, and pharmaceutically acceptable salts, hydrates, and solvates thereof:

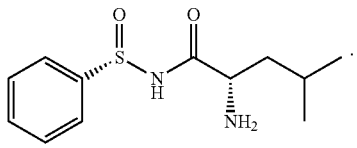 [SMILES: CC(C)C[C@H](N)C(=O)N[S@@](=O)c1ccccc1]

(207) A compound according to (1), which is selected from compounds of the following formula, and pharmaceutically acceptable salts, hydrates, and solvates thereof:

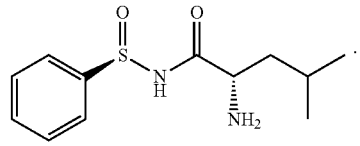 [SMILES: CC(C)C[C@H](N)C(=O)N[S@](=O)c1ccccc1]

Optional Provisos

Optionally, the compounds are as defined here, but further limited by one or more provisos, as discussed below.

(208) A compound according to any one of (1) to (207), with the proviso that:
the compound is not a compound of the following formula, or a pharmaceutically acceptable salt, hydrate, or solvate thereof:

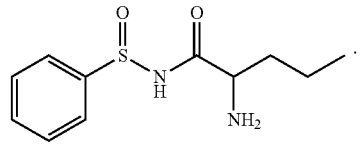 [SMILES: CCCC(N)C(=O)NS(=O)c1ccccc1]

(209) A compound according to any one of (1) to (207), with the proviso that:
if the group —C(NH₂)R¹R² is —CH(NH₂)CH₂CH₂CH₃, then -A is other than unsubstituted phenyl.

(210) A compound according to any one of (1) to (207), with the proviso that:
if -A is unsubstituted phenyl, then the group —C(NH₂)R¹R² is other than —CH(NH₂)CH₂CH₂CH₃.

(211) A compound according to any one of (1) to (207), with the proviso that:
the group —C(NH₂)R¹R² is other than —CH(NH₂)CH₂CH₂CH₃.

(212) A compound according to any one of (1) to (207), with the proviso that:
A is other than unsubstituted phenyl.

Combinations

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the chemical groups represented by the variables (e.g., -A, —R¹, —R², etc.) are specifically embraced by the present invention and are disclosed herein just as if each and every combination was individually and explicitly disclosed, to the extent that such combinations embrace compounds that are stable compounds (i.e., compounds that can be isolated, characterised, and tested for biological activity). In addition, all sub-combinations of the chemical groups listed in the embodiments describing such variables are also specifically embraced by the present invention and are disclosed herein just as if each and every such sub-combination of chemical groups was individually and explicitly disclosed herein.

Substantially Purified Forms

One aspect of the present invention pertains to ANASA compounds, in purified form.

In one embodiment, the compound is in substantially purified form and/or in a form substantially free from contaminants.

In one embodiment, the compound is in a substantially purified form with a purity of least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless specified, the substantially purified form refers to the compound in any stereoisomeric or enantiomeric form. For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to an equimolar mixture of enantiomers (i.e., a racemic mixture, a racemate). In one embodiment, the substantially purified form refers to one enantiomer, e.g., optically pure enantiomer.

In one embodiment, the compound is in a form substantially free from contaminants wherein the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers or enantiomers. In one embodiment, the contaminants refer to other compounds and other stereoisomers. In one embodiment, the contaminants refer to other compounds and the other enantiomer.

In one embodiment, the compound is in a substantially purified form with an optical purity of at least 60% (i.e., 60% of the compound, on a molar basis, is the desired stereoisomer or enantiomer, and 40% is undesired stereoisomer(s) or enantiomer), e.g., at least 70%, e.g., at least 80%, e.g., at least 90%, e.g., at least 95%, e.g., at least 97%, e.g., at least 98%, e.g., at least 99%.

Isomers

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., C$_{1-3}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

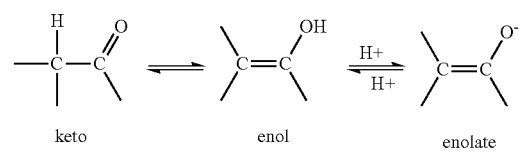

keto      enol      enolate

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; S may be in any isotopic form, including $^{32}$S, $^{33}$S, $^{34}$S, $^{35}$S, and $^{36}$S; and the like.

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic (e.g., —COOH may be —COO—), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{3+}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, formic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Hydrates and Solvates

It may be convenient or desirable to prepare, purify, and/or handle a corresponding solvate of the compound. The term "solvate" is used herein in the conventional sense to refer to a complex of solute (e.g., compound, salt of compound) and solvent. If the solvent is water, the solvate may be conveniently referred to as a hydrate, for example, a hemi-hydrate, a mono-hydrate, a sesqui-hydrate, a di-hydrate, a tri-hydrate, etc.

Unless otherwise specified, a reference to a particular compound also includes solvate and hydrate forms thereof.

Chemically Protected Forms

It may be convenient or desirable to prepare, purify, and/or handle the compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Greene and P. Wuts; 4th Edition; John Wiley and Sons, 2006).

A wide variety of such "protecting," "blocking," or "masking" methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH$_3$, —OAc).

For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH—Fmoc), as a 6-nitroveratryloxy amide (—NH—Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulfonyl)ethyloxy amide (—NH—Psec); or, in suitable cases (e.g., cyclic amines), as a nitroxide radical (>N—O●).

Prodrugs

It may be convenient or desirable to prepare, purify, and/or handle the compound in the form of a prodrug. The term "prodrug," as used herein, pertains to a compound which, when metabolised (e.g., in vivo), yields the desired active compound. Typically, the prodrug is inactive, or less active than the desired active compound, but may provide advantageous handling, administration, or metabolic properties.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

General Chemical Synthesis

Methods for the chemical synthesis of ANASA compounds are described herein. These and/or other well-known methods may be modified and/or adapted in known ways in order to facilitate the synthesis of additional compounds described herein.

For example, as illustrated in the following scheme, an appropriate aryl sulfonate (A) may be transformed to the corresponding arylsulfinamide (B), for example by reaction with oxalyl chloride. The product (B) may then be acylated by reaction with a suitably protected ("Prot") and suitably activated ("Act") alpha-amino acid (C) to give the corresponding protected 2-amino-N-(arylsulfinyl)-acetamide (D). The product (D) may be deprotected to give the target 2-amino-N-(arylsulfinyl)-acetamide (E). Individual stereoisomers (enantiomers, diastereomers) of (E) may then be isolated, if desired.

Scheme 1

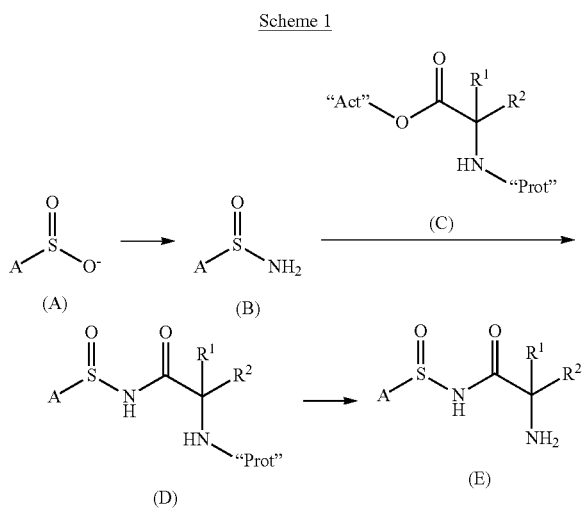

Compositions

One aspect of the present invention pertains to a composition (e.g., a pharmaceutical composition) comprising an ANASA compound, as described herein, and a pharmaceutically acceptable carrier, diluent, or excipient.

Another aspect of the present invention pertains to a method of preparing a composition (e.g., a pharmaceutical composition) comprising mixing an ANASA compound, as described herein, and a pharmaceutically acceptable carrier, diluent, or excipient.

Uses

The ANASA compounds, as described herein, are useful, for example, in the treatment of disorders (e.g., diseases) that are ameliorated by the inhibition (e.g., selective inhibition) of bacterial aminoacyl-tRNA synthetase (aaRS) (e.g., bacterial leucyl-tRNA synthetase, LeuRS; etc.), as described herein.

Selectivity

In one embodiment, the inhibition of bacterial aminoacyl-tRNA synthetase (aaRS) is selective inhibition, e.g., with respect to mammalian aminoacyl-tRNA synthetase (aaRS), e.g., the corresponding mammalian aminoacyl-tRNA synthetase.

In one embodiment, the inhibition of bacterial aminoacyl-tRNA synthetase (aaRS) is selective inhibition, e.g., with respect to human aminoacyl-tRNA synthetase (aaRS), e.g., the corresponding human aminoacyl-tRNA synthetase.

For example, in one embodiment, the ANASA compound selectively inhibits bacterial leucyl-tRNA synthetase (LeuRS), as compared to human leucyl-tRNA synthetase (LeuRS).

Use in Methods of Inhibiting Bacterial Aminoacyl-tRNA Synthetase

One aspect of the present invention pertains to a method of inhibiting (e.g., selectively inhibiting) bacterial aminoacyl-tRNA synthetase (aaRS) (e.g., bacterial leucyl-tRNA synthetase, LeuRS, etc.), in vitro or in vivo, comprising contacting the synthetase with an effective amount of an ANASA compound, as described herein.

One aspect of the present invention pertains to a method of inhibiting (e.g., selectively inhibiting) bacterial aminoacyl-tRNA synthetase (aaRS) (e.g., bacterial leucyl-tRNA synthetase, LeuRS, etc.) function in a cell (e.g., a bacterial cell), in vitro or in vivo, comprising contacting the cell with an effective amount of an ANASA compound, as described herein.

One of ordinary skill in the art is readily able to determine whether or not a candidate compound inhibits bacterial aminoacyl-tRNA synthetase (e.g., bacterial leucyl-tRNA synthetase, etc.). For example, suitable assays are described herein or are known in the art.

In one embodiment, the method is performed in vitro.

In one embodiment, the method is performed in vivo.

In one embodiment, the ANASA compound is provided in the form of a pharmaceutically acceptable composition.

One aspect of the present invention pertains to a method of inhibiting bacterial aminoacyl-tRNA synthetase (e.g., bacterial leucyl-tRNA synthetase, etc.), in a cell (e.g., a bacterial cell), in vitro or in vivo, comprising contacting the cell with an effective amount of an ANASA compound, as described herein.

For example, a sample of cells may be grown in vitro and a compound brought into contact with said cells, and the effect of the compound on those cells observed. As an example of "effect," the morphological status of the cells (e.g., alive or dead, etc.) may be determined. Where the compound is found to exert an influence on the cells, this may be used as a prognostic or diagnostic marker of the efficacy of the compound in methods of treating a patient carrying cells of the same cellular type.

Use in Methods of Therapy

Another aspect of the present invention pertains to an ANASA compound, as described herein, for use in a method of treatment of the human or animal body by therapy, for example, for use in a method of treatment of a disorder (e.g., a disease) as described herein.

Use in the Manufacture of Medicaments

Another aspect of the present invention pertains to use of an ANASA compound, as described herein, in the manufacture of a medicament, for example, for use in a method of treatment, for example, for use a method of treatment of a disorder (e.g., a disease) as described herein.

In one embodiment, the medicament comprises the ANASA compound.

Methods of Treatment

Another aspect of the present invention pertains to a method of treatment, for example, a method of treatment of a disorder (e.g., a disease) as described herein, comprising administering to a subject in need of treatment a therapeutically-effective amount of an ANASA compound, as described herein, preferably in the form of a pharmaceutical composition.

Disorders Treated—Disorders Ameliorated by the Inhibition of Bacterial Aminoacyl-tRNA Synthetase In one embodiment (e.g., of use in methods of therapy, of use in the manufacture of medicaments, of methods of treatment), the treatment is treatment of a disorder (e.g., a disease) that is ameliorated by the inhibition (e.g., selective inhibition) of bacterial aminoacyl-tRNA synthetase (e.g., bacterial leucyl-tRNA synthetase, etc.).

Disorders Treated—Bacterial Infections

In one embodiment (e.g., of use in methods of therapy, of use in the manufacture of medicaments, of methods of treatment), the treatment is treatment of: a bacterial infection.

In one embodiment, the bacteria are Gram-positive bacteria (i.e., the bacterial infection is an infection with Gram-positive bacteria; the bacterial infection is a Gram-positive bacterial infection; etc.).

In one embodiment, the bacteria are Gram-negative bacteria.

In one embodiment, the bacteria are aerobic bacteria.

In one embodiment, the bacteria are anaerobic bacteria.

In one embodiment, the bacteria are intracellular bacteria.
In one embodiment, the bacteria are:
*Staphylococci*, for example *S. aureus*;
*Enterococci*, for example *E. faecalis*;
*Streptococci*, for example *S. pneumoniae*;
*Haemophilus*, for example *H. influenza*;
*Moraxella*, for example *M. catarrhalis*; or
*Escherichia*, for example *E. coli*.
In one embodiment, the bacteria are:
Mycobacteria, for example *M. tuberculosis*.
In one embodiment, the bacteria are:
*Chlamydia*, for example, *C. trachomatis*;
*Rickettsiae*, for example, *R. prowazekii*; or
*Mycoplasma*, for example, *M. pneumoniae*.

Type/Location of Infection

The infection may be associated with a particular location, organ, etc.

In one embodiment, the infection is:
a central nervous system infection;
an external ear infection;
an infection of the middle ear, including acute otitis media;
an infection of the cranial sinuses;
an eye infection;
an infection of the oral cavity, including an infection of the teeth, gums, or mucosa;
an upper respiratory tract infection;
a lower respiratory tract infection;
a genitourinary infection;
a urinary tract infection;
an intra-abdominal infection;
a gastrointestinal infection;
a gynecological infection;
septicemia,
a bone or joint infection
a skin or skin structure infection;
bacterial endocarditis; or
a burn infection.

Prophylaxis

The treatment may be treatment as prophylaxis, for example: antibacterial prophylaxis in surgery; and antibacterial prophylaxis in immunosuppressed patients, including patients receiving cancer chemotherapy, or organ transplant patients.

Treatment

The term "treatment," as used herein in the context of treating a disorder, pertains generally to treatment of a human or an animal (e.g., in veterinary applications), in which some desired therapeutic effect is achieved, for example, the inhibition of the progress of the disorder, and includes a reduction in the rate of progress, a halt in the rate of progress, alleviation of symptoms of the disorder, amelioration of the disorder, and cure of the disorder. Treatment as a prophylactic measure (i.e., prophylaxis) is also included. For example, use with patients who have not yet developed the disorder, but who are at risk of developing the disorder, is encompassed by the term "treatment."

For example, treatment of bacterial infection includes the prophylaxis of bacterial infection, reducing the incidence of bacterial infection, alleviating the symptoms of bacterial infection, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously. For example, the compounds described herein may also be used in combination therapies, e.g., in conjunction with other agents.

One aspect of the present invention pertains to a compound as described herein, in combination with one or more (e.g., 1, 2, 3, 4, etc.) additional therapeutic agents, for example, other anti-bacterial agents.

The particular combination would be at the discretion of the physician who would select dosages using their common general knowledge and dosing regimens known to a skilled practitioner.

The agents (i.e., the ANASA compound described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., the compound described here, plus one or more other agents) may be formulated together in a single dosage form, or alternatively, the individual agents may be formulated separately and presented together in the form of a kit, optionally with instructions for their use.

Other Uses

The ANASA compounds described herein may also be used as cell culture additives to inhibit bacterial aminoacyl-tRNA synthetase (e.g., bacterial leucyl-tRNA synthetase, etc.).

The ANASA compounds described herein may also be used as part of an in vitro assay, for example, in order to determine whether a candidate host is likely to benefit from treatment with the compound in question.

The ANASA compounds described herein may also be used as a standard, for example, in an assay, in order to identify other active compounds, other bacterial aminoacyl-tRNA synthetase inhibitors, etc.

Kits

One aspect of the invention pertains to a kit comprising (a) an ANASA compound as described herein, or a composition comprising an ANASA compound as described herein, e.g., preferably provided in a suitable container and/or with suitable packaging; and (b) instructions for use, e.g., written instructions on how to administer the compound or composition.

The written instructions may also include a list of indications for which the active ingredient is a suitable treatment.

Routes of Administration

The ANASA compound or pharmaceutical composition comprising the ANASA compound may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus.

In one preferred embodiment, the subject/patient is a human.

Formulations

While it is possible for an ANASA compound to be administered alone, it is preferable to present it as a pharmaceutical formulation (e.g., composition, preparation, medicament) comprising at least one ANASA compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising mixing at least one ANASA compound, as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences*, 18th edition, Mack Publishing Company, Easton, Pa., 1990; and *Handbook of Pharmaceutical Excipients*, 5th edition, 2005.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or mixed with one or more other pharmaceutically acceptable ingredients. The compound may be presented in a liposome or other microparticulate which is designed to target the compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the compound in a flavored basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1, 3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprise a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichloro-tetrafluoroethane, carbon dioxide, or other suitable gases.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additionally contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/mL to about 10 µg/mL, for example from about 10 ng/mL to about 1 µg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use.

Extemporaneous injection solutions and suspensions may be prepared from sterile powders, granules, and tablets.

Dosage

It will be appreciated by one of skill in the art that appropriate dosages of the ANASA compounds, and compositions comprising the ANASA compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular ANASA compound, the route of administration, the time of administration, the rate of excretion of the ANASA compound, the duration of the treatment, other drugs, compounds, and/or materials used in combination, the severity of the disorder, and the species, sex, age, weight, condition, general health, and prior medical history of the patient. The amount of ANASA compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the ANASA compound is in the range of about 0.1 mg to about 5000 mg (more typically about 10 mg to about 3000 mg) per kilogram body weight of the subject per day. Where the compound is a salt, an ester, an amide, a prodrug, or the like, the amount administered is calculated on the basis of the parent compound and so the actual weight to be used is increased proportionately.

EXAMPLES

Chemical Synthesis

The following examples are provided solely to illustrate the present invention and are not intended to limit the scope of the invention, as described herein.

Synthesis 1

(2S)-2-amino-4-methyl-N—[(S)-phenylsulfinyl]pentanamide (Va)

(2S)-2-amino-4-methyl-N—[(R)-phenylsulfinyl]pentanamide (Vb)

The title compounds were prepared using the method illustrated in the following scheme. Sodium sulfonate (I) was transformed to sulfinamide (II), which was acylated with Boc-L-leucine N-hydoxysuccinimide ester (III). The resulting intermediate (IV) was deprotected to give products (Va) and (Vb) as a mixture of diastereomers, which were separated using reverse phase column chromatography.

Scheme 2

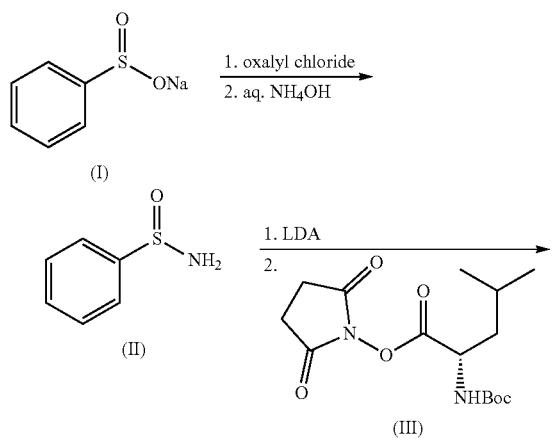

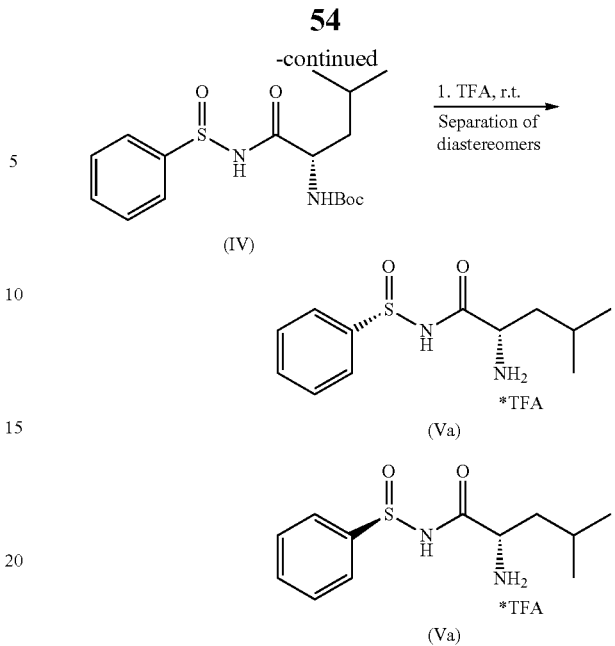

Step 1—Preparation of Intermediate (II)

Sodium benzenesulfinate (I) (1.0 g, 6.1 mmol) was dissolved in dry toluene (20 mL) under an argon atmosphere and the solution was cooled in an ice bath. Oxalyl chloride (0.45 mL, 5.2 mmol) was added dropwise over 5 minutes. The mixture was heated to room temperature and then stirred for 2 hours at room temperature. A mixture of concentrated aqueous $NH_4OH$ (20 mL) and EtOAc (15 mL) was added and the resulting suspension was stirred for 1 hour. The mixture was extracted with EtOAc (3×10 mL) and the combined organic phase was washed with saturated aqueous NaCl solution and dried over $Na_2SO_4$. Solvent was evaporated from the extract and the residue was purified by flash chromatography on silica gel eluting with a mixture of light petroleum ether and EtOAc (1:1) to give intermediate (II) (0.40 g, 46.5%).

Step 2—Preparation of Intermediate (IV)

A solution of lithium diisopropylamide (LDA) was freshly prepared by adding 1.6 M n-butyllithium (1.2 mL, 1.96 mmol) in hexane to a solution diisopropyl amine (0.28 mL, 1.96 mmol) in tetrahydrofuran (THF, 10 mL) under an argon atmosphere at −40° C. To this, a solution of sulfinamide (II) (251 mg, 1.78 mmol) in THF (5 mL) was added and the mixture was stirred for 10 minutes. A solution of Boc-L-leucine N-hydroxysuccinimide ester (III) (585 mg, 1.78 mmol) in THF (5 mL) was added and the mixture was warmed to room temperature and stirred for 48 hours. The mixture was cooled in an ice bath and quenched with aqueous 5% $KHSO_4$ and extracted with EtOAc (3×15 mL). The organic phase was dried over $Na_2SO_4$ and the solvents evaporated. The residue was purified by flash chromatography on silica gel eluting with mixture of light petroleum ether and EtOAc (2:1) to give intermediate (IV) (177 mg, 28%).

Step 3—Preparation and Separate of Target Compounds (Va) and (Vb)

Intermediate (IV) was dissolved in neat trifluoroacetic acid (TFA) and the mixture was stirred overnight at room temperature. The mixture was concentrated in vacuo and the diastereomers were separated by reverse phase chromatography on C18 silica gel eluting with a mixture of acetonitrile and water (acetonitrile gradient 5%-35%) to give a first diastereomer (V-i) as a fast eluting diastereomer and a second diastereomer (V-ii) as a slow eluting diastereomer.

First diastereomer (V-i): $^1$H-NMR (400 MHz, DMSO-d6) δ: 8.28 (1H, br s); 7.71-7.68 (2H, m); 7.65-7.62 (3H, m); 3.81 (1H, dd, J=5.6, 8.5 Hz); 1.70-1.50 (3H, m); 0.86 (3H, d, J=6.4 Hz); 0.84 ppm (3H, d, J=6.4 Hz). LC/MS 255 (M+1).

Second diastereomer (V-ii): $^1$H-NMR (400 MHz, DMSO-d6) δ: 8.92 (1H, br s); 7.73-7.71 (2H, m); 7.67-7.62 (3H, m); 3.79 (1H, broad t, J=6.3 Hz); 1.73-1.50 (3H, m); 0.87 (3H, d, J=5.7 Hz); 0.85 ppm (3H, d, J=5.6 Hz). LC/MS 255 (M+1).

Additional Chemical Synthesis

General Synthesis

Compounds described herein were prepared according to the following general scheme. Sulfinamides 1.1-1.35 were acylated with Boc-protected amino acid N-hydroxysuccinimide esters 2.1-2.10. The resulting intermediates 3.1-3.44 were deprotected to give the target compounds 4.1-4.44.

Scheme 1

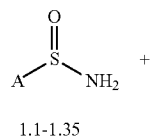

1.1-1.35

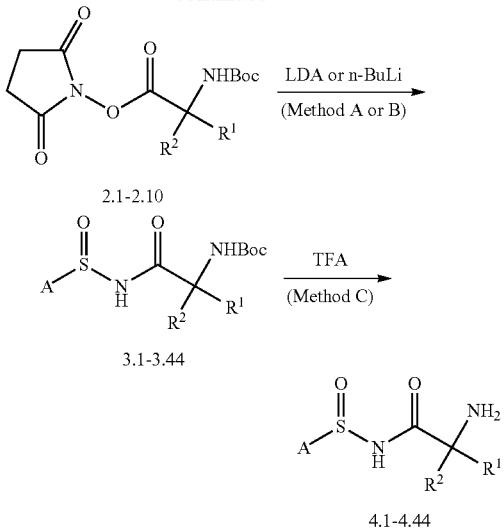

In one method, the sulfinamides 1 were prepared according to the following general scheme. Sodium benzenesulfinate 6.1 was available commercially. Other benzenesulfinate derivatives 6.2-6.30 were prepared by reduction of sulfonyl chlorides 5.2-5.30 with sodium sulfite. Some of the benzenesulfinate derivatives were treated with oxalyl chloride to give intermediate sulfinyl chlorides which reacted with ammonia to give benzenesulfonamides 1.1, 1.2, 1.4-1.6, 1.9, 1.10, 1.12, 1.16, 1.17, 1.19-1.23, 1.25-1.27, 1.30-1.32. Other benzenesulfinate derivatives were transformed to methyl sulfinates 7.1-7.8 which were subjected to aminolysis with lithium hexamethyldisilazide to give, after work up, sulfinamides 1.3, 1.11, 1.24, 1.28, 1.29, 1.33-1.35.

Scheme 2

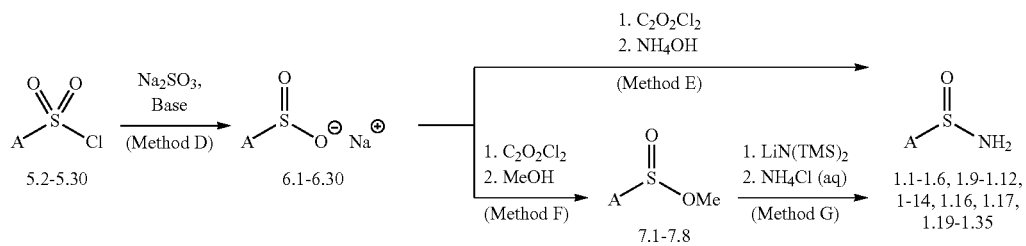

Enantio-enriched sulfinamides R-1.1, R-1.3 and S-1.1 were prepared from sulfinyl chlorides according to the following general scheme. The synthesis involved sulfinylation of (R)—N-benzyl-1-phenylethan-1-amine leading to diastereomeric sulfinylamides R-9.1/S-9.1 and R-9.3/S-9.3. The products were separated by column chromatography. Compounds R-9.1, R-9.3, S-9.1 were subjected to methanolysis resulting in methyl sulfinates S-10.1, S-10.3, R-10.1. Amidolysis of these methyl sulfinates yielded the sulfinamides R-1.1, R-1.3, S-1.1.

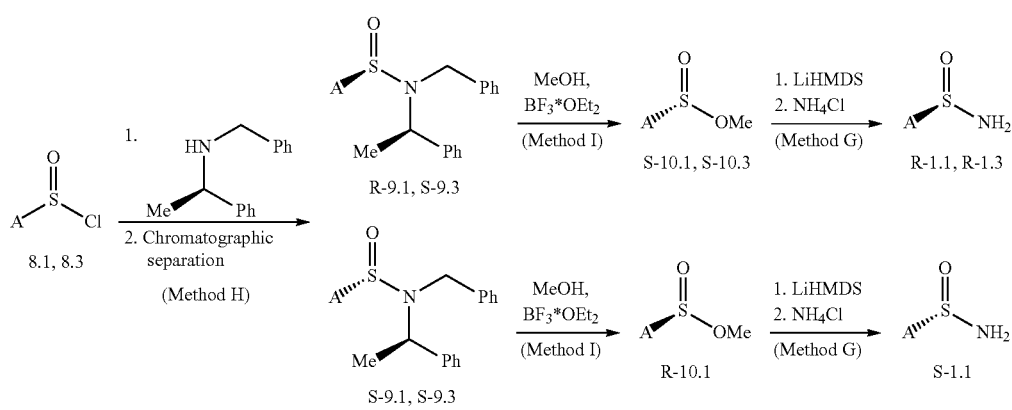

Sulfinamide 1.13 was prepared according to the following general scheme. 3-Bromobenzenesulfinamide (1.6) was subjected to copper catalyzed amination with methylamine to provide N-methyl-3-(methylamino)benzenesulfinamide (11), which was then transformed to sulfinamide 1.13 by an aminolysis reaction with ammonia.

Sulfinamides 1.7, 1.18, 1.8 were prepared according to the following general scheme. Pd-catalysed Suzuki-Miyaura coupling with potassium vinyltrifluoroborate was used to give sulfinamide 1.7. Sonogashira coupling with TMS acetylene was used to give sulfinamide 1.18. Suzuki-Miyaura coupling with phenyl boronic acid was used to give sulfinamide 1.8.

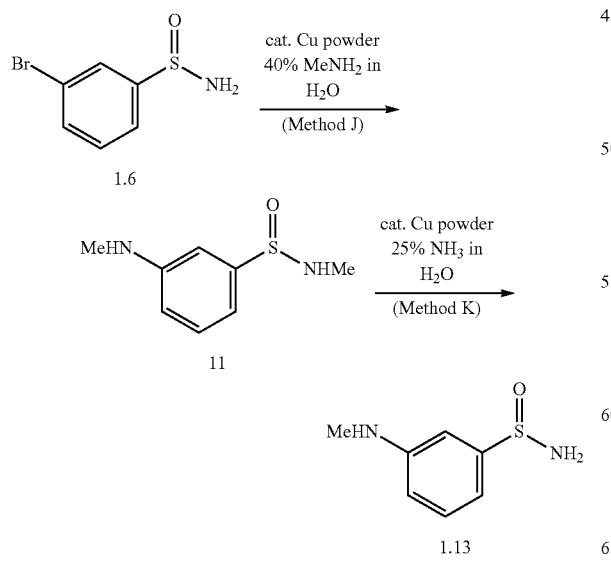

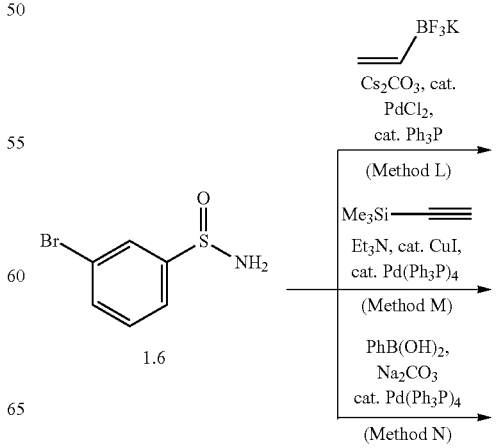

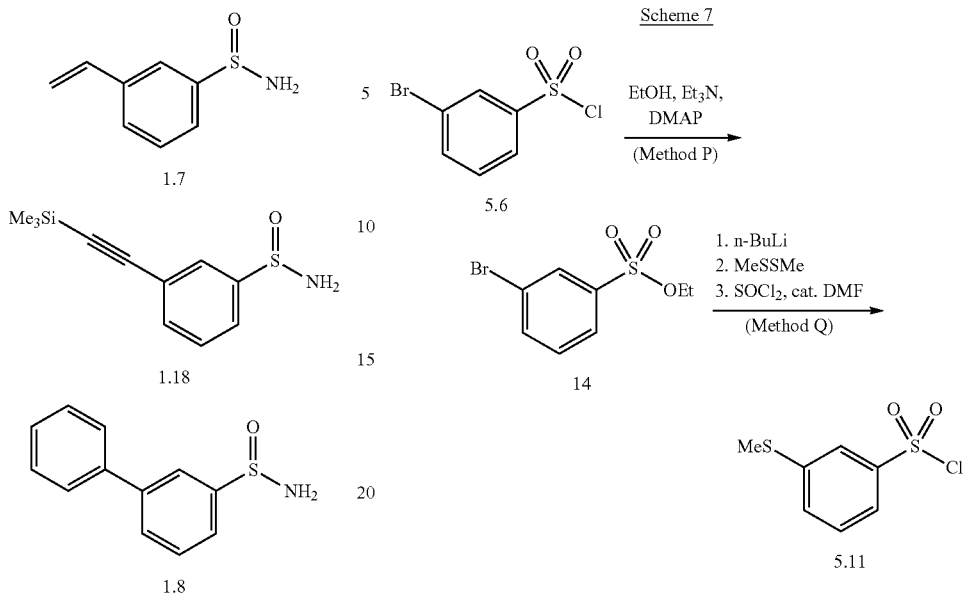

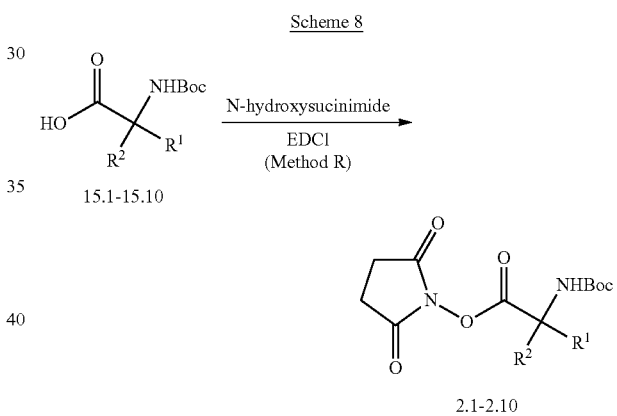

Sulfinamide 1.15 was prepared according to the following general scheme. Lithiation of diiodobenezene 12 was followed by the addition of sulfur dioxide to give lithium sulfinate 13. This was transformed to sulfinamide 1.15 by a one-pot two-step procedure which involved chlorination and subsequent amination.

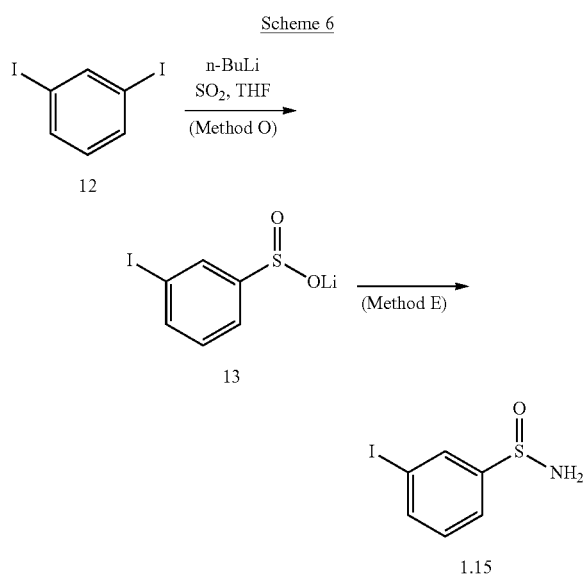

Most of the sulfonyl chlorides 5 used for the synthesis of sulfinamides 1 were commercially available.

3-Methylthiobenzenesulfonyl chloride 5.11 was prepared from the bromo analogue 5.6 according to the following general scheme. First, sulfonyl chloride 5.6 was transformed to ethyl sulfinate 14, which was then transformed to intermediate 3-(methylthio)benzenesulfonate salt via lithium halogen exchange, followed by the reaction with dimethyldisulfide, and then chlorination.

Activated esters 2.1-2.10 were prepared from the corresponding amino acids according to the following general scheme.

Detailed Synthesis
General Method A:

Exemplified by the Synthesis of tert-butyl (4-methyl-1-oxo-1-((phenylsulfinyl)amino)pentan-2-yl)carbamate (3.1)

A solution of lithium diisopropylamide (LDA) was freshly prepared by adding 1.6 M n-butyllithium (1.2 mL, 1.96 mmol) in hexanes to a solution of diisopropyl amine (0.28 mL, 1.96 mmol) in tetrahydrofuran (THF, 10 mL) under an argon atmosphere at −40° C. To this, a solution of benzene sulfinamide (1.1) (251 mg, 1.78 mmol) in THF (5 mL) was added and the mixture was stirred for 10 minutes. A solution of Boc-L-leucine N-hydroxysuccinimide ester (2.1) (585 mg, 1.78 mmol) in THF (5 mL) was added and the mixture was warmed to room temperature and stirred for 48 hours. The mixture was cooled in an ice bath and quenched with aqueous 5% KHSO₄ and extracted with EtOAc (3×15 mL). The organic phase was dried over Na₂SO₄ and the solvents evaporated. The residue was purified by flash chromatography on silica gel eluting with mixture of light petroleum ether and EtOAc (2:1) to give intermediate (3.1) (177 mg, 28%) as a mixture of diastereomers.

¹H NMR (300 MHz, Chloroform-d) δ: 7.77-7.69 (m, 2H), 7.57-7.49 (m, 3H), 4.77 (s, 1H), 4.10 (s, 1H), 1.83-1.60 (m, 2H), 1.58-1.42 (m, 1H, overlaps with H₂O signal), 1.36 (d, J=12.0 Hz, 9H), 0.98-0.86 (m, 6H).

The following compounds were obtained using methods analogous to Method A:

TABLE 2

| Cmpd. No. | Method | Precursor 1 | Precursor 2 | Structure |
|---|---|---|---|---|
| 3.1 | A | 1.1 | 2.1 | 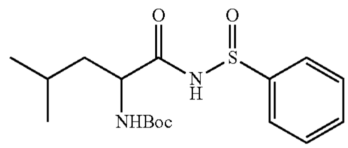 [SMILES: CC(C)CC(NC(=O)OC(C)(C)C)C(=O)NS(=O)c1ccccc1] |
| 3.21 | A | 1.12 | 2.1 | 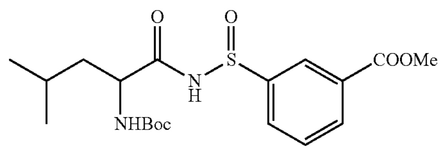 [SMILES: COC(=O)c1cccc(S(=O)NC(=O)C(CC(C)C)NC(=O)OC(C)(C)C)c1] |
| 3.22 | A | 1.13 | 2.1 | 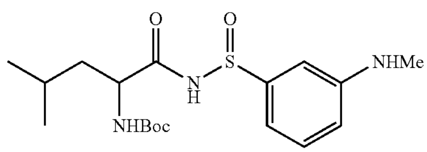 [SMILES: CNc1cccc(S(=O)NC(=O)C(CC(C)C)NC(=O)OC(C)(C)C)c1] |

General Method B:

Exemplified by the Synthesis of tert-butyl ((S)-4-methyl-1-oxo-1-(((R)-phenylsulfinyl)amino)pentan-2-yl)carbamate (S-3.1)

(R)-Benzenesulfinamide benzene sulfinamide R-1.1 (251 mg, 1.8 mmol) was dissolved in dry THF (30 mL), solution was cooled to −78° C. under an argon atmosphere. A 0.9 M solution of nBuLi in hexanes (2.0 mL, 1.8 mmol) was added dropwise. The resulting mixture was stirred at −78° C. for 10 minutes, and then Boc-L-leucine N-hydroxysuccinimide ester (2.1) (450 mg, 1.4 mmol) in THF (5 mL) was added dropwise, and then the mixture was warmed to room temperature and stirred for 16 hours. Silica gel (~20 g) was added to the reaction mixture and the solution was evaporated to dryness and purified by flash chromatography on silica gel eluting with gradient mixture of light petroleum ether and acetone (4:1 to 2:1) to give the title compound S-3.1 (361 mg, 74%).

¹H NMR (300 MHz, Chloroform-d) δ 7.77-7.69 (m, 2H), 7.57-7.49 (m, 3H), 4.77 (s, 1H), 4.10 (s, 1H), 1.83-1.60 (m, 2H), 1.58-1.42 (m, 1H, overlaps with H₂O signal), 1.36 (d, J=12.0 Hz, 9H), 0.98-0.86 (m, 6H).

The following compounds were obtained using methods analogous to Method B:

TABLE 3

| Cmpd. No. | Method | Precursor 1 | Precursor 2 | Structure |
|---|---|---|---|---|
| R-3.1 | B | R-1.1 | 2.1 | 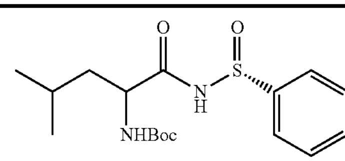 |
| S-3.1 | B | S-1.1 | 2.1 | 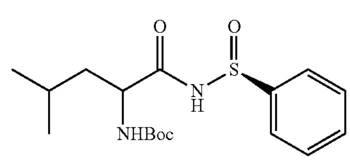 [SMILES: CC(C)CC(NC(=O)OC(C)(C)C)C(=O)N[S@@](=O)c1ccccc1] |
| 3.2 | B | 1.1 | 2.2 | 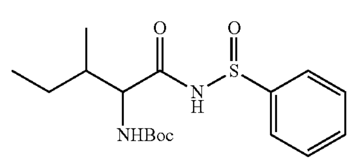 [SMILES: CCC(C)C(NC(=O)OC(C)(C)C)C(=O)NS(=O)c1ccccc1] |

TABLE 3-continued

| Cmpd. No. | Method | Precursor 1 | Precursor 2 | Structure |
|---|---|---|---|---|
| 3.3 | B | 1.1 | 2.3 | 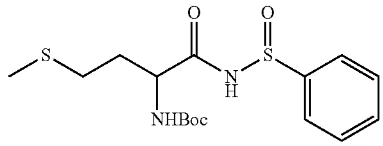 [SMILES: CSCCC(NC(=O)OC(C)(C)C)C(=O)NS(=O)c1ccccc1] |
| 3.4 | B | 1.1 | 2.4 | 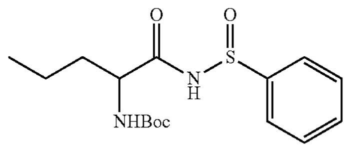 [SMILES: CCCC(NC(=O)OC(C)(C)C)C(=O)NS(=O)c1ccccc1] |
| 3.5 | B | 1.1 | 2.5 | 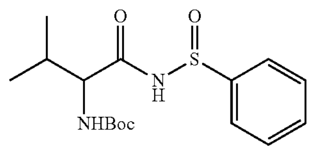 [SMILES: CC(C)C(NC(=O)OC(C)(C)C)C(=O)NS(=O)c1ccccc1] |
| 3.6 | B | 1.1 | 2.6 | 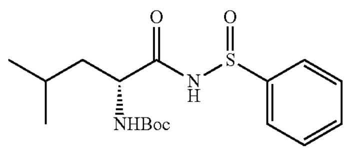 [SMILES: CC(C)C[C@@H](NC(=O)OC(C)(C)C)C(=O)NS(=O)c1ccccc1] |
| 3.7 | B | 1.1 | 2.7 | 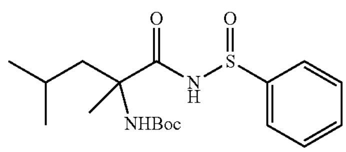 [SMILES: CC(C)CC(C)(NC(=O)OC(C)(C)C)C(=O)NS(=O)c1ccccc1] |
| 3.8 | B | 1.1 | 2.8 | 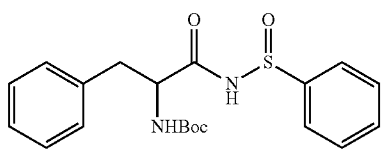 [SMILES: CC(C)(C)OC(=O)NC(Cc1ccccc1)C(=O)NS(=O)c1ccccc1] |
| 3.9 | B | 1.1 | 2.9 | 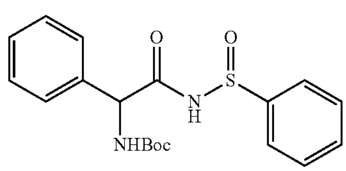 [SMILES: CC(C)(C)OC(=O)NC(C(=O)NS(=O)c1ccccc1)c1ccccc1] |
| 3.10 | B | 1.2 | 2.10 | 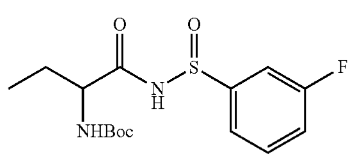 [SMILES: CCC(NC(=O)OC(C)(C)C)C(=O)NS(=O)c1cccc(F)c1] |
| 3.11 | B | 1.2 | 2.1 | 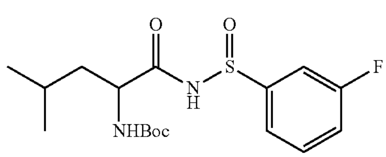 [SMILES: CC(C)CC(NC(=O)OC(C)(C)C)C(=O)NS(=O)c1cccc(F)c1] |
| 3.12 | B | 1.3 | 2.1 | 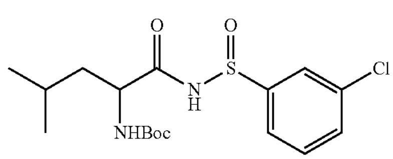 [SMILES: CC(C)CC(NC(=O)OC(C)(C)C)C(=O)NS(=O)c1cccc(Cl)c1] |

TABLE 3-continued

| Cmpd. No. | Method | Precursor 1 | Precursor 2 | Structure |
| --- | --- | --- | --- | --- |
| R-3.12 | B | R-1.3 | 2.1 | Leu(NHBoc)-C(O)NH-S(O)-(3-Cl-C6H4) |
| 3.13 | B | 1.4 | 2.1 | Leu(NHBoc)-C(O)NH-S(O)-(3-Me-C6H4) |
| 3.14 | B | 1.5 | 2.1 | Leu(NHBoc)-C(O)NH-S(O)-(3-OMe-C6H4) |
| 3.15 | B | 1.6 | 2.1 | Leu(NHBoc)-C(O)NH-S(O)-(3-Br-C6H4) |
| 3.16 | B | 1.7 | 2.1 | Leu(NHBoc)-C(O)NH-S(O)-(3-vinyl-C6H4) |
| 3.17 | B | 1.8 | 2.1 | Leu(NHBoc)-C(O)NH-S(O)-(3-Ph-C6H4) |
| 3.18 | B | 1.9 | 2.1 | Leu(NHBoc)-C(O)NH-S(O)-(3-CF3-C6H4) |
| 3.19 | B | 1.10 | 2.1 | Leu(NHBoc)-C(O)NH-S(O)-(3-CN-C6H4) |
| 3.20 | B | 1.11 | 2.1 | Leu(NHBoc)-C(O)NH-S(O)-(3-OCF3-C6H4) |
| 3.23 | B | 1.14 | 2.1 | Leu(NHBoc)-C(O)NH-S(O)-(3-CH2OMe-C6H4) |

TABLE 3-continued

| Cmpd. No. | Method | Precursor 1 | Precursor 2 | Structure |
|---|---|---|---|---|
| 3.24 | B | 1.15 | 2.1 | 3-iodophenyl sulfonamide of N-Boc-leucine |
| 3.25 | B | 1.16 | 2.1 | 3-(methylthio)phenyl sulfonamide of N-Boc-leucine |
| 3.26 | B | 1.17 | 2.1 | 3-(1-methyl-1H-pyrazol-3-yl)phenyl sulfonamide of N-Boc-leucine |
| 3.27 | B | 1.18 | 2.1 | 3-((trimethylsilyl)ethynyl)phenyl sulfonamide of N-Boc-leucine |
| 3.28 | B | 1.19 | 2.1 | 4-tert-butylphenyl sulfonamide of N-Boc-leucine |
| 3.29 | B | 1.20 | 2.1 | 4-fluorophenyl sulfonamide of N-Boc-leucine |
| 3.30 | B | 1.21 | 2.1 | 2-cyanophenyl sulfonamide of N-Boc-leucine |
| 3.31 | B | 1.22 | 2.1 | 2-fluorophenyl sulfonamide of N-Boc-leucine |
| 3.32 | B | 1.23 | 2.1 | 2-chlorophenyl sulfonamide of N-Boc-leucine |
| 3.33 | B | 1.24 | 2.1 | 2-nitrophenyl sulfonamide of N-Boc-leucine |

TABLE 3-continued
| Cmpd. No. | Method | Precursor 1 | Precursor 2 | Structure |
|---|---|---|---|---|
| 3.34 | B | 1.25 | 2.1 | 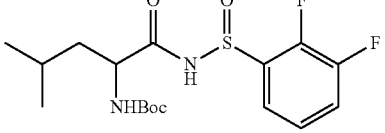 |
| 3.35 | B | 1.26 | 2.1 | 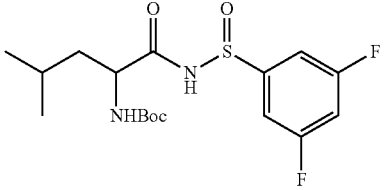 [SMILES: CC(C)CC(NC(=O)OC(C)(C)C)C(=O)NS(=O)c1cc(F)cc(F)c1] |
| 3.36 | B | 1.27 | 2.1 | 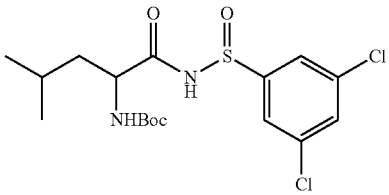 [SMILES: CC(C)CC(NC(=O)OC(C)(C)C)C(=O)NS(=O)c1cc(Cl)cc(Cl)c1] |
| 3.37 | B | 1.28 | 2.1 | 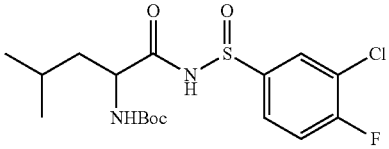 [SMILES: CC(C)CC(NC(=O)OC(C)(C)C)C(=O)NS(=O)c1ccc(F)c(Cl)c1] |
| 3.38 | B | 1.29 | 2.1 | 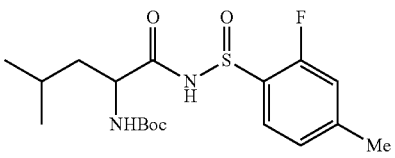 [SMILES: Cc1ccc(S(=O)NC(=O)C(CC(C)C)NC(=O)OC(C)(C)C)c(F)c1] |
| 3.39 | B | 1.30 | 2.1 | 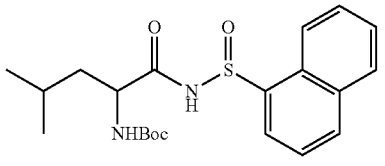 [SMILES: CC(C)CC(NC(=O)OC(C)(C)C)C(=O)NS(=O)c1cccc2ccccc12] |
| 3.40 | B | 1.31 | 2.1 | 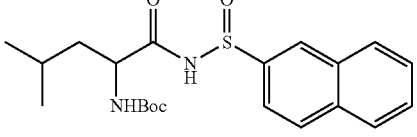 |
| 3.41 | B | 1.33 | 2.1 | 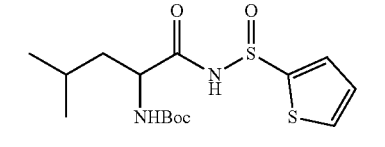 [SMILES: CC(C)CC(NC(=O)OC(C)(C)C)C(=O)NS(=O)c1cccs1] |
| 3.42 | B | 1.33 | 2.1 | 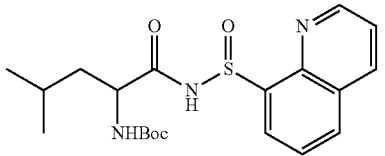 [SMILES: CC(C)CC(NC(=O)OC(C)(C)C)C(=O)NS(=O)c1cccc2cccnc12] |

TABLE 3-continued

| Cmpd. No. | Method | Precursor 1 | Precursor 2 | Structure |
|---|---|---|---|---|
| 3.43 | B | 1.34 | 2.1 | *leucine-NHBoc derivative with N-sulfinyl-2-pyridyl group* |
| 3.44 | B | 1.35 | 2.1 | *leucine-NHBoc derivative with N-sulfinyl-2-furyl group* |

General Method C:

Exemplified for the synthesis of 2-amino-4-methyl-N-phenylsulfinyl)pentanamide diastereomers R-4.1 and S-4.1

Intermediate 3.1 was dissolved in neat trifluoroacetic acid (TFA) and the mixture was stirred overnight at room temperature. The mixture was concentrated in vacuo and the diastereomers were separated by reverse phase chromatography on C18 silica gel eluting with a mixture of acetonitrile and water (acetonitrile gradient 5%-35%) to give a first diastereomer R-4.1 as a fast eluting diastereomer and a second diastereomer S-4.1 as a slow eluting diastereomer.

First diastereomer (R-4.1): 1H-NMR (400 MHz, DMSO-d6) δ: 8.28 (1H, br s); 7.71-7.68 (2H, m); 7.65-7.62 (3H, m); 3.81 (1H, dd, J=5.6, 8.5 Hz); 1.70-1.50 (3H, m); 0.86 (3H, d, J=6.4 Hz); 0.84 ppm (3H, d, J=6.4 Hz). LC/MS 255 (M+1).

Second diastereomer (S-4.1): 1H-NMR (400 MHz, DMSO-d6) δ: 8.92 (1H, br s); 7.73-7.71 (2H, m); 7.67-7.62 (3H, m); 3.79 (1H, broad t, J=6.3 Hz); 1.73-1.50 (3H, m); 0.87 (3H, d, J=5.7 Hz); 0.85 ppm (3H, d, J=5.6 Hz). LC/MS 255 (M+1).

The configuration of isomers were assigned by comparing with samples prepared from diastereomerically pure intermediates R-3.1 and S-3.1 as exemplified by the synthesis of (S)-4-methyl-1-oxo-1-(((R)-phenylsulfinyl)amino)pentan-2-aminium 2,2,2-trifluoroacetate (R-4.1).

Tert-butyl ((S)-4-methyl-1-oxo-1-(((R)-phenylsulfinyl)amino)pentan-2-yl)carbamate (R-3.1) (361 mg, 1.0 mmol) was dissolved in TFA (3 mL). The resulting solution was stirred at room temperature for 2 hours (TLC showed complete conversion). The reaction mixture was evaporated to dryness. The residue was treated with Et$_2$O (10 mL), and the resulting solids were filtered and washed with cold Et$_2$O (5 mL) to give 251 mg (67%) of (S)-4-methyl-1-oxo-1-(((R)-phenylsulfinyl)amino)pentan-2-aminium 2,2,2-trifluoroacetate (R-4.1) as a white solid.

The following compounds were obtained (in the form of TFA salt) using methods analogous to Method C:

TABLE 4

| Cmpd. No. | Method | Precursor | Structure |
|---|---|---|---|
| R-4.1 | C | 3.1, R-3.1 | *leucinamide with N-(R)-phenylsulfinyl, NH$_2$* |
| S-4.1 | C | 3.1, S-3.1 | *leucinamide with N-(R)-phenylsulfinyl, NH$_2$* |
| 4.2 | C | 3.2 | *isoleucine-like amide with N-phenylsulfinyl, NH$_2$* |
| 4.3 | C | 3.3 | *methionine amide with N-phenylsulfinyl, NH$_2$* |

TABLE 4-continued

| Cmpd. No. | Method | Precursor | Structure |
|---|---|---|---|
| 4.4 | C | 3.4 | (2-aminopentanoyl)benzenesulfonamide |
| 4.5 | C | 3.5 | (2-amino-3-methylbutanoyl)benzenesulfonamide |
| 4.6 | C | 3.6 | (S)-(2-amino-4-methylpentanoyl)benzenesulfonamide |
| 4.7 | C | 3.7 | (2-amino-2,4-dimethylpentanoyl)benzenesulfonamide |
| 4.8 | C | 3.8 | (2-amino-3-phenylpropanoyl)benzenesulfonamide |
| 4.9 | C | 3.9 | (2-amino-2-phenylacetyl)benzenesulfonamide |
| 4.10 | C | 3.10 | (2-aminobutanoyl)-3-fluorobenzenesulfonamide |
| 4.11 | C | 3.11 | (2-amino-4-methylpentanoyl)-3-fluorobenzenesulfonamide |
| 4.12 | C | 3.12 | (2-amino-4-methylpentanoyl)-3-chlorobenzenesulfonamide |
| R-4.12 | C | R-3.12 | (S)-(2-amino-4-methylpentanoyl)-(R)-3-chlorobenzenesulfonamide |

TABLE 4-continued

| Cmpd. No. | Method | Precursor | Structure |
|---|---|---|---|
| 4.13 | C | 3.13 | Leucinamide-N-S(O)-(3-methylphenyl) sulfonimide |
| 4.14 | C | 3.14 | Leucinamide-N-S(O)-(3-methoxyphenyl) sulfonimide |
| 4.15 | C | 3.15 | Leucinamide-N-S(O)-(3-bromophenyl) sulfonimide |
| 4.16 | C | 3.16 | Leucinamide-N-S(O)-(3-vinylphenyl) sulfonimide |
| 4.17 | C | 3.17 | Leucinamide-N-S(O)-(3-phenylphenyl) sulfonimide |
| 4.18 | C | 3.18 | Leucinamide-N-S(O)-(3-CF$_3$-phenyl) sulfonimide |
| 4.19 | C | 3.19 | Leucinamide-N-S(O)-(3-cyanophenyl) sulfonimide |
| 4.20 | C | 3.20 | Leucinamide-N-S(O)-(3-OCF$_3$-phenyl) sulfonimide |
| 4.21 | C | 3.21 | Leucinamide-N-S(O)-(3-COOMe-phenyl) sulfonimide |
| 4.22 | C | 3.22 | Leucinamide-N-S(O)-(3-NHMe-phenyl) sulfonimide |

TABLE 4-continued

| Cmpd. No. | Method | Precursor | Structure |
|---|---|---|---|
| 4.23 | C | 3.23 | Leucinamide-N(H)-S(=O)-phenyl-3-CH2OMe |
| 4.24 | C | 3.24 | Leucinamide-N(H)-S(=O)-phenyl-3-I |
| 4.25 | C | 3.25 | Leucinamide-N(H)-S(=O)-phenyl-3-SMe |
| 4.26 | C | 3.26 | Leucinamide-N(H)-S(=O)-phenyl-3-(1-methylpyrazol-3-yl) |
| 4.27 | C | 3.27 | Leucinamide-N(H)-S(=O)-phenyl-3-C≡CH |
| 4.28 | C | 3.28 | Leucinamide-N(H)-S(=O)-phenyl-4-tBu |
| 4.29 | C | 3.29 | Leucinamide-N(H)-S(=O)-phenyl-4-F |
| 4.30 | C | 3.30 | Leucinamide-N(H)-S(=O)-phenyl-2-CN |
| 4.31 | C | 3.31 | Leucinamide-N(H)-S(=O)-phenyl-2-F |
| 4.32 | C | 3.32 | Leucinamide-N(H)-S(=O)-phenyl-2-Cl |

TABLE 4-continued

| Cmpd. No. | Method | Precursor | Structure |
|---|---|---|---|
| 4.33 | C | 3.33 | Leucyl-NH-S(=O)-(2-nitrophenyl) |
| 4.34 | C | 3.34 | Leucyl-NH-S(=O)-(2,3-difluorophenyl) |
| 4.35 | C | 3.35 | Leucyl-NH-S(=O)-(3,5-difluorophenyl) |
| 4.36 | C | 3.36 | Leucyl-NH-S(=O)-(3,5-dichlorophenyl) |
| 4.37 | C | 3.37 | Leucyl-NH-S(=O)-(3-chloro-4-fluorophenyl) |
| 4.38 | C | 3.38 | Leucyl-NH-S(=O)-(2-fluoro-4-methylphenyl) |
| 4.39 | C | 3.39 | Leucyl-NH-S(=O)-(naphthalen-1-yl) |
| 4.40 | C | 3.40 | Leucyl-NH-S(=O)-(naphthalen-2-yl) |
| 4.41 | C | 3.41 | Leucyl-NH-S(=O)-(thiophen-2-yl) |

TABLE 4-continued

| Cmpd. No. | Method | Precursor | Structure |
|---|---|---|---|
| 4.42 | C | 3.42 | *(structure: leucine amide N-sulfinyl quinolin-8-yl)* |
| 4.43 | C | 3.43 | *(structure: leucine amide N-sulfinyl pyridin-2-yl)* |
| 4.44 | C | 3.44 | *(structure: leucine amide N-sulfinyl furan-2-yl)* |

General Method D:

Exemplified by the Synthesis of sodium 3-fluorobenzenesulfinate (6.2)

A solution of sodium sulfite (2.84 g, 22.5 mmol) in $H_2O$ (30 mL) was stirred at room temperature for 10 minutes. Base, such as sodium carbonate (3.18 g, 30.0 mmol), was added to the stirred solution. The resulting solution was stirred at elevated temperature, such as 50° C. for 10 minutes. 3-Fluorobenzenesulfonyl chloride 5.2 (2.0 mL, 15.0 mmol) was added dropwise to the solution and was stirred at 50° C. for 2 hours. The reaction mixture was evaporated to dryness and re-dissolved in EtOH (50 mL). The suspension was stirred at room temperature for 20 minutes. The suspension was filtered and the filtrate evaporated to afford a white solid, which was stirred with MeCN (20 mL) and then filtered to afford sodium 3-fluorobenzenesulfinate 6.2 (2.68 g, 98%) as a white solid.

$^1$H NMR (400 MHz, DMSO-$d_6$) δ: 7.36 (m, 1H), 7.29 (m, 1H), 7.21 (m, 1H) and 7.03 (m, 1H).

The following compounds were obtained using methods analogous to Method D (using the indicated base at the indicated temperature):

TABLE 5

| Cmpd. No. | Method | Base | Temp (° C.) | Precursor | Structure |
|---|---|---|---|---|---|
| 6.2 | D | $Na_2CO_3$ | 50 | 5.2 | *(sodium 3-fluorobenzenesulfinate)* |
| 6.3 | D | $Na_2CO_3$ | 50 | 5.3 | *(sodium 3-chlorobenzenesulfinate)* |
| 6.4 | D | $Na_2CO_3$ | 50 | 5.4 | *(sodium 3-methylbenzenesulfinate)* |
| 6.5 | D | $Na_2CO_3$ | 50 | 5.5 | *(sodium 3-methoxybenzenesulfinate)* |

TABLE 5-continued
| Cmpd. No. | Method | Base | Temp (° C.) | Precursor | Structure |
|---|---|---|---|---|---|
| 6.6 | D | Na$_2$CO$_3$ | 50 | 5.6 | 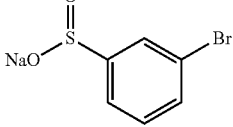 |
| 6.7 | D | Na$_2$CO$_3$ | 50 | 5.7 | 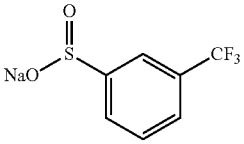 |
| 6.8 | D | Na$_2$CO$_3$ | 50 | 5.8 | 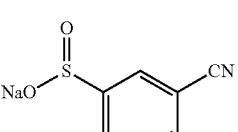 |
| 6.9 | D | Na$_2$CO$_3$ | 70 | 5.9 | 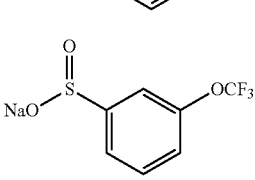 |
| 6.10 | D | Na$_2$CO$_3$ | 50 | 5.10 | 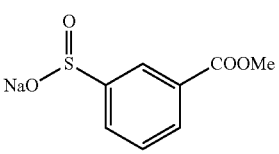 |
| 6.11 | D | Na$_2$CO$_3$ | 50 | 5.11 | 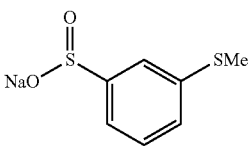 |
| 6.12 | D | Na$_2$CO$_3$ | 50 | 5.12 | 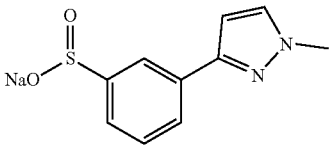 |
| 6.13 | D | Na$_2$CO$_3$ | 50 | 5.13 | 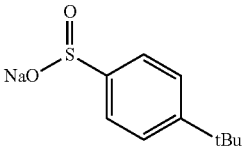 |
| 6.14 | D | Na$_2$CO$_3$ | 50 | 5.14 | 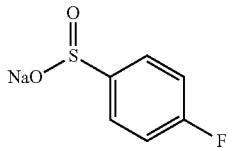 |
| 6.15 | D | NaHCO$_3$ | 80 | 5.15 | 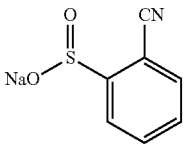 |

TABLE 5-continued

| Cmpd. No. | Method | Base | Temp (° C.) | Precursor | Structure |
|---|---|---|---|---|---|
| 6.16 | D | $Na_2CO_3$ | 50 | 5.16 | sodium 2-fluorobenzenesulfinate |
| 6.17 | D | $Na_2CO_3$ | 50 | 5.17 | sodium 2-chlorobenzenesulfinate |
| 6.18 | D | $Na_2CO_3$ | 50 | 5.18 | sodium 2-nitrobenzenesulfinate |
| 6.19 | D | $Na_2CO_3$ | 50 | 5.19 | sodium 2,3-difluorobenzenesulfinate |
| 6.20 | D | $Na_2CO_3$ | 50 | 5.20 | sodium 3,5-difluorobenzenesulfinate |
| 6.21 | D | $Na_2CO_3$ | 50 | 5.21 | sodium 3,5-dichlorobenzenesulfinate |
| 6.22 | D | $Na_2CO_3$ | 70 | 5.22 | sodium 3-chloro-4-fluorobenzenesulfinate |
| 6.23 | D | $Na_2CO_3$ | 70 | 5.23 | sodium 2-fluoro-4-methylbenzenesulfinate |
| 6.24 | D | $Na_2CO_3$ | 50 | 5.24 | sodium naphthalene-1-sulfinate |

TABLE 5-continued

| Cmpd. No. | Method | Base | Temp (° C.) | Precursor | Structure |
|---|---|---|---|---|---|
| 6.25 | D | Na₂CO₃ | 50 | 5.25 | NaO-S(=O)-2-naphthyl |
| 6.26 | D | Na₂CO₃ | 50 | 5.26 | NaO-S(=O)-2-thienyl |
| 6.27 | D | Na₂CO₃ | 70 | 5.27 | NaO-S(=O)-quinolin-8-yl |
| 6.28 | D | Na₂CO₃ | 70 | 5.28 | NaO-S(=O)-pyridin-2-yl |
| 6.29 | D | Na₂CO₃ | 50 | 5.29 | NaO-S(=O)-2-furyl |
| 6.30 | D | Na₂CO₃ | 50 | 5.30 | NaO-S(=O)-(3-(methoxymethyl)phenyl) |

General Method E:

Exemplified by the Synthesis of Benzenesulfinamide (1.1)

Sodium benzenesulfinate 6.1 (1.0 g, 6.1 mmol) was dissolved in dry toluene (20 mL) under an argon atmosphere and the solution was cooled in an ice bath. Oxalyl chloride (0.45 mL, 5.2 mmol) was added dropwise over 5 minutes. The mixture was heated to room temperature and then stirred for 2 hours at room temperature. A mixture of concentrated aqueous NH₄OH (20 mL) and EtOAc (15 mL) was added and the resulting suspension was stirred for 1 hour. The mixture was extracted with EtOAc (3×10 mL) and the combined organic phase was washed with saturated aqueous NaCl solution and dried over Na₂SO₄. Solvent was evaporated from the extract and the residue was purified by flash chromatography on silica gel eluting with a mixture of light petroleum ether and EtOAc (1:1) to give intermediate 1.1 (0.40 g, 46.5%).

1H NMR (400 MHz, DMSO-d₆) δ: 7.64-7.67 (2H, m), 7.48-7.56 (3H, m), 6.24 (2H, brs).

The following compounds were obtained using methods analogous to Method E:

TABLE 6

| Compound No. | Method | Precursor | Structure |
|---|---|---|---|
| 1.1 | E | 6.1 | H₂N-S(=O)-phenyl |
| 1.2 | E | 6.2 | H₂N-S(=O)-(3-fluorophenyl) |
| 1.4 | E | 6.4 | H₂N-S(=O)-(3-methylphenyl) |

TABLE 6-continued

| Compound No. | Method | Precursor | Structure |
|---|---|---|---|
| 1.5 | E | 6.5 | 3-methoxy phenyl sulfinamide |
| 1.6 | E | 6.6 | 3-bromo phenyl sulfinamide |
| 1.9 | E | 6.7 | 3-CF₃ phenyl sulfinamide |
| 1.10 | E | 6.8 | 3-CN phenyl sulfinamide |
| 1.12 | E | 6.10 | 3-COOMe phenyl sulfinamide |
| 1.14 | E | 6.30 | 3-CH₂OMe phenyl sulfinamide |
| 1.15 | E | 13 | 3-iodo phenyl sulfinamide |
| 1.16 | E | 6.11 | 3-SMe phenyl sulfinamide |
| 1.17 | E | 6.12 | 3-(1-methylpyrazol-3-yl) phenyl sulfinamide |
| 1.19 | E | 6.13 | 4-tBu phenyl sulfinamide |
| 1.20 | E | 6.14 | 4-F phenyl sulfinamide |
| 1.21 | E | 6.15 | 2-CN phenyl sulfinamide |
| 1.22 | E | 6.16 | 2-F phenyl sulfinamide |
| 1.23 | E | 6.18 | 2-Cl phenyl sulfinamide |
| 1.25 | E | 6.19 | 2,3-difluoro phenyl sulfinamide |
| 1.26 | E | 6.20 | 3,5-difluoro phenyl sulfinamide |
| 1.27 | E | 6.23 | 3,5-dichloro phenyl sulfinamide |
| 1.30 | E | 6.24 | naphthalen-1-yl sulfinamide |

TABLE 6-continued

| Compound No. | Method | Precursor | Structure |
|---|---|---|---|
| 1.31 | E | 6.25 | H2N-S(=O)-2-naphthyl |
| 1.32 | E | 6.26 | H2N-S(=O)-2-thienyl |

General Method F:

Exemplified by the Synthesis of methyl 3-chlorobenzenesulfinate (7.1)

Sodium 3-chlorobenzenesulfinate 6.3 (941 mg, 4.7 mmol) was dissolved in dry toluene (20 mL) under an argon atmosphere and the solution was cooled in an ice bath. Oxalyl chloride (0.44 mL, 5.0 mmol) was added dropwise. The mixture was warmed up to room temperature and then stirred for 1 hour at room temperature. MeOH (1.5 mL, 47.0 mmol) was added to the mixture and the resulting suspension was stirred for 1 hour. The mixture was extracted with EtOAc (3×20 mL) and the combined organic phase was washed with saturated aqueous NaCl solution and dried over $Na_2SO_4$. Solvent was evaporated to give 898 mg (99%) of methyl 3-chlorobenzenesulfinate 7.1 as a colorless oil. The product was used without further purification.

1H NMR (400 MHz, $CDCl_3$) δ 7.71 (s, 1H), 7.60-7.47 (m, 3H), 3.51 (s, 3H).

The following compounds were obtained using methods analogous to Method F:

TABLE 7

| Compound No. | Method | Precursor | Structure |
|---|---|---|---|
| 7.1 | F | 6.3 | MeO-S(=O)-(3-Cl-phenyl) |
| 7.2 | F | 6.9 | MeO-S(=O)-(3-OCF3-phenyl) |
| 7.3 | F | 6.18 | MeO-S(=O)-(2-NO2-phenyl) |

TABLE 7-continued

| Compound No. | Method | Precursor | Structure |
|---|---|---|---|
| 7.4 | F | 6.22 | MeO-S(=O)-(3-Cl-4-F-phenyl) |
| 7.5 | F | 6.23 | MeO-S(=O)-(2-F-4-Me-phenyl) |
| 7.6 | F | 6.27 | MeO-S(=O)-(8-quinolinyl) |
| 7.7 | F | 6.28 | MeO-S(=O)-(2-pyridyl) |
| 7.8 | F | 6.29 | MeO-S(=O)-(2-furyl) |

General Method G:

Exemplified by the Synthesis of 2-nitrobenzenesulfinamide (1.24)

A solution of methyl 2-nitrobenzenesulfinate 7.3 (908 mg, 4.5 mmol) in anhydrous THF (30 mL) was cooled to 78° C. by a dry-ice bath under an atmosphere of argon. A solution of $LiN(SiMe_3)_2$ in toluene (6.8 mL, 1 M, 6.8 mmol) was injected via a syringe. The mixture was stirred at 78° C. for about 2 hours. After the reaction was complete, an aqueous saturated solution of $NH_4Cl$ (19.0 mL) was added, and the dry-ice bath was removed. Stirring was continued for 2 hours, while the temperature was allowed to gradually to rise to room temperature. Ethyl acetate (30 mL) and water (30 mL) were added. The two phases were separated, and aqueous phase was extracted twice with ethyl acetate (2×30 mL). The extracts were combined, and washed successively with an aqueous saturated solution of $NaHCO_3$ (30 mL) and brine (30 mL). The organic phase was dried over anhydrous $MgSO_4$, and the solvent was evaporated. The product was treated with $Et_2O$ (30 mL), filtrated, and dried under reduced pressure to afford 566 mg (67%) of 2-nitrobenzene sulfinamide 1.24 as a light yellow powder.

$^1$H NMR (400 MHz, Methanol-$d_4$) δ 8.22 (dd, J=7.9, 1.3 Hz, 1H), 8.16 (dd, J=8.0, 1.1 Hz, 1H), 7.92 (td, J=7.8, 1.2 Hz, 1H), 7.81-7.70 (m, 1H), 4.84 (s, 2H, overlapped with $H_2O$).

The following compounds were obtained using methods analogous to Method G:

TABLE 8

| Compound No. | Method | Precursor | Structure |
|---|---|---|---|
| 1.3 | G | 7.1 | H₂N-S(=O)-C₆H₄-Cl (3-chloro) |
| 1.11 | G | 7.2 | H₂N-S(=O)-C₆H₄-OCF₃ (3-OCF₃) |
| 1.24 | G | 7.3 | H₂N-S(=O)-C₆H₄-NO₂ (2-NO₂) |
| 1.28 | G | 7.4 | H₂N-S(=O)-C₆H₃-Cl,F (3-Cl, 4-F) |
| 1.29 | G | 7.5 | H₂N-S(=O)-C₆H₃-F,Me (2-F, 4-Me) |
| R-1.1 | G | S-10.1 | H₂N-S(=O)-Ph |
| S-1.1 | G | R-10.1 | H₂N-S(=O)-Ph |
| R-1.3 | G | S-10.3 | H₂N-S(=O)-C₆H₄-Cl (3-Cl) |
| 1.33 | G | 7.6 | H₂N-S(=O)-quinolin-8-yl |
| 1.34 | G | 7.7 | H₂N-S(=O)-pyridin-2-yl |
| 1.35 | G | 7.8 | H₂N-S(=O)-furan-2-yl |

General Method H:

Exemplified with the Synthesis of N-benzyl-N-(1-phenylethyl)-benzenesulfonamides (R-9.1 and S-9.1)

A mixture of freshly prepared benzene sulfinic chloride 8.1 (1.28 g, 8 mmol) in toluene (20 mL) was added into a cooled solution of (R)—N-benzyl-1-phenylethanamine (2.03 g, 9.6 mmol) and triethylamine (2.2 mL, 16 mmol) in toluene (20 mL) over 15 minutes at 0° C. After the addition was finished, the ice bath was removed, and the mixture was stirred further for about 2 hours while the temperature was allowed to gradually rise to room temperature. An aqueous solution of citric acid (30 mL, 15% w/v) was added, and the mixture was vigorously stirred for 5 minutes. Two phases were separated, and the aqueous phase was extracted twice with toluene (2×20 mL). The extracts were combined, and washed successively with saturated aqueous solution of NaHCO₃ (20 mL) and brine (20 mL). The organic phase was dried over anhydrous Na₂SO₄, and the solvent was removed under reduced pressure to give a residue, which was purified by chromatography (eluent: EtOAc/hexane=1:16) to give (R,S)—N-Benzyl-N-(1-phenylethyl)benzenesulfinamide S-9.1 (1.31 g, 49%) and its diastereomer (R,R)—N-Benzyl-N-(1-phenylethyl)benzenesulfinamide R-9.1 (1.0 g, 37%).

(R,S)—N-Benzyl-N-(1-phenylethyl)benzenesulfinamide (S-9.1)

1H NMR (acetone-d6) 7.82 (dd, J=7.1, 1.4 Hz, 2H), 7.55-7.61 (m, 2H), 7.47-7.54 (m, 3H), 7.37 (t, J=7.7 Hz, 2H), 7.29 (t, J=7.3 Hz, 1H), 7.15-7.24 (m, 3H), 7.01 (dd, J=7.8, 1.8 Hz, 2H), 4.47 (q, J=7.2 Hz, 1H), 4.07 (d, J=15.2 Hz, 1H), 3.70 (d, J=15.2 Hz, 1H), 1.56 (d, J=7.2 Hz, 3H).

(R,R)—N-Benzyl-N-(1-phenylethyl)benzenesulfinamide (R-9.1)

1H NMR (acetone-d6) 7.63 (dd, J=8.1, 1.3 Hz, 2H), 7.47-7.58 (m, 3H), 7.20-7.37 (m, 8H), 7.16 (dd, J=8.0, 1.5 Hz, 2H), 4.44 (q, J=7.0 Hz, 1H), 4.05 (d, J=14.8 Hz, 1H), 3.98 (d, J=14.8 Hz, 1H), 1.74 (d, J=7.0 Hz, 3H).

The following compounds were obtained using methods analogous to Method H:

TABLE 9

| Compound No. | Method | Precursor | Structure |
|---|---|---|---|
| R-9.1 | H | 8.1 | (structure: phenyl-S(=O)-N(CH(Me)Ph)(CH2Ph)) |
| S-9.1 | H | 8.1 | (structure: phenyl-S(=O)-N(CH(Me)Ph)(CH2Ph), opposite stereochem) |
| R-9.3 | H | 8.3 | (structure: 3-Cl-phenyl-S(=O)-N(CH(Me)Ph)(CH2Ph)) |
| S-9.3 | H | 8.3 | (structure: 3-Cl-phenyl-S(=O)-N(CH(Me)Ph)(CH2Ph), opposite stereochem) |

General Method I:

Exemplified with the Synthesis of (R)-methyl benzenesulfinate (R-10.1)

(R,S)—N-Benzyl-N-(1-phenylethyl)benzenesulfinamide S-9.1 (1.0 g, 3.0 mmol) was dissolved in toluene (20 mL), after which methanol (0.36 mL, 9.0 mmol) was added, and the mixture was cooled to 5° C. with a salt-ice bath. A solution of BF$_3$·OEt$_2$ (0.56 mL, 4.5 mmol) in toluene (5 mL) was added dropwise over 5 minutes, and the mixture was stirred at 5° C. for about 2.5 hours. The reaction was monitored by TLC (EtOAc/hexane=1:6). After the mixture was diluted with toluene (20 mL), the reaction was quenched by adding an aqueous saturated solution of NaHCO$_3$ (10 mL). The organic phase was separated, and then washed successively with an aqueous solution of citric acid (20 mL, 15% w/v) and aqueous saturated solution of NaHCO$_3$ (5 mL). The organic phase was dried over anhydrous MgSO$_4$. The solvent was removed under reduced pressure to afford (R)-methyl benzenesulfinate R-10.1 (401 mg, 86%) as a colorless oil.

1H NMR (CDCl$_3$) 7.68-7.74 (m, 2H), 7.52-7.59 (m, 3H), 3.48 (s, 3H).

The following compounds were obtained using methods analogous to Method I:

TABLE 10

| Compound No. | Method | Precursor | Structure |
|---|---|---|---|
| S-10.1 | I | R-9.1 | (structure: phenyl-S(=O)-OMe) |
| R-10.1 | I | S-9.1 | (structure: phenyl-S(=O)-OMe) |
| S-10.3 | I | R-9.3 | (structure: 3-Cl-phenyl-S(=O)-OMe) |

Method J:

Synthesis of N-methyl-3-(methylamino)benzenesulfinamide (11)

To a mixture of 3-bromobenzenesulfinamide 1.6 (500 mg, 2.27 mmol) and copper powder (11.6 mg, 0.182 mmol) was added 40% aqueous methylamine (4 mL, 24 mmol). The reaction mixture was heated to 110° C. for 18 hours in a pressure tube. The reaction mixture was cooled to room temperature and extracted with EtOAc (4×20 mL). The combined organic layers were dried over anhydrous Na$_2$SO$_4$, filtered, and volatiles were evaporated under reduced pressure to give crude intermediate 11 (362 mg, 75%).

LCMS ESI (m/z): 183.1 [M−H]$^-$.

Method K:

Synthesis of 3-(methylamino)benzenesulfinamide (1.13)

To a mixture of N-methyl-3-(methylamino)benzenesulfinamide (319 mg, 1.73 mmol) and copper powder (5.5 mg, 0.086 mmol) was added 25% aqueous ammonia (4 mL). The reaction mixture was heated to 110° C. for 3 days in a pressure tube. The reaction mixture was cooled to room temperature and extracted with EtOAc (4×20 mL). Combined organic layers were directly evaporated on silica gel. The product was purified by silica gel column chromatography (gradient PE:EtOAc 1:1 to EtOAc 100%). Intermediate 1.13 was obtained (40.5 mg, 14%) as a yellow oil.

$^1$H NMR (400 MHz, Chloroform-d) δ 7.29-7.22 (m, 1H), 7.00-6.94 (m, 2H), 6.68-6.65 (m, 1H), 5.76 (s, 1H), 4.43 (s, 2H), 2.85 (s, 3H).

Method L:

Synthesis of 3-(vinyl)benzenesulfinamide (1.7)

A solution of potassium vinyltrifluoroborate (125 mg, 0.936 mmol), PdCl$_2$ (3.32 mg, 0.019 mmol), PPh$_3$ (14.73 mg, 0.056 mmol), Cs$_2$CO$_3$ (914 mg, 2.808 mmol), and 3-bromobenzenesulfinamide 1.6 (206 mg, 0.0936 mmol) in THF/H$_2$O (9:1) (4 mL) was heated at 85° C. under a nitrogen atmosphere in a sealed tube for 22 hours. The reaction mixture was cooled to room temperature, diluted with H$_2$O (10 mL), and extracted with CH$_2$Cl$_2$ (10 mL×3). The solvent was removed in vacuo, and the crude product was purified by silica gel chromatography (eluting with 2:1 petrol ether: acetone) to yield sulfinamide 1.7 (90 mg, 57.5%).

¹H-NMR (300 MHz, Chloroform-d) δ: 7.81 (s, 1H), 7.62 (dt, J=7.4, 1.6 Hz, 1H), 7.55-7.42 (m, 2H), 6.76 (dd, J=17.6, 10.9 Hz, 1H), 5.86 (d, J=17.6 Hz, 1H), 5.36 (d, J=10.9 Hz, 1H), 4.29 (broad s, 2H).

Method M:

Synthesis of 3-((trimethylsilyl)ethynyl)benzenesulfinamide (1.18)

The reaction was carried out in a pressure vial. Starting material 1.6 (0.372 g, 1.69 mmol) was dissolved in a triethylamine (5 mL)/toluene (5 mL) mixture. Argon was bubbled through the solution for 20 minutes and then CuI (0.048 g, 0.25 mmol) and (PPh$_3$)$_4$Pd (0.293 g, 0.25 mmol) were added followed by treatment of the suspension with argon for additional 5 minutes. Potassium vinyltrifluoroborate (0.830 g; 1.203 mL, 8.45 mmol) was added and the vial was closed and heated at 80° C. for 3 hours (using an oil bath). The dark mixture was cooled, diluted with EtOAc (60 mL), and filtered through a fine filter. The filtrate was evaporated and the residue was purified by flash chromatography on silica gel (Eluent: PE/EtOAc gradient from 100/0 to 100/50) to give the product 1.18 (0.277 g, 69%).

¹H-NMR (400 MHz, CDCl$_3$) δ: 7.84 (td, J=1.7; 0.5 Hz, 1H), 7.68 (ddd, J=7.9, 1.8, 1.2 Hz, 1H), 7.57 (ddd, J=7.7; 1.5; 1.2 Hz, 1H); 7.44 (td, J=7.8; 0.5 Hz; 1H); 4.40 (s, 2H); 0.25 (s, 9H). LCMS ESI (m/z): 238.598 [M+H⁺].

Method N:

Synthesis of 3-phenylbenzenesulfinamide (1.8)

A solution of phenylboronic acid (252 mg, 2.07 mmol), Na$_2$CO$_3$ (798 mg, 7.53 mmol) and 3-bromobenzenesulfinamide 1.6 (206 mg, 0.0936 mmol) in PhMe/EtOH/H$_2$O=2/1/1 (20 mL) was degassed with argon flow for 20 minutes. Tetrakis(triphenylphosphine palladium (0) (152.31 mg, 0.13 mmol) was added and the reaction mixture was heated at 90° C. under an argon atmosphere in a sealed tube overnight. The reaction mixture was cooled to room temperature, diluted with H$_2$O (10 mL), and exacted with EtOAc (10 mL×3). The solvent was removed in vacuo and the crude product was purified by silica gel chromatography (eluting with 2:1 petrol ether:acetone) to yield sulfinamide 1.8 (320 mg, 78.2%).

¹H NMR (300 MHz, Chloroform-d) δ 8.05-7.95 (m, 1H), 7.78-7.68 (m, 2H), 7.66-7.53 (m, 3H), 7.52-7.33 (m, 3H), 4.34 (broad s, 2H). LCMS ESI (m/z): 218.33 [M+H]+.

General Method O:

Exemplified by the Synthesis of lithium 3-iodobenzenesulfonate (13)

To a solution of 1,3-diiodobenzene 12 (4.00 g, 12.12 mmol) in dry THF (100 mL) was added 2.5 M n-butyllithium (4.85 mL, 12.12 mmol) in hexanes under an argon atmosphere at −78° C. The reaction mixture was stirred at this temperature for 30 minutes. Then, sulfur dioxide gas was bubbled into the mixture for 10 minutes. The reaction mixture was allowed to warm up to room temperature and solvents were evaporated under reduced pressure. The crude product was treated with hexane and filtered off to give intermediate (13) (3.322 g, quant.).

¹H NMR (400 MHz, D$_2$O) δ 7.85-7.81 (m, 1H), 7.71 (ddd, J=7.8, 1.8, 1.0 Hz, 1H), 7.48 (ddd, J=7.7, 1.6, 1.0 Hz, 1H), 7.15 (td, J=7.8, 0.4 Hz, 1H).

General Method P:

Exemplified by the Synthesis of ethyl 3-bromobenzenesulfonate (14)

To a solution of 3-bromobenzenesulphonyl chloride (5.6) (5.640 mL, 39.13 mmol) in dichloromethane (50 mL) was added ethanol (3.98 mL, 117 mmol), triethyl amine (10.9 mL, 78.3 mmol) and 4-dimethylaminopyridine (48 mg, 0.39 mmol). The reaction mixture was stirred for 2 hours at room temperature. Water (50 mL) was added to the reaction mixture. Phases were separated. The organic phase was washed with water (2×50 mL), dried over anhydrous Na$_2$SO$_4$, and the solvent was evaporated under reduced pressure to give intermediate (14) (10.37 g, quant.).

¹H NMR (400 MHz, Chloroform-d) δ 8.04 (td, J=1.8, 0.4 Hz, 1H), 7.83 (ddd, J=7.9, 1.8, 1.0 Hz, 1H), 7.76 (ddd, J=8.1, 2.0, 1.0 Hz, 1H), 7.42 (td, J=8.0, 0.4 Hz, 1H), 4.15 (q, J=7.1 Hz, 2H), 1.32 (t, J=7.1 Hz, 3H).

Method Q:

Synthesis of 3-(methylthio)benzenesulfonyl chloride (5.11)

To a solution of ethyl 3-bromobenzenesulfonate (2.19 g, 8.26 mmol) in dry THF (12 mL) was added 2.5 M n-butyllithium (4.96 mL, 9.91 mmol) under an argon atmosphere at −78° C. The reaction mixture was stirred for 20 minutes. To the reaction mixture, dimethyldisulfide (1.83 ml, 20.6 mmol) was added drop-wise at −78° C. The reaction mixture was stirred for 10 minutes, and then allowed to warm up to room temperature over 1 hour. The reaction mixture was quenched with water (3 mL) and the solvents were evaporated under reduced pressure. The resulting sticky oil was washed with Et$_2$O (50 mL). Crude lithium 3-(methylthio) benzenesulfonate was used in the next step. To the intermediate (~6.071 mmol) was added thionyl chloride (40 mL) and DMF (0.20 mL). The reaction mixture was stirred under reflux for 3.5 hours. Volatiles were evaporated under reduced pressure to give a yellow solid, and DCM (50 mL) was added. The crude product was evaporated on silica gel and purified by silica gel column chromatography (PE: EtOAc 2:1). The title compound (5.11) (635 mg, 47%) was obtained as a yellowish amorphous solid.

¹H NMR (400 MHz, Chloroform-d) δ 8.08 (ddd, J=8.1, 1.5, 0.4 Hz, 1H), 7.63 (ddd, J=8.1, 7.4, 1.5 Hz, 1H), 7.49-7.40 (m, 1H), 7.31 (ddd, J=8.1, 7.3, 1.2 Hz, 1H), 2.60 (s, 3H).

General Method R:

Exemplified for the Synthesis of 2,5-dioxopyrrolidin-1-yl 2-((tert-butoxycarbonyl)amino) butanoate (2.10)

Amino acid 15.10 (394 mg, 1.93 mmol) was dissolved in THF (15 mL) under an argon atmosphere. The solution was cooled in an ice bath and N-hydroxysuccinimide (334.7 mg, 2.91 mmol) was added followed by DCC (600 mg, 2.91 mmol). The mixture was stirred at room temperature for 90 minutes. The solvent was removed in vacuo and the residue was dissolved in acetone and cooled in the freezer. The precipitate was removed by the filtration and the solvent removed in vacuo. The crude activated ester 2.10 (450 mg, 77%) was used for the next step without additional purification.

The following compounds were obtained using methods analogous to Method R:

TABLE 11

| Compound No. | Method | Precursor | Structure |
|---|---|---|---|
| 2.1 | R | 15.1 | (isobutyl-CH-NHBoc-C(O)O-NHS) |
| 2.2 | R | 15.2 | (sec-butyl-CH-NHBoc-C(O)O-NHS) |
| 2.3 | R | 15.3 | (MeS-CH2CH2-CH-NHBoc-C(O)O-NHS) |
| 2.4 | R | 15.4 | (n-propyl-CH-NHBoc-C(O)O-NHS) |
| 2.5 | R | 15.5 | (isopropyl-CH-NHBoc-C(O)O-NHS) |
| 2.6 | R | 15.6 | (isobutyl-CH-NHBoc-C(O)O-NHS, (S)) |
| 2.7 | R | 15.7 | (isobutyl-C(Me)-NHBoc-C(O)O-NHS) |
| 2.8 | R | 15.8 | (benzyl-CH-NHBoc-C(O)O-NHS) |
| 2.9 | R | 15.9 | (phenyl-CH-NHBoc-C(O)O-NHS) |
| 2.10 | R | 15.10 | (ethyl-CH-NHBoc-C(O)O-NHS) |

All compounds were characterized by $^1$H-NMR spectroscopy performed on Varian Mercury spectrometer (400 MHz) with chemical shifts values (δ) in ppm relative to internal standard, and occasionally also by $^{13}$C-NMR spectroscopy, MS, or HRMS.

TABLE 12

| Cmpd. No. | Physicochemical characterization |
|---|---|
| R-4.1 | $^1$H-NMR (400 MHz, methanol-d$_4$) δ: 7.82-7.73 (m, 2H), 7.70-7.57 (m, 3H), 4.52 (s, 3H), 3.95-3.87 (m, 1H), 1.83-1.62 (m, 3H), 1.00 (d, J = 6.2 Hz, 3H), 0.96 (d, J = 6.3 Hz, 3H). $^{13}$C-NMR spectrum (100 MHz, methanol-d$_4$): 172.3, 143.7, 133.5, 130.6, 125.9, 53.24.52, 40.9, 25.3, 23.4, 21.4. LCMS ESI$^+$ (m/z): 255 [M + H]$^+$ |
| S-4.1 | $^1$H-NMR (400 MHz, methanol-d$_4$) δ: 7.81-7.73(m, 2H), 7.70-7.61 (m, 3H), 4.84 (s, 3H), 3.98-3.83 (m, 1H), 1.82-1.64 (m, 3H), 0.97 (dd, J = 7.3, 6.2 Hz, 6H). $^{13}$C-NMR spectrum (100 MHz, methanol-d$_4$) δ: 172.8, 143.9, 133.4, 130.7, 125.8, 53.4, 41.3, 25.4, 23.2, 21.6. LCMS ESI$^+$ (m/z): 255 [M + H]$^+$. |
| 4.2 | $^1$H-NMR spectrum (400 MHz, methanol-d$_4$) δ: 7.84-7.74 (m, 2H), 7.69-7.59 (m, 3H), 4.86 (s, 3H), 3.77 (d, J = 5.3 Hz, 1H), 2.08-1.91 (m, 1H), 1.64-1.47 (m, 1H), 1.32-1.12 (m, 1H), 1.07 (d, J = 7.0 Hz, 3H), 0.97 (t, J = 7.4 Hz, 3H). $^{13}$C-NMR spectrum (100 MHz, methanol-d$_a$) δ: 171.3, 143.7, 133.5, 130.6, 125.9, 59.2, 37.8, 24.9, 15.3, 11.6. UPLC-MS (m/z): 255 [M + H]$^+$; HRMS (ESI): m/z: calcd for C$_{12}$H$_{19}$N$_2$O$_2$S [M + H]$^+$: 255.1167, found: 255.1167. |

TABLE 12-continued

| Cmpd. No. | Physicochemical characterization |
|---|---|
| 4.3 | $^1$H-NMR spectrum (400 MHz, methanol-$d_4$) δ: 7.83-7.76 (m, 1H), 7.68-7.35 (m, 4H), 4.88 (s, 3H), 4.12-3.87 (m, 1H), 2.67-2.42 (m, 2H), 2.23-2.06 (m, 2H), 2.07 (s, 3H). $^{13}$C-NMR spectrum (100 MHz, methanol-$d_4$) δ: 172.0, 144.1, 133.4, 130.6, 129.5, 125.8, 125.2, 54.1, 31.8, 29.7, 15.2. |
| 4.4 | $^1$H-NMR spectrum (400 MHz, methanol-$d_4$) δ: 7.88-7.70 (m, 2H), 7.73-7.49 (m, 3H), 4.86 (s, 4H), 3.93-3.84 (m, 1H), 1.95-1.72 (m, 2H), 1.53-1.35 (m, 2H), 0.98 (t, J = 7.3 Hz, 3H). $^{13}$C-NMR spectrum (100 MHz, methanol-$d_4$) δ: 171.8, 143.7, 133.5, 130.6, 125.9, 54.6, 34.0, 18.9, 13.9. HRMS (ESI): m/z: calcd for $C_{11}H_{17}N_2O_2S$ [M + H]$^+$: 241.1011, found: 241.1004. |
| 4.5 | $^1$H-NMR spectrum (400 MHz, methanol-$d_4$) δ: 7.86-7.72 (m, 2H), 7.72-7.59 (m, 3H), 4.86 (s, 3H, overlapped with MeOH), 3.72 (d, J = 5.2 Hz, 1H), 2.34-2.16 (m, 1H), 1.09 (d, J = 7.0 Hz, 3H), 1.04 (d, J = 7.0 Hz, 3H). $^{13}$C-NMR spectrum (100 MHz, methanol-$d_4$) δ: 171.2, 143.7, 133.5, 130.7, 125.9, 59.7, 31.3, 19.0, 17.2. UPLC-MS (m/z): 241[M + H]$^+$ |
| 4.6 | $^1$H-NMR spectrum (400 MHz, methanol-$d_4$): 7.88-7.70 (m, 2H), 7.72-7.52 (m, 3H), 4.86 (s, 3H, overlapped with MeOH), 3.95-3.88 (m, 1H), 1.86-1.58 (m, 3H), 0.98 (dd, J = 15.0, 6.1 Hz, 6H). $^{13}$C-NMR spectrum (100 MHz, methanol-$d_4$): 172.4, 143.7, 133.5, 130.6, 125.9, 53.2, 40.9, 25.3, 23.4, 21.4. UPLC-MS (m/z): 255 [M + H]$^+$. |
| 4.7 | $^1$H-NMR (400 MHz, methanol-$d_4$) δ: 7.79-7.73 (m, 2H), 7.67-7.61 (m, 3H), 2.02-1.71 (m, 3H), 1.53 (d, J = 18.1 Hz, 2H), 1.01-0.88 (m, 6H). $^{13}$C-NMR (101 MHz, methanol-$d_4$) δ: 173.1, 173.1, 142.3, 142.0, 132.0, 131.8, 129.1, 129.1, 124.6, 124.4, 60.3, 44.8, 44.8, 23.5, 23.48 23.4, 23.3, 22.6, 22.5, 21.6, 21.5. UPLC-MS (m/z): 268.49 [M + H]$^+$ |
| 4.8 | $^1$H-NMR spectrum (400 MHz methanol-$d_4$) diastereomer mixture (~1:1) δ: 7.82-7.73 (m, 2H), 7.68-7.52 (m, 6H), 7.47-7.40 (m, 2H), 7.40-7.31 (m, 6H), 7.31-7.23 (m, 4H), 4.20-4.05 (m, 2H), 3.28 (dd, J = 14.4, 5.2 Hz, 1H), 3.19 (dd, J = 14.0, 6.6 Hz, 1H), 3.16-3.09 (m, 1H), 3.06 (dd, 14.4, 8.6 Hz, 1H). $^{13}$C-NMR spectrum (100 methanol-$d_4$) diastereomer mixture (~1:1) δ: 171.5, 171.2, 143.8, 143.4, 135.1, 134.8, 133.5, 133.3, 130.6, 130.6, 130.5, 130.5, 130.3, 130.2, 129.1, 125.9, 125.8, 116.8, 56.0, 55.9, 38.5, 37.8. HRMS (ESI) m/z: Calcd. for $C_{15}H_{17}N_2O_2S$ [M + H]$^+$ 289.1005, found 289.1004. |
| 4.9 | $^1$H-NMR spectrum (methanol-$d_4$) δ: 7.74-7.44(m, 10H), 5.11-4.95 (m, 1H). $^{13}$C-NMR spectrum (100 MHz, methanol-$d_4$) δ: 170.1, 143.6, 133.4, 132.7, 131.5, 130.7, 130.5, 130.5, 129.8, 125.8, 58.2. LCMS ESI (m/z): 275.3 [M + H]$^+$. HRMS (ESI) m/z: Calcd. for $C_{14}H_{15}N_2O_2S$ [M + H]$^+$ 275.0849, found 275.0865. |
| 4.10 | $^1$H-NMR (400 MHz, methanol-$d_4$) δ: 7.71 (td, J = 8.0, 5.5 Hz, 1H), 7.65-7.57 (m, 2H), 7.48-7.38 (m, 1H), 3.89 (t, J = 6.1 Hz, 1H), 1.95 (qq, J = 14.7, 7.5 Hz, 2H), 1.08 (t, J = 7.5 Hz, 4H). $^{13}$C-NMR (101 MHz, methanol-$d_4$) δ: 171.90, 171.62, 165.66, 163.17, 146.65, 146.59, 132.82, 132.74, 132.67, 132.56, 121.97, 121.94, 121.88, 121.85, 120.46, 120.24, 113.16, 113.05, 112.91, 112.80, 55.92, 55.70, 25.48, 25.25, 9.31, 9.09. (List of peaks, C-F coupling not solved). UPLC-MS (m/z): 245.47 [M + H]$^+$. |
| 4.11 | $^1$H-NMR (400 MHz, methanol-$d_4$) δ: 7.72-7.63 (m, 1H), 7.63-7.48 (m, 2H), 7.43-7.35 (m, 1H), 4.86 (s, 3H), 3.96-3.87 (m, 1H), 1.80-1.64 (m, 3H), 0.98 (dd, J = 14.1, 6.1 Hz, 6H). $^{13}$C-NMR (100 MHz, methanol-$d_4$) δ: 172.4, 164.4 (d, J = 250.3 Hz), 146.6 (d, J = 5.9 Hz), 132.7 (d, J = 7.8 Hz), 122.0 (d, J = 3.3 Hz), 120.3 (d, J = 21.8 Hz), 113.0 (d, J = 24.8 Hz), 53.3, 40.9, 25.3, 23.4, 21.4. HRMS (ESI): m/z: calcd for $C_{12}H_{18}N_2O_2SF$ [M + H]$^+$: 273.1073, found: 273.1072. |
| 4.12 | $^1$H-NMR (400 MHz, methanol-$d_4$) δ: 7.80 (s, 1H), 7.76-7.50 (m, 3H), 4.85 (s, 3H), overlapped with MeOH), 3.99-3.87 (m, 1H), 1.82-1.60 (m, 3H), 0.98 (dd, J = 14.0, 5.9 Hz, 6H). $^{13}$C-NMR (100 MHz, methanol-$d_4$) δ: 172.3, 146.1, 136.6, 133.4, 132.1, 125.9, 124.4, 53.3, 49.6, 49.4, 49.2, 40.89, 25.3, 23.4, 21.4. UPLC-MS (m/z): 289 [M + H]$^+$ |
| R-4.12 | $^1$H-NMR (400 MHz, methanol-$d_4$) δ: 7.80 (t, J = 1.6 Hz, 1H), 7.73-7.58 (m, 3H), 4.83 (s, 3H), 3.96-3.88 (m, 1H), 1.78-1.69 (m, 3H), 1.00 (d, J = 6.2 Hz, 3H), 0.97 (d, J = 6.2 Hz, 3H). $^{13}$C-NMR spectrum (100 MHz, methanol-$d_4$) δ: 172.3, 146.2, 136.6, 133.4, 132.1, 125.9, 124.4, 53.3, 40.9, 25.3, 23.4, 21.4. |
| 4.13 | $^1$H-NMR spectrum (400 MHz, methanol-$d_4$) δ: 7.69-7.39 (m, 4H), 4.86 (s, 3H), 3.97-3.84 (m, 1H), 2.46 (s, 3H), 1.81-1.63 (m, 3H), 0.98 (dd, J = 15.1, 6.1 Hz, 6H). $^{13}$C-NMR spectrum (100 MHz, Methanol-$d_4$) δ: 172.3, 143.5, 141.1, 134.2, 130.5, 126.0, 123.0, 53.2, 41.0, 25.3, 23.4, 21.4. HRMS (ESI): m/z: calcd for $C_{13}H_{21}N_2O_2S$ [M + H]$^+$: 269.1324, found: 269.1324. |
| 4.14 | $^1$H-NMR spectrum (400 MHz, methanol-$d_4$) δ: 7.53 (t, J = 8.0 Hz, 1H), 7.37-7.27 (m, 2H), 7.18 (ddd, J = 8.3, 2.5, 0.8 Hz, 1H), 4.86 (s, 3H), 3.97-3.89 (m, 1H), 3.88 (s, 3H), 1.82-1.64 (m, 3H), 0.98 (dd, J =+0 14.6, 6.2 Hz, 6H). $^{13}$C-NMR spectrum (100 MHz, methanol-$d_4$) δ: 172.4, 162.0, 145.0, 131.7, 119.3, 117.8, 110.7, 56.2, 53.2, 40.9, |

TABLE 12-continued

| Cmpd. No. | Physicochemical characterization |
|---|---|
| | 25.3, 23.4, 21.4. UPLC-MS (m/z): 285 [M + H]$^+$ HRMS (ESI) m/z: calcd for $C_{13}H_{21}N_2O_3S$ [M + H]$^+$: 285.1273 found: 285.1273. |
| 4.15 | $^1$H-NMR spectrum (400 MHz, methanol-$d_4$) δ: 7.94 (t, J = 1.8 Hz, 1H), 7.81 (ddd, J = 8.0, 1.9, 0.9 Hz, 1H), 7.74 (ddd, J = 7.8, 1.6, 1.0 Hz, 1H), 7.56 (t, J = 7.9 Hz, 1H), 4.85 (s, 3H, overlapped with MeOH), 3.98-3.85 (m, 1H), 1.80-1.66 (m, 3H), 0.99 (dd, J = 14.2, 6.1 Hz, 6H). $^{13}$C-NMR spectrum (100 MHz, methanol-$d_4$) δ: 172.3, 146.4, 136.4, 132.4, 128.8, 124.8, 124.3, 53.3, 40.9, 25.3, 23.4, 21.3. UPLC-MS (m/z): 333 [M]$^+$, HRMS (ESI): m/z: calcd. for $C_{12}H_{18}N_2O_2SBr$ [M + H]+: 333.0272, found: 333.0269. |
| 4.16 | $^1$H NMR (400 MHz, methanol-$d_4$) δ: 7.85 (s, 1H), 7.74-7.55 (m, 3H), 6.84 (dd, J = 17.6, 11.0 Hz, 1H), 5.93 (d, J = 17.6 Hz, 1H), 5.40 (d, J = 11.0 Hz, 1H), 3.95-3.87 (m, 1H), 1.81-1.65 (m, 3H), 0.98 (dd, J = 15.8, 5.9 Hz, 6H). $^{13}$C NMR (101 MHz, methanol-$d_4$) δ: 172.3, 144.2, 140.6, 136.7, 131.0, 130.8, 124.9, 123.1, 116.6, 53.2, 40.9, 25.3, 23.4, 21.3. UPLC-MS = 281.55 [M + H]$^+$ |
| 4.17 | $^1$H-NMR spectrum (400 MHz, methanol-$d_4$) δ: 8.02 (t, J = 1.7 Hz, 1H), 7.91 (dt, J = 7.3, 1.6 Hz, 1H), 7.78-7.65 (m, 4H), 7.53-7.46 (m, 2H), 7.44-7.38 (m, 1H), 3.95-3.88 (m, 1H), 1.80-1.66 (m, 3H), 0.98 (dd, J = 16.9, 6.1 Hz, 6H). $^{13}$C-NMR spectrum (100 MHz, methanol-$d_4$) δ: 172.3, 144.5, 144.0, 140.7, 131.9, 131.1, 130.2, 129.3, 128.0, 124.6, 124.0, 53.2, 40.9, 25.3, 23.4, 21.3. |
| 4.18 | $^1$H-NMR spectrum (400 MHz, methanol-$d_4$) δ: 8.10 (s, 1H), 8.03 (d, J = 7.8 Hz, 1H), 7.96 (d, J = 7.8 Hz, 1H), 7.85 (t, J = 7.8 Hz, 1H), 4.86 (s, 3H), 4.00-3.78 (m, 1H), 1.85-1.60 (m, 3H), 1.00 (d, J = 6.1 Hz, 3H), 0.96 (d, J = 6.1 Hz, 3H). $^{13}$C-NMR spectrum (100 MHz, methanol-$d_4$) δ: 172.4, 145.8, 132.8 (q, J = 33.1 Hz), 131.6, 130.0 (q, J = 3.8 Hz), 129.9, 125.0 (q, J = 271.9 Hz), 122.9 (q, J = 4.0 Hz), 53.3, 40.8, 25.3, 23.4, 21.3. |
| 4.19 | $^1$H-NMR spectrum (400 MHz, methanol-$d_4$) δ: 8.19-8.10 (m, 1H), 8.09-8.03 (m, 1H), 8.04-7.96 (m, 1H), 7.82 (t, J = 7.9 Hz, 1H), 4.86 (s, 3H), 3.97-3.87 (m, 1H), 1.81 -1.64 (m, 3H), 0.98 (dd, J = 13.9, 6.1 Hz, 6H). $^{13}$C-NMR spectrum (100 MHz, methanol-$d_4$) δ: 172.4, 146.2, 136.6, 131.6, 130.5, 129.8, 118.5, 114.8, 53.3, 40.8, 25.3, 23.4, 21.4. HRMS (ESI): m/z: calcd for $C_{13}H_{17}N_3O_2NaS$ [M + Na]$^+$: 302.0939, found: 302.0927. |
| 4.20 | $^1$H-NMR spectrum (400 MHz, methanol-$d_4$) δ: 7.86-7.65 (m, 3H), 7.61-7.50 (m, 1H), 3.97-3.88 (m, 1H), 1.81-1.66 (m, 3H), 1.00 (d, J = 6.0 Hz, 3H), 0.96 (d, J = 6.1 Hz, 3H). $^{13}$C-NMR spectrum (100 MHz, methanol-$d_4$) δ: 172.4, 151.0, 146.7, 132.6, 125.8, 124.9, 121.8 (q, J = 257.1 Hz), 118.6, 53.3, 40.9, 25.3, 23.4, 21.3. |
| 4.21 | $^1$H NMR (400 MHz, methanol-$d_4$) δ: 8.38-8.33 (m, 1H), 8.17 (dt, J = 7.7, 1.3 Hz, 1H), 7.96 (tdd, J = 7.6, 1.9, 1.1 Hz, 1H), 7.68 (td, J = 7.8, 2.3 Hz, 1H), 3.92 (s, 3H), 3.81-3.72 (m, 1H), 1.80-1.55 (m, 3H), 0.97 (d, J = 6.2 Hz, 3H), 0.94 (d, J = 6.0 Hz, 3H). $^{13}$C-NMR (101 MHz, methanol-$d_4$) δ: 172.6, 165.8, 144.9, 132.1, 131.1, 129.3, 129.0, 125.5, 52.4, 51.6, 39.9, 24.0, 21.9, 20.2. UPLC-MS (m/z): 313 [M + H]$^+$HRMS (ESI): m/z: calcd. for $C_{14}H_{21}N_2O_4S$ [M + H]+: 313.1222, found: 313.1223. |
| 4.22 | $^1$H NMR (400 MHz, methanol-$d_4$) δ: 7.35-7.26 (m, 1H), 6.96-6.89 (m, 1H), 6.90-6.85 (m, 1H), 6.83-6.77 (m, 1H), 3.98-3.82 (m, 1H), 2.79 (s, 3H), 1.90-1.53 (m, 3H), 1.01 -0.92 (m, 6H). $^{13}$C NMR (101 MHz, methanol-$d_4$) 1:1 mixture of diastereomers δ: 171.10, 170.85*, 151.06, 151.03*, 142.68, 142.60*, 129.71, 129.64*, 115.65, 115.63*, 111.20, 111.05*, 106.04, 105.91*, 51.86, 51.72*, 39.81, 39.54*, 28.81, 23.95, 23.86*, 21.98, 21.74*, 20.17, 19.90*. UPLC-MS (m/z): 284 [m + H]$^+$. HRMS (ESI): m/z: calcd for $C^{13}H_{22}N_3O_2S$ [M + H]$^+$: 284.1433, found: 284.1441. |
| 4.23 | $^1$H-NMR (400 MHz, methanol-$d_4$) δ: 7.77-7.72 (m, 1H), 7.70-7.64 (m, 1H), 7.62-7.54 (m, 2H), 4.54 (s, 2H), 3.95-3.85 (m, 1H), 3.41 (s, 3H), 1.77-1.63 (m, 3H), 0.98 (d, J = 6.1 Hz, 3H), 0.96-0.91 (m, 3H). $^{13}$C-NMR (101 MHz, methanol-$d_4$) δ: 172.32, 143.89, 141.81, 132.39, 130.60, 125.04, 124.62, 74.68, 58.75, 53.22, 40.93, 25.30, 23.40, 21.37. UPLC-MS (m/z): 299 [M + H]$^+$ |
| 4.24 | $^1$H-NMR spectrum (400 MHz, methanol-$d_4$) δ: (8.09 (s, 1H), 7.98 (ddd, J = 7.8, 1.7, 1.0 Hz, 1H), 7.74 (ddd, J = 7.9, 1.7, 1.0 Hz, 1H), 7.38 (t, J = 7.9 Hz, 1H), 3.90 (s, 1H), 1.80-1.59 (m, 3H), 0.96- 0.94 (d & d, J = 6.1 Hz, 6H). $^{13}$C-NMR spectrum (100 MHz, methanol-$d_4$) δ: 172.3, 146.0, 142.4, 134.5, 132.2, 125.3, 95.3, 53.3 40.9, 25.3, 23.4, 21.3. |
| 4.25 | $^1$H-NMR (400 MHz, methanol-$d_4$) δ: 7.97-7.92 (m, 1H), 7.63-7.57 (m, 1H), 7.57-7.51 (m, 1H), 7.50-7.44 (m, 1H), 3.97-3.79 (m, 1H), 2.56 (s, 3H), 2.54 (s, 3H), 1.77-1.65 (m, 3H), 1.01-0.90 (m, 6H). $^{13}$C-NMR (101 MHz, methanol-$d_4$) δ: 170.91, 170.88, 139.88, 139.81, 137.36, 137.18, 132.42, 127.96, 127.92, 125.91, 125.86, 124.65, 124.48, 51.92, 51.54, 39.60, 39.37, 23.96, 23.78, 22.03, 21.86, 19.95, 19.82, 15.33, 15.30. UPLC-MS (m/z): 301 [M + H]$^+$, HRMS (ESI): m/z: calcd. for $C_{13}H_{21}N_2O_2S_2$ [M + H]+: 301.1044, found: 301.1050. |

TABLE 12-continued

| Cmpd. No. | Physicochemical characterization |
|---|---|
| 4.26 | $^1$H-NMR spectrum (400 MHz, methanol-d$_4$) diastereomer mixture (~1:1) δ: 8.19-8.17 (m, 2H), 8.06-8.00 (m, 2H), 7.72-7.63 (m, 4H), 7.66 (d, J = 2.3 Hz, 2H), 6.72 (d, J = 2.3 Hz, 1H), 6.72 (d, J = 2.3 Hz, 1H), 3.96 (s, 6H), 3.96-3.85 (m, 2H), 1.81-1.62 (m, 6H), 1.03-0.92 (m, 12H). $^{13}$C-NMR spectrum (100 MHz methanol-d$_4$) diastereomer mixture (-1:1) δ: 172.7, 172.4, 151.2, 144.5, 136.4, 136.3, 133.9, 131.0, 131.0, 130.2, 124.7, 124.6, 122.5, 122.4, 104.3, 104.3, 53.4, 53.3, 41.3, 41.0, 39.1. LCMS ESI (m/z): 335.3 [M + H]$^+$. HRMS (ESI) m/z: Calculated for C$_{16}$H$_{23}$N$_4$O$_2$S [M + H]$^+$ 355.1536, found 355.1549. |
| 4.27 | $^1$H-NMR spectrum (400 MHz, methanol-d$_4$) δ: 7.86 (t, J = 1.5 Hz, 1H), 7.81-7.69 (m, 2H), 7.67-7.59 (m, 1H), 3.98-3.85 (m, 1H), 3.72 (s, 1H), 1.82-1.59 (m, 3H), 1.00 (d, J = 6.3 Hz, 3H), 0.96 (d, J = 6.3 Hz, 3H). $^{13}$C-NMR spectrum (100 MHz, Methanol-d$_4$) δ: 172.3, 144.5, 136.6, 130.8, 129.1, 126.1, 125.3, 82.8, 81.1, 53.3, 40.9, 25.3, 23.4, 21.3. |
| 4.28 | $^1$H NMR (400 MHz, methanol-d$_4$) δ:7.71 (m, 4H), 3.93 (s, 1H), 1.74 (m, 3H), 1.38 (s, 9H), 0.99 (dd, J = 14.9, 5.8 Hz, 6H). $^{13}$C NMR (100 MHz, methanol-d$_4$) δ: (racemic, mixture of diastereomers, list of peaks given) 172.97, 172.59, 172.28, 157.51, 140.43, 127.76, 127.66, 125.73, 125.64, 53.35, 53.18, 52.80, 41.74, 41.18, 40.96, 36.02, 31.62, 31.52, 31.40, 25.48, 25.38, 25.29, 23.39, 23.21, 23.09, 21.97, 21.52, 21.40. |
| 4.29 | $^1$H-NMR (400 MHz, methanol-d$_4$) δ: 7.91-7.70 (m, 2H), 7.47-7.31 (m, 2H), 4.86 (s, 3H), 3.94-3.88 (m, 1H), 1.79-1.67 (m, 3H), 1.00 (d, J = 6.1 Hz, 3H), 0.97 (d, J = 6.1 Hz, 3H). $^{13}$C-NMR (100 MHz, methanol-d$_4$) δ: 172.2, 166.5 (d, J = 251.5 Hz), 139.5 (d, J = 3.0 Hz), 128.6 (d, J = 9.3 Hz), 117.7 (d, J = 23.2 Hz), 53.2, 40.9, 25.3, 23.4, 21.3. |
| 4.30 | $^1$H-NMR (400 MHz, methanol-d$_4$) δ: 7.99 (ddd, J = 8.0, 1.2, 0.8 Hz, 1H), 7.83 (dt, J = 8.2, 0.8 Hz, 1H), 7.68 (ddd, J = 8.3, 7.1, 1.2 Hz, 1H), 7.47 (ddd, J = 8.0, 7.1, 0.9 Hz, 1H), 5.33 (dd, J = 10.4, 3.0 Hz, 1H), 1.87-1.63 (m, 3H), 1.06-0.95 (m, 6H). |
| 4.31 | $^1$H-NMR (400 MHz, methanol-d$_4$) δ: 8.01 -7.86 (m, 1H), 7.78-7.61 (m, 1H), 7.51 (td, J = 7.6, 1.0 Hz, 1H), 7.38-7.24 (m, 1H), 4.85 (s, 3H), 4.00-3.81 (m, 1H), 1.79-1.68 (m, 3H), 1.00 (d, J = 6.1 Hz, 3H), 0.96 (d, J = 6.1 Hz, 3H). $^{13}$C-NMR (100 MHz, methanol-d$_4$) δ: 172.3, 160.0 (d, J = 249.1 Hz), 135.8 (d, J = 7.8 Hz), 130.8 (d, J = 14.6 Hz), 127.6 (d, J = 1.2 Hz), 126.5 (d, J = 3.3 Hz), 117.4 (d, J = 20.0 Hz), 53.2, 41.0, 25.3, 23.4, 21.3. |
| 4.32 | $^1$H-NMR (400 MHz, methanol-d$_4$) δ: 8.07-7.98 (m, 1H), 7.68-7.61 (m, 2H), 7.61 -7.55 (m, 1H), 4.86 (s, 3H), 3.91 (dd, J = 9.7, 3.9 Hz, 1H), 1.81-1.65 (m, 3H), 0.99 (d, J = 6.1 Hz, 3H), 0.96 (d, J = 6.1 Hz, 3H). $^{13}$C-NMR (100 MHz, methanol-d$_4$) δ: 172.1, 141.1, 134.9, 132.5, 131.6, 129.1, 127.7, 53.0, 41.0, 25.3, 23.5, 21.2. |
| 4.33 | $^1$H-NMR (300 MHz, methanol-d$_4$) δ: 8.41 (q, J = 7.5, 6.4 Hz, 2H), 8.10 (t, J = 7.4 Hz, 1H), 7.93 (t, J = 7.7 Hz, 1H), 3.87 (d, J = 5.6 Hz, 1), 1.86-1.53 (m, 3H), 1.11 -0.81 (m, 6H). $^{13}$C-NMR (101 MHz, methanol-d$_4$) δ: 172.52, 172.16, 146.50, 146.42, 140.98, 140.88, 136.39, 134.32, 128.07, 128.01, 126.96, 126.76, 53.27, 52.99, 49.00, 41.44, 41.11, 25.33, 25.22, 23.34, 23.07, 21.51, 21.37. UPLC/ESI (m/z)-300.53 [M + H]$^+$ |
| 4.34 | $^1$H NMR (400 MHz, methanol-d$_4$) δ: 7.73-7.66 (m, 1H), 7.62-7.52 (m, 1H), 7.47 (ttd, J = 8.3, 4.3, 1.6 Hz, 1H), 3.94 (dt, J = 8.9, 4.8 Hz, 1H), 1.79-1.61 (m, 3H), 0.96 (dd, J = 12.8, 6.0 Hz, 6H). $^{13}$C NMR (101 MHz, methanol-d$_4$) δ: 172.64, 172.26, 152.87, 152.84, 152.75, 152.72, 150.37, 150.34, 150.25, 150.23, 150.19, 149.14, 149.00, 146.65, 146.55, 146.51, 146.41, 133.70, 133.58, 133.45, 126.86, 126.79, 126.75, 126.68, 122.78, 122.72, 122.60, 122.55, 122.51, 122.48, 53.40, 53.15, 41.23, 40.97, 25.35, 25.27, 23.39, 23.08, 21.60, 21.35. (list of peaks, C-F coupling not solved). |
| 4.35 | $^1$H-NMR (400 MHz, methanol-d$_4$) δ: 7.48-7.34 (m, 2H), 7.32-7.24 (m, 1H), 4.86 (s, 3H), 3.98-3.85 (m, 1H), 1.80-1.62 (m, 3H), 1.00 (d, J = 6.1 Hz, 3H), 0.97 (d, J = 6.1 Hz, 3H). $^{13}$C-NMR (100 MHz, methanol-d$_4$) δ: 172.4, 166.0 (d, JC-F = 11.5 Hz), 163.5 (d, JC-F = 11.5 Hz), 148.7 (t, JC-F = 7.4 Hz), 109.6 (d, JC-F = 8.3 Hz), 109.4 (d, JC-F = 8.3 Hz), 108.5 (t, JC-F = 26.0 Hz), 53.3, 40.8, 25.3, 23.4, 21.3. |
| 4.36 | $^1$H NMR (400 MHz, DMSO-d$_6$) δ: 7.93 (t, J = 1.7 Hz, 1H), 7.71 (d, J = 1.8 Hz, 2H), 3.83 (t, J = 6.9 Hz, 1H), 1.76-1.51 (m, 3H), 0.93-0.84 (m, 6H). $^{13}$C NMR (101 MHz, D$_2$O) δ: 172.0, 143.4, 135.7, 132.4, 123.3, 52.1, 39.0, 23.6, 21.8, 20.4. UPLC-MS/ESI m/z = 269.51 [M + H]$^+$ |

TABLE 12-continued

| Cmpd. No. | Physicochemical characterization |
|---|---|
| 4.37 | $^1$H-NMR spectrum (400 MHz, methanol-$d_4$) δ: 7.92 (dd, J = 6.7, 2.2 Hz, 1H), 7.79-7.71 (m, 1H), 7.53 (t, J = 8.7 Hz, 1H), 3.98-3.86 (m, 1H), 1.84-1.66 (m, 3H), 1.00 (d, J = 6.2 Hz, 3H), 0.97 (d, J = 6.2 Hz, 3H). $^{13}$C-NMR spectrum (100 MHz, Methanol-$d_4$) δ: 172.3, 161.6 (d, J = 253.7 Hz), 141.1 (d, J = 3.6 Hz), 128.7, 126.9 (d, J = 8.5 Hz), 123.5 (d, J = 19.0 Hz), 118.9 (d, J = 22.9 Hz), 53.3, 40.8, 25.3, 23.4, 21.3. |
| 4.38 | $^1$H-NMR spectrum (400 MHz, methanol-$d_4$) δ: 7.80 (t, J = 7.7 Hz, 1H), 7.32 (d, J = 7.9 Hz, 1H), 7.15 (d, J = 11.0 Hz, 1H), 4.00-3.85 (m, 1H), 2.46 (s, 3H), 1.81 -1.65 (m, 3H), 1.00 (d, J = 5.7 Hz, 3H), 0.96 (d, J = 5.7 Hz, 3H). $^{13}$C-NMR spectrum (100 MHz, methanol-$d_4$) δ: 172.1, 159.8 (d, J = 248.6 Hz), 158.2, 147.9 (d, J = 8.0 Hz), 127.3 (d, J = 1.6 Hz), 127.1 (d, J = 2.9 Hz), 117.8 (d, J = 19.8 Hz), 53.1, 41.0, 25.3, 23.4, 21.4 (d, J = 1.6 Hz), 21.3. |
| 4.39 | $^1$H-NMR (400 MHz, methanol-$d_4$) δ: 8.24 (dd, J = 7.3, 1.1 Hz, 1H), 8.18 (d, J = 8.3 Hz, 1H), 8.08-8.03 (m, 1H), 8.03-7.98 (m, 1H), 7.75 (dd, J = 8.1, 7.4 Hz, 1H), 7.68-7.63 (m, 2H), 4.87 (s, 3H), 3.89-3.76 (m, 1H), 1.82-1.63 (m, 3H), 0.98 (d, J = 6.0 Hz, 3H), 0.90 (d, J = 6.1 Hz, 3H). $^{13}$C-NMR (100 MHz, methanol-$d_4$) δ: 172.3, 138.3, 135.3, 134.1, 130.2, 130.0, 129.0, 128.2, 126.4, 124.9, 122.8, 53.1, 41.0, 25.2, 23.4, 21.3. HRMS (ESI): m/z: calcd for $C_{16}H_{21}N_2O_2S$ $[M + H]^+$ 305.1324, found 305.1317. |
| 4.40 | $^1$H-NMR (400 MHz, methanol-$d_4$) δ: 9.94 (s, 1H), 9.67 (d, J = 8.7 Hz, 1H), 9.63-9.53 (m, 2H), 9.29 (dd, J = 8.7, 1.8 Hz, 1H), 9.26-9.16 (m, 2H), 6.42 (s, 3H), 5.55-5.43 (m, 1H), 3.41-3.20 (m, 3H), 2.53 (dd, J = 19.0, 6.0 Hz, 6H). $^{13}$C-NMR (100 MHz, methanol-$d_4$) δ: 172.3, 140.7, 136.4, 134.1, 130.8, 129.8, 129.6, 129.2, 128.7, 126.8, 121.4, 53.2, 40.9, 25.3, 23.4, 21.4. |
| 4.41 | $^1$H NMR (400 MHz, DMSO-$d_6$) δ: 8.08 (s, 2H), 7.90 (s, 1H), 7.53 (s, 1H), 3.68 (t, J = 7.1 Hz, 1H), 1.65 (dp, J = 13.0, 6.6 Hz, 1H), 1.55 (td, J = 6.9, 2.2 Hz, 2H), 0.90 (dd, J = 6.4, 4.2 Hz, 6H). 13C NMR (100 MHz, DMSO-$d_6$) δ: 170.86, 126.01, 125.88, 125.52, 50.84, 23.64, 22.59, 21.83. HRMS (ESI) m/z: calcd for $C_{10}H_{17}N_2O_2S_2$ $[M + H]^+$ 261.0731, found 261.0734. |
| 4.42 | $^1$H-NMR spectrum (400 MHz, Methanol-$d_4$): δ 8.95-8.88 (m, 1H), 8.48 (d, J = 8.4 Hz, 1H), 8.40 (t, J = 6.6 Hz, 1H), 8.24 (d, J = 8.2 Hz, 1H), 7.88 (t, J = 7.7 Hz, 1H), 7.70-7.61 (m, 1H), 3.89-3.72 (m, 1H), 1.81-1.57 (m, 3H), 0.92 (m, 3H), 0.82 (m, 3H). $^{13}$C-NMR spectrum (100 MHz, Methanol-$d_4$): δ 172.1, 172.0, 152.3, 152.2, 145.4, 140.0, 138.0, 133.8, 130.2, 130.1, 128.7, 128.5, 127.6, 123.8, 53.0, 41.5, 41.1, 25.2, 23.4, 22.9, 21.7, 21.3. UPLC-MS (m/z): 306.5 $[M + H]^+$. |
| 4.43 | $^1$H NMR (400 MHz, Methanol-$d_4$) δ 10.27 (ddd, J = 4.7, 1.7, 0.9 Hz, 1H), 9.73-9.64 (m, 2H), 9.19 (ddd, J = 7.3, 4.7, 1.4 Hz, 1H), 5.59-5.43 (m, 1H), 3.36-3.23 (m, 3H), 2.56 (d, J = 6.2 Hz, 3H), 2.53 (d, J = 6.1 Hz, 3H). $^{13}$C NMR (101 MHz, Methanol-$d_4$) δ 172.4, 163.1, 151.3, 140.0, 127.7, 122.0, 53.3, 40.9, 25.3, 23.4, 21.4. UPLC-MS (m/z): 256.1 $[M + H]^+$. |
| 4.44 | $^1$H NMR (800 MHz, Methanol-$d_4$) δ 7.91 (d, J = 7.6 Hz, 1H), 7.26 - 7.08 (m, 1H), 6.75-6.70 (m, 1H), 4.11 -3.97 (m, 1H), 1.83-1.69 (m, 3H), 1.09-0.98 (m, 6H). $^{13}$C NMR (201 MHz, Methanol-$d_4$) δ 171.3, 170.9, 150.6, 150.5, 147.8, 147.8, 115.1, 115.1, 111.5, 111.5, 52.0, 51.8, 39.8, 39.6, 24.0, 23.9, 22.0, 21.8, 20.2, 20.0. UPLC-MS (m/z): 245.5 $[M + H]^+$. |

Biological Methods

Study 1—Isothermal Titration Calorimetry (ITC)

The dissociation constants ($K_D$) of the separated diastereomers (V-i) and (V-ii) for binding to *Escherichia Coli* LeuRS were determined by isothermal titration calorimetry (ITC).

*Escherichia coli* BL21(DE3) cells transformed with plasmid pQE-60 containing the open-reading frame sequence of one targeted aaRS (i.e., LeuRS) were induced with 1 mM IPTG (isopropyl β-D-1-thiogalactopyranoside) for 3 hours at 37° C. Bacterial cells were harvested and lysed with 20 mM HEPES (4-(2-hydroxyethyl)-1-piperazinylethanesulfonic acid) (pH 7.5), 300 mM NaCl, 15 mM imidazole and 1 mM DTT (1,4-dithio-D-threitol). The pathogenic aaRS was first purified by nickel affinity standard chromatography. The eluted protein was concentrated and then further purified by gel filtration using 50 mM HEPES (pH 7.5), 150 mM NaCl buffer.

ITC studies were carried out using a Microcal ITC$_{200}$ instrument (GE Healthcare). Protein concentration was determined by spectrophotometry by measuring the absorbance at 280 nm using a theoretical molar extinction coefficient of 169,140 $M^{-1}cm^{-1}$. Ligand stock solutions were prepared in DMSO at 62.5 mM concentration. The titrations were performed at 25° C. with 10-30 μM *E. Coli* LeuRS in 50 mM HEPES, 150 mM NaCl, pH 7.5 buffer containing 1% DMSO (v/v). The protein solution in the 200 μL sample cell was titrated with the inhibitor solution (diluted to 100-300 μM in the same buffer as the protein) using 1-2 μL injections every 140 seconds. All titrations were repeated at least three times. To correct for heats of dilution and mixing, the final baseline consisting of small peaks of identical size at the end of each experiment was subtracted. The experimental data were fitted to a theoretical titration curve (one site model) using MicroCal Origin 7 software. The arithmetic mean±standard deviation (SD) of K, ΔH, ΔS values from at least three experiments are shown in the following table.

TABLE 13

Isothermal Titration Calorimetry (ITC)

| Diastereomer | Replicate | K (M$^{-1}$) | ΔH (cal/mol) | ΔS (cal/mol/° C.) |
|---|---|---|---|---|
| (V-i) | 1 | 1.54 × 10$^8$ ± 1.91 × 10$^7$ | +1.489 × 10$^4$ ± 68.80 | −12.5 |
|  | 2 | 3.18 × 10$^8$ ± 4.92 × 10$^7$ | +1.370 × 10$^4$ ± 64.49 | −7.03 |
|  | 3 | 2.40 × 10$^8$ ± 3.27 × 10$^7$ | +1.381 × 10$^4$ ± 63.33 | −7.96 |
| (V-ii) | 1 | 8.35 × 10$^4$ ± 8.11 × 10$^3$ | −5690 ± 169.5 | +3.44 |
|  | 2 | 6.65 × 10$^4$ ± 7.70 × 10$^3$ | −5899 ± 283.8 | +2.28 |
|  | 3 | 7.70 × 10$^4$ ± 6.71 × 10$^3$ | −6200 ± 208.8 | +1.56 |

In the above table, the binding constant (K) was calculated as follows:

$$\Delta G = \Delta H - T\Delta S$$

$$K = \exp(-\Delta H/RT + \Delta S/R)$$

where R is the Gas Constant (1.9858775 cal/mol/° C.) and T is 25° C.

The dissociation constant ($K_D$) was calculated as follows:

$$K_D = 1/K$$

The calculated dissociation constants ($K_D$) are shown in the following table.

TABLE 14

Dissociation Constants ($K_D$) for Diastereomers

| Diastereomer | $K_D$ (nM) |
|---|---|
| First diastereomer (V-i) | 4.6 |
| Second diastereomer (V-ii) | 13000 |

The data demonstrate that the first diastereomer (V-i) binds with high affinity to *E. coli* LeuRS.

Study 2—Isothermal Titration Calorimetry (ITC)

*Escherichia coli* BL21(DE3) cells transformed with plasmid pQE-60 containing the open-reading frame sequence of one targeted aaRS (i.e., LeuRS) were induced with 1 mM IPTG (isopropyl β-D-1-thiogalactopyranoside) for 3 hours at 37° C. Bacterial cells were harvested and lysed with 20 mM HEPES (4-(2-hydroxyethyl)-1-piperazinylethanesulfonic acid) (pH 7.5), 300 mM NaCl, 15 mM imidazole and 1 mM DTT (1,4-dithio-D-threitol). The pathogenic aaRS was first purified by nickel affinity standard chromatography. The eluted protein was concentrated and then further purified by gel filtration using 50 mM HEPES (pH 7.5), 150 mM NaCl buffer.

ITC studies were carried out using a Microcal ITC$_{200}$ instrument (GE Healthcare). Protein concentration was determined by spectrophotometry by measuring the absorbance at 280 nm using a theoretical molar extinction coefficient of 169,140 M$^{-1}$cm$^{-1}$. Ligand stock solutions were prepared in DMSO at 62.5 mM concentration. The titrations were performed at 25° C. with 7.5-100 μM *E. Coli* LeuRS in 50 mM HEPES, 150 mM NaCl, pH 7.5 buffer containing 1% DMSO (v/v). The protein solution in the 280 μL sample cell was titrated with the inhibitor solution (diluted to 75-3000 μM in the same buffer as the protein) using 1-2 μL injections every 120-140 seconds. All titrations were repeated at least two times. To correct for heats of dilution and mixing, the final baseline consisting of small peaks of identical size at the end of each experiment was subtracted. The experimental data were fitted to a theoretical titration curve (one site model) using MicroCal Origin 7 SR4 software. The arithmetic mean±standard deviation (SD) of K, ΔH, ΔS values from at least three experiments are shown in the following table.

The data are summarised in the following table. Note that Compounds R-4.1 and S-4.1 (in Table 15, below) correspond to Compounds V-i and V-ii (in Tables 13 and 14, above), respectively.

TABLE 15

Isothermal Titration Calorimetry (ITC)

| Compound No. | $K_d$ (nM) | ΔG (kcal/mol) | ΔH (kcal/mol) |
|---|---|---|---|
| R-4.1 | 3.86 ± 0.24 | −11.48 ± 0.04 | −11.92 ± 0.34 |
| S-4.1 | 9130 ± 2720 | −6.89 ± 0.16 | −2.33 ± 0.13 |
| 4.4 | 159.07 ± 29.41 | −9.28 ± 0.11 | −9.06 ± 0.28 |
| 4.7 | 1823.42 ± 255.53 | −7.84 ± 0.09 | −1.66 ± 0.75 |
| 4.11 | 2.17 ± 0.08 | −11.82 ± 0.04 | −16.22 ± 0.60 |
| R-4.12 | 1.48 ± 0.08 | −11.96 ± 0.12 | −10.75 ± 1.06 |
| 4.13 | 6.62 ± 1.36 | −11.16 ± 0.12 | −8.69 ± 1.09 |
| 4.14 | 4.02 ± 0.38 | −11.45 ± 0.06 | −12.35 ± 0.04 |
| 4.15 | 10.56 ± 0.39 | −10.88 ± 0.03 | −10.74 ± 0.16 |
| 4.16 | 27.25 ± 8.44 | −10.34 ± 0.19 | −4.89 ± 0.08 |
| 4.17 | 4.47 ± 0.04 | −11.39 ± 0.01 | −9.72 ± 0.22 |
| 4.18 | 6.06 ± 0.49 | −11.20 ± 0.06 | −7.03 ± 0.14 |
| 4.19 | 3.35 ± 0.48 | −11.56 ± 0.09 | −8.49 ± 0.38 |
| 4.20 | 1.39 ± 0.07 | −12.08 ± 0.03 | −11.64 ± 0.45 |
| 4.21 | 6.61 ± 0.83 | −11.16 ± 0.07 | −8.23 ± 0.43 |
| 4.22 | 34.55 ± 0.76 | −10.17 ± 0.02 | −4.27 ± 0.19 |
| 4.23 | 17.47 ± 1.10 | −10.58 ± 0.03 | −7.06 ± 0.75 |
| 4.27 | 3.69 ± 0.05 | −11.50 ± 0.00 | −8.71 ± 1.08 |
| 4.29 | 9.14 ± 0.30 | −10.96 ± 0.01 | −10.95 ± 0.18 |
| 4.31 | 6.78 ± 1.73 | −11.15 ± 0.16 | −12.97 ± 2.04 |
| 4.32 | 4.61 ± 0.06 | −11.37 ± 0.01 | −10.62 ± 0.25 |
| 4.34 | 287.86 ± 42.88 | −8.93 ± 0.08 | −9.90 ± 0.40 |
| 4.35 | 16.43 ± 2.72 | −10.63 ± 0.10 | −9.97 ± 0.10 |
| 4.39 | 12.80 ± 1.60 | −10.77 ± 0.08 | −9.29 ± 0.62 |

Study 3—Antibacterial Activity

The antibacterial activity of the separated diastereomers (V-i) and (V-ii) was determined against wild type *E. Coli* strain BW25113.

The method described in "Methods for Dilution Antimicrobial Susceptibility Tests for Bacteria that Grow Aerobically; Approved Standard—Ninth Edition" (M07-A9; Vol. 32, No. 2) was used.

The results are summarized in the following table.

TABLE 16

Antibacterial EC50 for Diastereomers (*E. coli* BW25113)

| Diastereomer | EC$_{50}$ (mg/L) |
|---|---|
| First diastereomer (fast) (V-i) | 4 |
| Second diastereomer (slow) (V-ii) | >128 |

The data demonstrate that the first diastereomer (V-i) is a potent antibacterial agent.

Study 4—Antibacterial Activity

Minimum Inhibitory Concentrations (MICs) were determined by the broth micro-dilution method performed according to Clinical Laboratory Standards Institute guidelines. For testing, 5 mg/mL DMSO solutions were prepared by dissolving solids in DMSO. Standard antibiotics were prepared according to CLSI guidelines as 5 mg/mL stock solutions. Upon DMSO stock solutions preparation, the working solutions in MH media were prepared by adding 38.4 μL of stock solution to 1461.6 μL of MH media. Out of these working solutions 100 μL were transferred to wells in the third column of 96-well assay plates. Assay plates were previously filled with 50 μL of MH media in all wells except for the wells in the third column. Upon compounds and antibiotics addition, 50 μL was transferred from the third to the fourth column, then from the fourth to the fifth and so on. In this manner, the compounds and antibiotics were plated in 96-well assay plates in serial two fold dilutions giving final concentrations range of 64-0.125 μg/mL.

The bacterial strains tested were *Escherichia coli* ATCC 25922, *Escherichia coli* ATCC 25922 TolC deficient mutant, *Haemophilus influenzae* ATCC 49247, *Enterobacter cloacae* B1966 clinical isolate, *Klebsiella pneumoniae* ATCC 700603, *Pseudomonas aeruginosa* ATCC 27853, *Acinetobacter baumannii* B1931 clinical isolate.

MIC value was determined by visual inspection of bacterial growth within 96-well plates. The first column in which there was no visible growth of bacteria was determined as MIC value for compound or antibiotic tested in that particular row. ATCC strains were used as reference strains for which there is a determined value of MIC values for standard antibiotics. The assay is considered valid when MIC values for standard antibiotics are within CLSI designated range for ATCC strain tested.

TABLE 17

Antibacterial Activity (MIC, mg/L)

| Cmpd. No. | A | B | C | D | E | F | G |
|---|---|---|---|---|---|---|---|
| S-4.1 | 64 | 64 | >64 | >64 | >64 | >64 | >64 |
| R-4.1 | 2 | 2 | 4 | 8 | 32 | 8 | 16 |
| 4.11 | 1 |  | 4 | 2 | 64 | 8 | 4 |
| 4.12 | 2 |  | 8 | 4 | 16 | 16 | 4 |
| R-4.12 | 2 | 2 | 8 | 32 | >64 | 32 | 8 |
| 4.13 | 8 |  | 32 | 16 | >64 | 32 | 16 |
| 4.14 | 8 |  | 32 | 16 | 64 | 32 | 8 |
| 4.15 | 8 |  | 32 | 16 | 64 | 64 | 8 |
| 4.16 | 8 | 8 | 32 | >64 | >64 | 32 | 32 |
| 4.17 | >64 | 64 | >64 | >64 | >64 | >64 | >64 |
| 4.18 | 64 | 16 | >64 | >64 | >64 | >64 | >64 |
| 4.19 | 2 |  | 8 | 4 | >64 | 64 | 8 |
| 4.20 | 8 | 8 | >64 | >64 | >64 | >64 | 64 |
| 4.21 | 32 | 32 | >64 | >64 | >64 | >64 | >64 |
| 4.22 | 16 | 16 | 32 | 64 | >64 | 32 | >64 |
| 4.26 | 64 | 64 | >64 | >64 | >64 | >64 | >64 |
| 4.27 | 4 | 2 | 8 | 32 | >64 | >64 | 16 |
| 4.29 | 8 | 16 | 16 | 64 | >64 | 16 | 32 |
| 4.30 | 16 | 16 | 32 | 32 | 32 | 8 | 8 |
| 4.31 | 2 | 2 | 4 | 2 | 32 | 4 | 8 |
| 4.32 | 4 | 8 | 16 | 16 | >64 | 16 | 32 |
| 4.34 | 0.5 | 0.25 | 1 | 1 | 32 | 2 | 4 |
| 4.35 | 16 | 16 | 64 | >64 | >64 | >64 | >64 |
| 4.36 | 64 | 64 | >64 | >64 | >64 | >64 | >64 |
| 4.37 | 8 | 8 | 64 | >64 | >64 | 64 | 32 |
| 4.39 | 16 |  | 64 | 64 | >64 | 64 | 8 |
| Azithromycin | 4 | 0.5 | 16 | 32 | 32 | 16 | 2 |
| Ceftazidime | 0.25 | 0.25 | 0.5 | >64 | >64 | 2 | 16 |
| Ciprofloxacin | <0.125 | <0.125 | <0.125 | 1 | 64 | <0.125 | <0.125 |
| Meropenem | 0.5 | 0.5 | 0.5 | 0.5 | >64 | 8 | 4 |

Key:

A = *E. coli* ATCC 25922

B = *E. coli* EFFLUX del

C = *Enterobacter cloacae* B1966

D = *Kl. pneumoniae* ATCC 700603

E = *P. aeruginosa* ATCC 27853

F = *A. baumannii* B1931

G = *H. influenzae* ATCC 49247

Study 4—Human Cell Viability

Compounds were assessed for potential non-specific cytotoxic effects against a human hepatic cell line (HepG2 ATCC HB-8065). 96-well plates were seeded with HepG2 cells in concentration of 15,000 cells per well in 100 μL of MEM growth media completed with 1% NEAA and 1% sodium pyruvate. Border wells were filled with 100 μL of sterile PBS. Two days upon cells incubation, the compounds were added. Compound dilutions were prepared in 96-well V-bottom plate in pure DMSO. Growth media from 5 plates were aspirated and replaced with 98.7 μL of fresh growth media. 1.28 μL of compounds prepared in V-bottom plates were transferred with multichannel pipette into test plates (78.1× dilution). Final DMSO concentration was 1.28% per well. In control wells, 1.28 μL of DMSO was added in 98.7 μL of media. Compounds were tested in duplicates. Cells were incubated with compounds for 24 hours when cell viability was assessed by measuring ATP levels. ATP levels were measured by adding 50 μL of CellTiter-Glo reagent to each well and after 5 minutes of incubation luminescence was measured with SpectraMax i3. The potential effect of tested compounds on cell viability was determined by comparing the signal obtained in presence of different concentrations of the compounds with those obtained in the presence of DMSO only. The potential effects were then calculated and presented as $IC_{50}$ values (μg/mL).

TABLE 18

Cytotoxicity in HepG2 ATCC HB-8065 Cell Line

| Compound No. | $IC_{50}$ (μg/mL) |
|---|---|
| S-4.1 | >64 |
| R-4.1 | >64 |
| 4.2 | >32 |
| 4.3 | >64 |
| 4.4 | >64 |
| 4.5 | >32 |
| 4.6 | >32 |
| 4.7 | >64 |
| 4.8 | >64 |
| 4.9 | >64 |
| 4.10 | >64 |
| 4.11 | >64 |
| 4.12 | >64 |
| R-4.12 | >64 |
| 4.13 | >64 |
| 4.14 | >64 |
| 4.15 | >64 |
| 4.16 | >64 |
| 4.17 | 47.7 |
| 4.18 | >64 |
| 4.19 | >64 |
| 4.20 | >64 |
| 4.21 | >64 |
| 4.22 | >64 |
| 4.26 | >64 |
| 4.27 | >64 |
| 4.28 | >64 |
| 4.29 | >64 |
| 4.30 | 32.5 |
| 4.31 | >64 |
| 4.32 | >64 |
| 4.34 | >64 |
| 4.35 | >64 |
| 4.36 | 44.0 |
| 4.37 | >64 |
| 4.38 | >64 |
| 4.39 | 46 |
| 4.40 | >64 |
| 4.41 | >64 |

The foregoing has described the principles, preferred embodiments, and modes of operation of the present invention. However, the invention should not be construed as limited to the particular embodiments discussed. Instead, the above-described embodiments should be regarded as illustrative rather than restrictive. It should be appreciated that variations may be made in those embodiments by workers skilled in the art without departing from the scope of the present invention.

REFERENCES

A number of publications are cited herein in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

Cottrell et al., 2005, "Inhibitors of Serine Proteases, Particularly HCV NS3-NS4A Protease", international (PCT) patent publication number WO 2005/037860 A2 published 28 Apr. 2005.

Duron et al., 2014, "Cystathionine-Y-Gamma-Lyase (CSE) Inhibitors", international (PCT) patent publication number WO 2014/018569 A1 published 30 Jan. 2014.

Hurdle et al., 2005, "Prospects for aminoacyl-tRNA synthetase inhibitors as new antimicrobial agents", *Antimicrobial Agents and Chemotherapy*, Vol. 49, pp. 4821-4833.

Jirgensons et al., 2016, "Novel N-acyl-sulfonamide derivatives as aminoacyl-tRNA synthetase inhibitors", international (PCT) patent publication number WO 2016/129983 A1 published 18 Aug. 2016.

Laupland et al., 2003, "Treatment of *Staphylococcus aureus* colonization and prophylaxis for infection with topical intranasal mupirocin: An evidence-based review", *Clinical Infectious Diseases*, Vol. 37, pp. 933-938.

Ochsner et al., 2007, "Aminoacyl-tRNA synthetases: essential and still promising targets for new anti-infective agents", *Expert Opinion on Investigational Drugs*, Vol. 16, pp. 573-593.

Pham et al., 2014, "Aminoacyl-tRNA synthetases as drug targets in eukaryotic parasites", *Int. J. Parasitol. Drugs Drug Resist.*, Vol. 4, Issue 1, pp. 1-13.

Savile et al., 2005, "Subtilisin-catalyzed resolution of N-acyl arylsulfinamides", J. Amer. Chem. Soc., Vol. 127, No. 7, pp. 2104-2113.

Vondenhoff et al., 2011, "Aminoacyl-tRNA synthetase inhibitors as potential antibiotics", *Eur. J. Med. Chem.*, Vol. 46, pp. 5227-5236.

Zhang et al., 2013, "Discovery of N-(4-sulfamoylpheny) thioureas as *Tyrpanosoma brucei* leucyl-tRNA synthetase inhibitors", Organic & Biomolecular Chemistry, Vol. 11, pp. 5310-5324.

The invention claimed is:

1. A compound selected from compounds of the following formula pharmaceutically acceptable salts thereof:

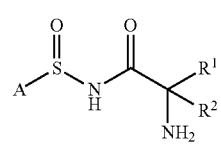

wherein:
- -A is independently -A$^C$ or -A$^H$;
- -A$^C$ is independently phenyl or naphthyl, and is optionally substituted with one or more substituents —R$^X$;
- -A$^H$ is independently C$_{5-12}$heteroaryl, and is optionally substituted with one or more substituents —R$^X$;
- each —R$^X$ is independently selected from:
  —R$^{XX}$, —R$^{XXU}$, —R$^{XXV}$, —R$^{XXH}$,
  —F, —Cl, —Br, —I,
  —OH, —OR$^{XX}$,
  -L$^{XX}$-OH, -L$^{XX}$-OR$^{XX}$,
  —CF$_3$, —OCF$_3$,
  —NH$_2$, —NHR$^{XX}$, —NR$^{XX}{}_2$, —R$^{XM}$,
  -L$^{XX}$-NH$_2$, -L$^{XX}$-NHR$^{XX}$, -L$^{XX}$-NR$^{XX}{}_2$, -L$^{XX}$-R$^{XM}$,
  —C(=O)OH, —C(=O)OR$^{XX}$, —OC(=O)R$^{XX}$,
  —C(=O)NH$_2$, —C(=O)NHR$^{XX}$, —C(=O)NR$^{XX}{}_2$,
  —C(=O)R$^{XM}$,
  —NHC(=O)R$^{XX}$, —NR$^{XN}$C(=O)R$^{XX}$,
  —NHC(=O)NH$_2$, —NHC(=O)NHR$^{XX}$, —NHC(=O)NR$^{XX}{}_2$, —NHC(=O)R$^{XM}$,
  —NR$^{XN}$C(=O)NH$_2$, —NR$^{XN}$C(=O)NHR$^{XX}$,
  —NR$^{XN}$C(=O)NR$^{XX}{}_2$, —NR$^{XN}$C(=O)R$^{XM}$,
  —NHC(=O)OR$^{XX}$, —NR$^{XN}$C(=O)OR$^{XX}$,
  —OC(=O)NH$_2$, —OC(=O)NHR$^{XX}$, —OC(=O)NR$^{XX}{}_2$, —OC(=O)R$^{XM}$,
  —NHC(=NH)NH$_2$,
  —C(=O)R$^{XX}$,
  —S(=O)NH$_2$, —S(=O)NHR$^{XX}$, —S(=O)NR$^{XX}{}_2$,
  —S(=O)R$^{XM}$,
  —S(=O)$_2$NH$_2$, —S(=O)$_2$NHR$^{XX}$, —S(=O)$_2$NR$^{XX}{}_2$,
  —S(=O)$_2$R$^{XM}$,
  —NHS(=O)R$^{XX}$, —NR$^{XN}$S(=O)R$^{XX}$,
  —NHS(=O)$_2$R$^{XX}$, —NR$^{XN}$S(=O)$_2$R$^{XX}$,
  —S(=O)R$^{XX}$, —S(=O)$_2$R$^{XX}$,
  —SH, —SR$^{XX}$, —CN, and —NO$_2$;
- and additionally, two adjacent groups —R$^X$, if present, may together form:
  —O—CH$_2$—O— or —O—CH$_2$CH$_2$—O—;
- wherein:
  - each -L$^{XX}$- is linear or branched saturated C$_{1-4}$alkylene;
  - each —R$^{XX}$ is independently linear or branched saturated C$_{1-4}$alkyl, phenyl, or benzyl;
  - each —R$^{XXU}$ is independently linear or branched C$_{2-4}$alkenyl;
  - each —R$^{XXV}$ is independently linear or branched C$_{2-4}$alkynyl;
  - each —R$^{XXH}$ is C$_{5-10}$ heteroaryl, and is optionally substituted with one or more groups —R$^{XMM}$;
  - each —R$^{XN}$ is linear or branched saturated C$_{1-4}$alkyl;
  - each —R$^{XM}$ is independently azetidino, pyrrolidino, piperidino, piperazino, morpholino, azepano, or diazepano, and is:
  - optionally substituted with one or more groups selected from:
    —R$^{XMM}$, —C(=O)R$^{XMM}$, —C(=O)OR$^{XMM}$, and —S(=O)$_2$R$^{XMM}$;
  - wherein each —R$^{XMM}$ is independently linear or branched saturated C$_{1-4}$alkyl, phenyl, or benzyl;
- —R$^1$ is iBu; and
- —R is H.

2. A compound according to claim 1, wherein -A is -A$^C$.

3. A compound according to claim 1, wherein -A is -A$^H$.

4. A compound according to claim 1, wherein -A$^C$, if present, is phenyl, and is optionally substituted with one or more substituents —R$^X$.

5. A compound according to claim 1, wherein -A$^C$, if present, is independently selected from:

wherein each —R$^{X1}$, —R$^{X2}$, —R$^{X3}$, —R$^{X4}$, —R$^{X5}$, and —R$^{X6}$ is independently as defined for —R$^X$.

6. A compound according to claim 1, wherein -A$^C$, if present, is independently selected from:

wherein each —R$^{X1}$, —R$^{X2}$, and —R$^{X3}$ is independently as defined for —R$^X$.

7. A compound according to claim 1, wherein -A$^C$, if present, is:

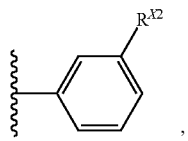

wherein —R$^{X2}$ is independently as defined for —R$^X$.

8. A compound according to claim 1, wherein -A$^C$, if present, is independently selected from:

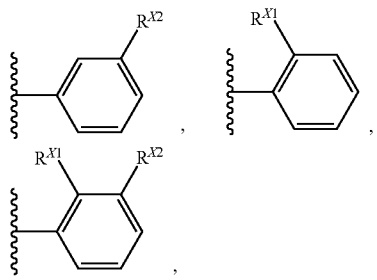

wherein each —R$^{X1}$ and —R$^{X2}$ is independently as defined for —R$^X$.

9. A compound according to claim 1, wherein -A$^C$, if present, is:

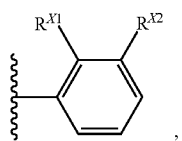

wherein each —R$^{X1}$ and —R$^{X2}$ is independently as defined for —R$^X$.

10. A compound according to claim 1, wherein -A$^H$, if present, is C$_{5-6}$ heteroaryl or C$_{9-10}$heteroaryl, and is optionally substituted with one or more substituents —R$^X$.

11. A compound according to claim 1, wherein -A$^H$, if present, is furanyl, thienyl, pyrrolyl, pyrazolyl, imidazolyl, oxazolyl, isoxazolyl, thiazolyl, isothiazolyl, pyridyl, pyridazinyl, pyrimidinyl, pyrazinyl, indolyl, benzimidazolyl, indazolyl, benzofuranyl, benzothienyl, benzooxazolyl, benzoisoxazolyl, benzothiazolyl, benzoisothiazolyl, quinolinyl, isoquinolinyl, cinnolinyl, quinazolinyl, quinoxalinyl, phthalazinyl, or benzopyranyl, and is optionally substituted with one or more substituents —R$^X$.

12. A compound according to claim 1, wherein -A$^H$, if present, is pyridyl, furanyl, thienyl, or quinolinyl, and is optionally substituted with one or more substituents —R$^X$.

13. A compound according to claim 1, wherein each —R$^X$, if present, is independently selected from:
—R$^{XX}$, —R$^{XXU}$, —R$^{XXV}$, —R$^{XXH}$,
—F, —Cl, —Br, —I,
—OH, —OR$^{XX}$,
—CF$_3$, —OCF$_3$,
—NH$_2$, —NHR$^{XX}$, —NR$^{XX}_2$, —R$^{XM}$,
—C(=O)OH, —C(=O)OR$^{XX}$, —OC(=O)R$^{XX}$,
—C(=O)NH$_2$, —C(=O)NHR$^{XX}$, —C(=O)NR$^{XX}_2$,
—C(=O)R$^{XM}$,
—NHC(=O)R$^{XX}$, —NR$^{XN}$C(=O)R$^{XX}$,
—C(=O)R$^{XX}$,
—S(=O)NH$_2$, —S(=O)NHR$^{XX}$, —S(=O)NR$^{XX}_2$,
—S(=O)R$^{XM}$,
—S(=O)$_2$NH$_2$, —S(=O)$_2$NHR$^{XX}$, —S(=O)$_2$NR$^{XX}_2$,
—S(=O)$_2$R$^{XM}$,
—NHS(=O)R$^{XX}$, —NR$^{XN}$S(=O)R$^{XX}$,
—NHS(=O)$_2$R$^{XX}$, —NR$^{XN}$S(=O)$_2$R$^{XX}$,
—S(=O)R$^{XX}$, —S(=O)$_2$R$^{XX}$,
—SR$^{XX}$, —CN, and —NO$_2$.

14. A compound according to claim 1, wherein each —R$^X$, if present, is independently selected from:
—R$^{XX}$, —R$^{XXU}$, —R$^{XXV}$,
—F, —Cl, —Br, —I,
—OH, —OR$^{XX}$,
—CF$_3$, —OCF$_3$,
—NH$_2$, —NHR$^{XX}$, —NR$^{XX}_2$, —R$^{XM}$,
—C(=O)OH, —C(=O)OR$^{XX}$, —OC(=O)R$^{XX}$,
—SR$^{XX}$, —CN, and —NO$_2$.

15. A compound according to claim 1, wherein each —R$^X$, if present, is independently selected from:
—R$^{XX}$,
—F, —Cl, —Br, —I,
—OH, —OR$^{XX}$,
—CF$_3$, —OCF$_3$.

16. A compound according to claim 1, which is selected from compounds of the following formulae, and pharmaceutically acceptable salts thereof:

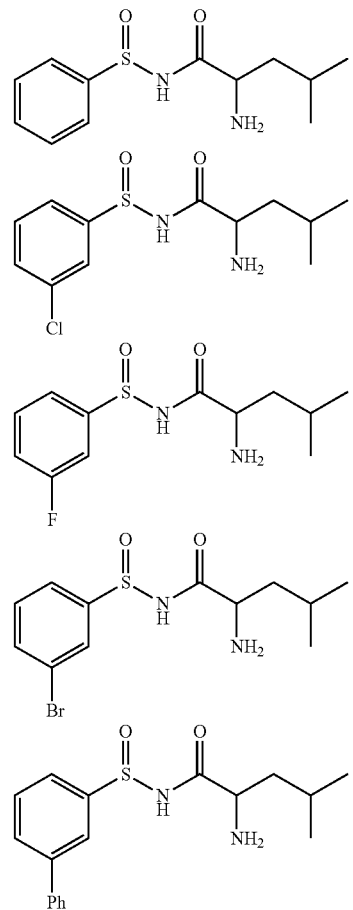

-continued
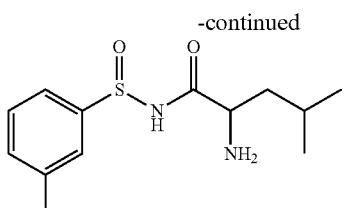
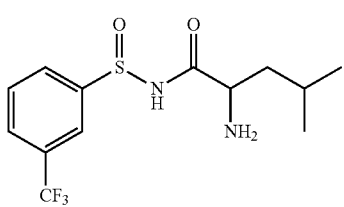
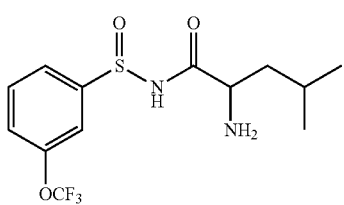
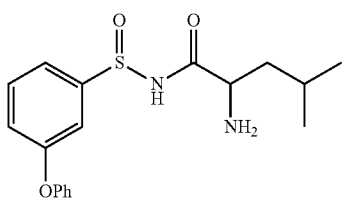
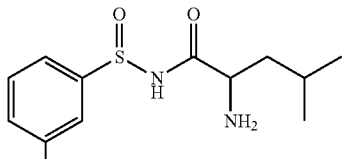
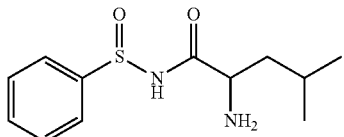
-continued
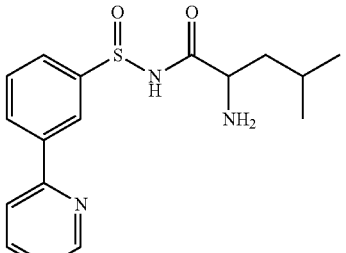
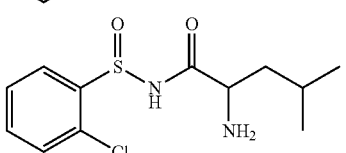
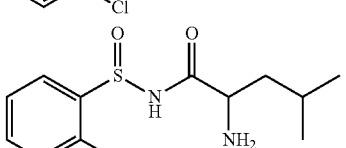
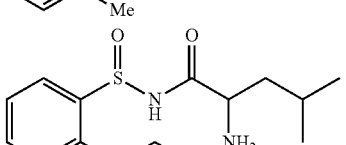
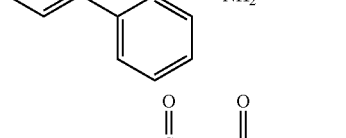
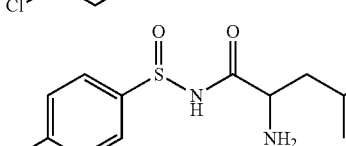
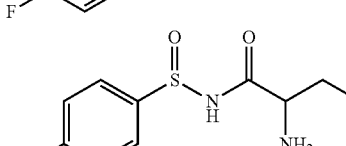
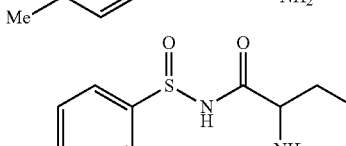
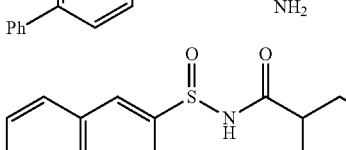
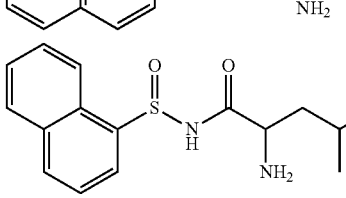

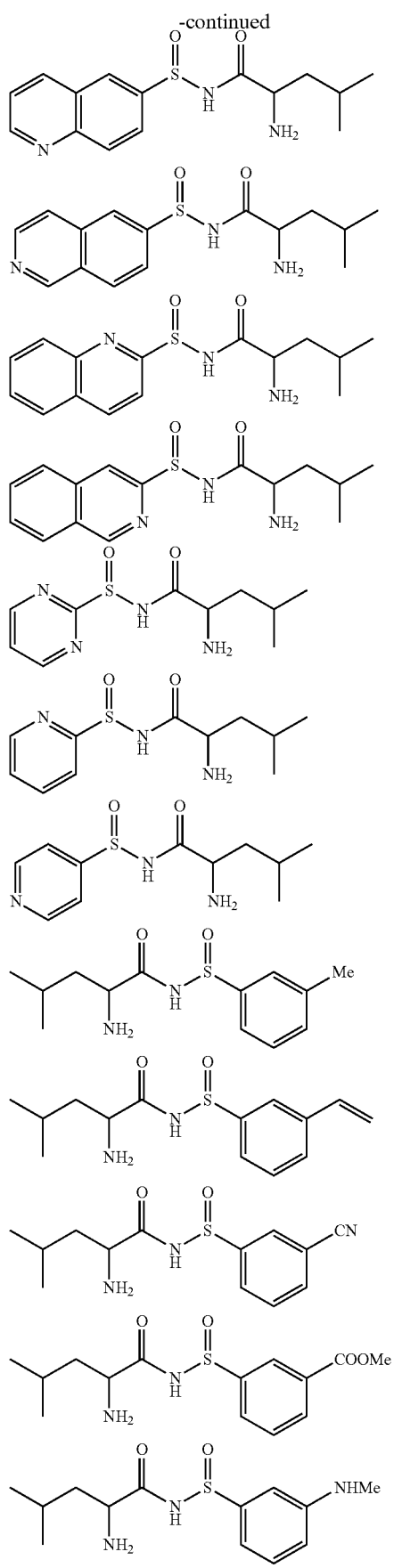
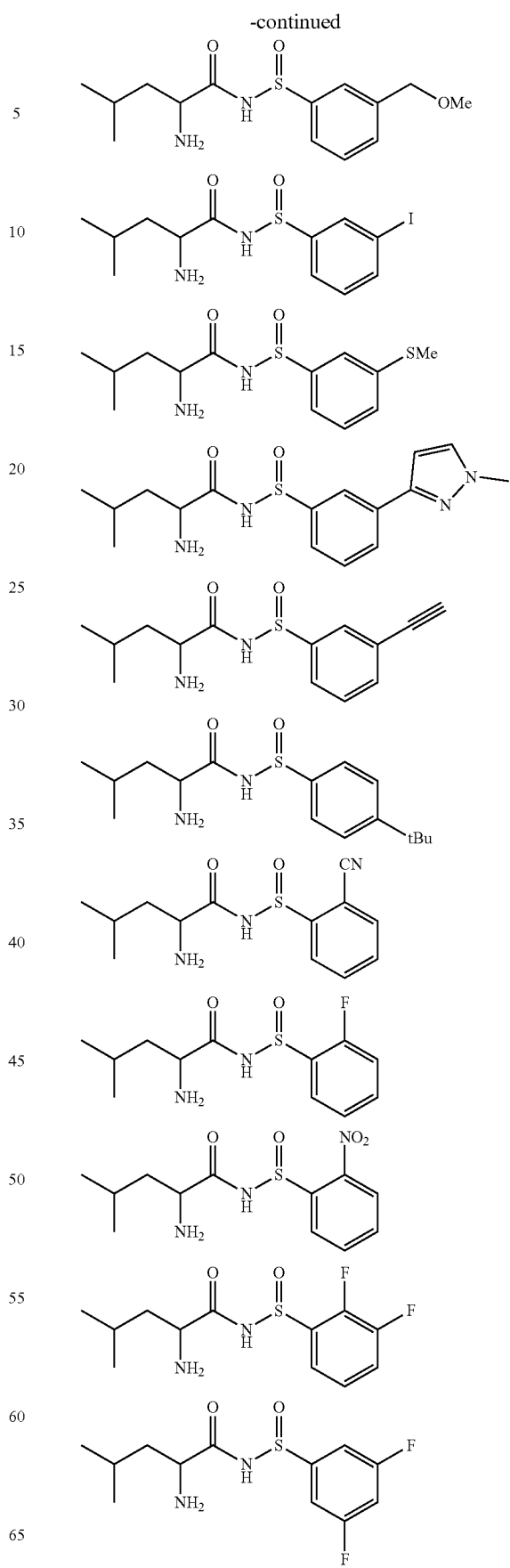

-continued

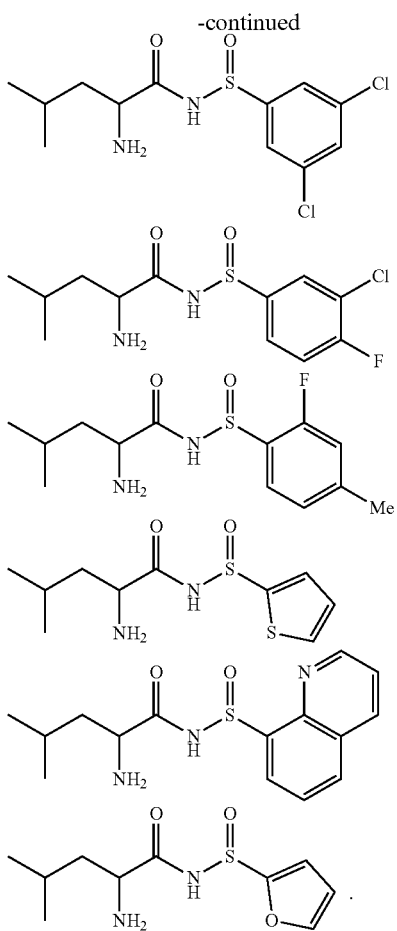

17. A compound according to claim 1, wherein the sulfur atom which forms part of the sulfoxide group is in the (R) configuration.

18. A compound according to claim 1, wherein the sulfur atom which forms part of the sulfoxide group is in the (S) configuration.

19. A compound according to claim 1, wherein the carbon atom to which —$R^1$ and —$R^2$ are attached is in the (R) configuration.

20. A compound according to claim 1, wherein the carbon atom to which —$R^1$ and —$R^2$ are attached is in the (S) configuration.

21. A pharmaceutical composition comprising a compound according to claim 1, and a pharmaceutically acceptable carrier or diluent.

22. A method of preparing a pharmaceutical composition comprising the step of mixing a compound according to claim 1, and a pharmaceutically acceptable carrier or diluent.

23. A method of inhibiting bacterial aminoacyl-tRNA synthetase, in vitro or in vivo, comprising contacting the synthetase with an effective amount of a compound according to claim 1.

24. A method of inhibiting bacterial aminoacyl-tRNA synthetase function in a cell, in vitro or in vivo, comprising contacting the cell with an effective amount of a compound according to claim 1.

25. A method of treatment of a bacterial infection of the human or animal body, comprising administering to a subject in need of treatment a therapeutically-effective amount of a compound according to claim 1.

26. A method according to claim 25, wherein the bacteria are Gram-positive bacteria.

27. A method according to claim 25, wherein the bacteria are Gram-negative bacteria.

28. A method according to claim 25, wherein the infection is:
a central nervous system infection;
an external ear infection;
an infection of the middle ear, including acute otitis media;
an infection of the cranial sinuses;
an eye infection;
an infection of the oral cavity, including an infection of the teeth, gums, or mucosa;
an upper respiratory tract infection;
a lower respiratory tract infection;
a genitourinary infection;
a urinary tract infection;
an intra-abdominal infection;
a gastrointestinal infection;
a gynecological infection;
septicemia;
a bone or joint infection;
a skin or skin structure infection;
bacterial endocarditis; or
a burn infection.

* * * * *